United States Patent
Bissantz et al.

(10) Patent No.: US 9,403,808 B2
(45) Date of Patent: Aug. 2, 2016

(54) PYRAZINE DERIVATIVES

(71) Applicant: Hoffmann-La Roche Inc., Nutley, NJ (US)

(72) Inventors: Caterina Bissantz, Village-Neuf (FR); Baledi Dhurwasulu, Andhra Pradesh (IN); Uwe Grether, Efringen-Kirchen (DE); Anindya Hazra, Kolkata (IN); Paul Hebeisen, Basel (CH); Stephan Roever, Inzlingen (DE); Mark Rogers-Evans, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 747 days.

(21) Appl. No.: 13/658,874

(22) Filed: Oct. 24, 2012

(65) Prior Publication Data
US 2013/0109665 A1 May 2, 2013

(30) Foreign Application Priority Data
Oct. 28, 2011 (EP) .................................... 11187181

(51) Int. Cl.
| | |
|---|---|
| *C07D 241/12* | (2006.01) |
| *C07D 241/18* | (2006.01) |
| *C07D 403/04* | (2006.01) |
| *C07D 413/12* | (2006.01) |
| *C07D 413/14* | (2006.01) |
| *C07D 401/12* | (2006.01) |
| *C07D 405/12* | (2006.01) |
| *C07D 409/14* | (2006.01) |
| *C07D 417/14* | (2006.01) |

(52) U.S. Cl.
CPC ............ *C07D 413/12* (2013.01); *C07D 241/12* (2013.01); *C07D 241/18* (2013.01); *C07D 401/12* (2013.01); *C07D 403/04* (2013.01); *C07D 405/12* (2013.01); *C07D 409/14* (2013.01); *C07D 413/14* (2013.01); *C07D 417/14* (2013.01)

(58) Field of Classification Search
None
See application file for complete search history.

(56) References Cited

U.S. PATENT DOCUMENTS

| | | | | |
|---|---|---|---|---|
| 7,691,863 | B2 * | 4/2010 | Dietz et al. | 514/255.05 |
| 2007/0293509 | A1 * | 12/2007 | Hebeisen et al. | 514/255.05 |
| 2008/0085905 | A1 * | 4/2008 | Dietz et al. | 514/255.05 |

FOREIGN PATENT DOCUMENTS

| | | |
|---|---|---|
| WO | 2006094691 | 9/2006 |
| WO | 2008/040649 | 4/2008 |

OTHER PUBLICATIONS

Wolff, Manfred E., Burger's Medicinal Chemistry, 1995, John Wiley &Sons, Inc., 5th Ed. Part 1, 975-977.*
Banker et al., "Modern Pharmaceutics", 1996, Marcel Decker, 3rd Edition, 596.*
Testa, Prodrug research; futilie or fertile?, 2004, Biochemical Pharmacology, 68, 2097-2106.*
Mallat et al., Expert Opin. Ther. Targets 11(3):403-409 (2007).
Lotersztajn et al., British Journal of Pharmacology 153:286-289 (2008).
International Search Report for PCT/EP2012/071093 dated Nov. 21, 2012.
The English translation of the Chinese Office Action, issued on Apr. 29, 2015, in the corresponding Chinese application No. 201280053009.8.

* cited by examiner

*Primary Examiner* — Gigi Huang

(57) ABSTRACT

The invention relates to a compound of formula (I)

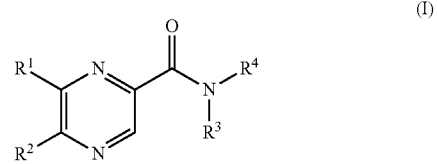

wherein $R^1$ to $R^4$ are defined as in the description and in the claims. The compound of formula (I) can be used as a medicament. In particular, the compound may be used as a preferential agonist of Cannabinoid Receptor 2.

2 Claims, No Drawings

PYRAZINE DERIVATIVES

PRIORITY TO RELATED APPLICATION(S)

This application claims the benefit of European Patent Application No. 11187181.0, filed Oct. 28, 2011, which is hereby incorporated by reference in its entirety.

FIELD OF THE INVENTION

The present invention relates to organic compounds useful for therapy and/or prophylaxis in a mammal, and in particular to compounds that are preferential agonists of Cannabinoid Receptor 2. The compound of formula (I) is particularly useful in the treatment or prophylaxis of e.g. pain, in particular chronic pain, atherosclerosis, regulation of bone mass, inflammation, ischemia, reperfusion injury, systemic fibrosis, liver fibrosis, lung fibrosis, kidney fibrosis, chronic allograft nephropathy, congestive heart failure, myocardial infarction, systemic sclerosis, glomerulonephropathy, thermal injury, burning, hypertrophic scars, keloids, gingivitis pyrexia, liver cirrhosis or tumors.

BACKGROUND OF THE INVENTION

The cannabinoid receptors are a class of cell membrane receptors belonging to the G protein-coupled receptor superfamily. There are currently two known subtypes, termed Cannabinoid Receptor 1 (CB1) and Cannabinoid Receptor 2 (CB2). The CB1 receptor is mainly expressed in the central nervous (i.e. amygdala cerebellum, hippocampus) system and to a lesser amount in the periphery. CB2, which is encoded by the CNR2 gene, is mostly expressed peripherally, on cells of the immune system, such as macrophages and T-cells (Ashton, J. C. et al. Curr Neuropharmacol 2007, 5(2), 73-80; Miller, A. M. et al. Br J Pharmacol 2008, 153(2), 299-308; Centonze, D., et al. Curr Pharm Des 2008, 14(23), 2370-42), and in the gastrointestinal system (Wright, K. L. et al. Br J Pharmacol 2008, 153(2), 263-70). The CB2 receptor is also widely distributed in the brain where it is found primarily on microglia and not neurons (Cabral, G. A. et al. Br J Pharmacol 2008, 153(2): 240-51).

The interest in CB2 receptor agonists has been steadily on the rise during the last decade (currently 30-40 patent applications/year) due to the fact that several of the early compounds have been shown to have beneficial effects in preclinical models for a number of human diseases including chronic pain (Beltramo, M. Mini Rev Med Chem 2009, 9(1), 11-25), atherosclerosis (Mach, F. et al. J Neuroendocrinol 2008, 20 Suppl 1, 53-7), regulation of bone mass (Bab, I. et al. Br J Pharmacol 2008, 153(2), 182-8), neuroinflammation (Cabral, G. A. et al. J Leukoc Biol 2005, 78(6), 1192-7), ischemia/reperfusion injury (Pacher, P. et al. Br J Pharmacol 2008, 153(2), 252-62), systemic fibrosis (Akhmetshina, A. et al. Arthritis Rheum 2009, 60(4), 1129-36; Garcia-Gonzalez, E. et al. Rheumatology (Oxford) 2009, 48(9), 1050-6), liver fibrosis (Julien, B. et al. Gastroenterology 2005, 128(3), 742-55; Munoz-Luque, J. et al. J Pharmacol Exp Ther 2008, 324(2), 475-83).

Ischemia/reperfusion (I/R) injury is the principal cause of tissue damage occurring in conditions such as stroke, myocardial infarction, cardiopulmonary bypass and other vascular surgeries, and organ transplantation, as well as a major mechanism of end-organ damage complicating the course of circulatory shock of various etiologies. All these conditions are characterized by a disruption of normal blood supply resulting in an insufficient tissue oxygenation. Re-oxygenation e.g., reperfusion is the ultimate treatment to restore normal tissue oxygenation. However the absence of oxygen and nutrients from blood creates a condition in which the restoration of circulation results in further tissue damage. The damage of reperfusion injury is due in part to the inflammatory response of damaged tissues. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane.

Remote ischemic preconditioning (RIPC) represents a strategy for harnessing the body's endogenous protective capabilities against the injury incurred by ischemia and reperfusion. It describes the intriguing phenomenon in which transient non-lethal ischemia and reperfusion of one organ or tissue confers resistance to a subsequent episode of "lethal" ischemia reperfusion injury in a remote organ or tissue. The actual mechanism through which transient ischemia and reperfusion of an organ or tissue confers protection is currently unknown although several hypotheses have been proposed.

The humoral hypothesis proposes that the endogenous substance (such as adenosine, bradykinin, opioids, CGRP, endocannabinoids, Angiotensin I or some other as yet unidentified humoral factor) generated in the remote organ or tissue enters the blood stream and activates its respective receptor in the target tissue and thereby recruiting the various intracellular pathways of cardioprotection implicated in ischemic preconditioning.

Recent data indicates that endocannabinnoids and their receptors, in particular CB2 might be involved in pre-conditioning and contribute to prevent reperfusion injury by downregulation of the inflammatory response (Pacher, P. et al. Br J Pharmacol 2008, 153(2), 252-62). Specifically, recent studies using CB2 tool agonists demonstrated the efficacy of this concept for reducing the I/R injury in the heart (Defer, N. et al. Faseb J 2009, 23(7), 2120-30), the brain (Zhang, M. et al. J Cereb Blood Flow Metab 2007, 27(7), 1387-96), the liver (Batkai, S. et al. Faseb J 2007, 21(8), 1788-800) and the kidney (Feizi, A. et al. Exp Toxicol Pathol 2008, 60(4-5), 405-10).

Moreover, over the last few years, a growing body of literature indicates that CB2 can also be of interest in subchronic and chronic setting. Specific upregulation of CB 1 and CB2 has been shown to be associated in animal models of chronic diseases associated with fibrosis (Garcia-Gonzalez, E. et al. Rheumatology (Oxford) 2009, 48(9), 1050-6; Yang, Y. Y. et al. Liver Int 2009, 29(5), 678-85) with a relevant expression of CB2 in myofibroblasts, the cells responsible for fibrosis progression.

Activation of CB2 receptor by selective CB2 agonist has in fact been shown to exert anti-fibrotic effect in diffuse systemic sclerosis (Garcia-Gonzalez, E. et al. Rheumatology (Oxford) 2009, 48(9), 1050-6) and CB2 receptor has emerged as a critical target in experimental dermal fibrosis (Akhmetshina, A. et al. Arthritis Rheum 2009, 60(4), 1129-36) and in in liver pathophysiology, including fibro genesis associated with chronic liver diseases (Lotersztajn, S. et al. Gastroenterol Clin Biol 2007, 31(3), 255-8; Mallat, A. et al. Expert Opin Ther Targets 2007, 11(3), 403-9; Lotersztajn, S. et al. Br J Pharmacol 2008, 153(2), 286-9).

The compounds of the invention bind to and modulate the CB2 receptor and have lower CB1 receptor activity.

SUMMARY OF THE INVENTION

The invention relates in part to a compound of formula (I)

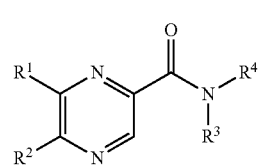

wherein
R$^1$ is halophenyl or cycloalkylalkoxy;
R$^2$ is selected from the group consisting of cycloalkyl, azetidinyl and difluoroazetidinyl;
one of R$^3$ and R$^4$ is hydrogen and the other one is —(CR$^5$R$^6$)—R$^7$ or -A-R$^7$;
or R$^2$ is cycloalkyl and R$^3$ and R$^4$ together with the nitrogen atom to which they are attached form piperidinyl or piperidinylamine;
R$^5$ and R$^6$ are independently selected from hydrogen, alkyl, haloalkyl, cycloalkyl, cycloalkylalkyl, phenyl, phenylalkyl and halophenyl;
or R$^5$ and R$^6$ together with the carbon atom to which they are attached form cycloalkyl or oxetanyl;
R$^7$ is selected from the group consisting of cyano, carboxy, 5-methyl-[1,2,4]oxadiazol-3-yl, 5-amino-[1,2,4]oxadiazol-3-yl, 5-alkoxy-[1,2,4]oxadiazol-3-yl, thiazolyl, alkylthiazolyl, pyridinyl, alkylaminocarbonyl, hydroxyalkyl, alkoxyalkyl, aminocarbonyl, alkoxycarbonyl, dialkylaminocarbonyl, methanesulfonyl-alkyl, 2-[1,2,4]oxadiazol-5-yl)-alkyl, 2-methyl-2H-[1,2,4]triazol-3-yl, 2-(2-methyl-2H-[1,2,4]triazol-3-yl)-alkyl, 2,4-dihydro-[1,2,4]triazol-3-on-5-yl, 2-(2,4-dihydro-[1,2,4]triazol-3-on-5-yl)-alkyl, phenyl, phenylalkyl, pyridinylalkyl, pyrazolyl, pyrazolylalkyl, [1,2,4]triazol-1-yl, 2-([1,2,4]triazol-1-yl)-alkyl, alkylaminocarbonylalkyl, hydroxyalkylaminocarbonyl, hydroxyalkylaminocarbonylalkyl, haloalkylaminocarbonyl, 5-phenyl-2-methyl-oxazol-4-yl-alkyl, aminocarbonylalkyl and halogen; and
A is cyclohexyl or thiophenyl;
provided that when R$^2$ is azetidinyl or difluoroazetidinyl and R$^7$ is hydroxyalkyl, halo alkyl, thiazolyl, pyridinyl, 2-([1,2,4]oxadiazol-5-yl)-alkyl, pyridinylalkyl, pyrazolylalkyl, 2-([1,2,4]triazol-1-yl)-alkyl, aminocarbonyl or alkoxycarbonyl, then one of R$^5$ and R$^6$ is cycloalkyl, cycloalkylalkyl, phenyl, halophenyl or phenylalkyl and the other one is hydrogen or alkyl;
or then R$^5$ and R$^6$ together with the carbon atom to which they are attached form cycloalkyl or oxetanyl;
or a pharmaceutically acceptable salt or ester thereof.

The present invention also relates in part to a pharmaceutical composition comprising the aforementioned compound and a therapeutically inert carrier.

DETAILED DESCRIPTION OF THE INVENTION

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain C$_1$-C$_8$ alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl more particularly methyl, ethyl, propyl, isopropyl, isobutyl, tert.-butyl and isopentyl. Particular examples of alkyl are methyl, ethyl, propyl, isopropyl, tert-butyl and isobutyl.

The term "cycloalkyl", alone or in combination, signifies a cycloalkyl ring with 3 to 8 carbon atoms and particularly a cycloalkyl ring with 3 to 6 carbon atoms. Examples of cycloalkyl are cyclopropyl, cyclobutyl, cyclopentyl and cyclohexyl, cycloheptyl and cyclooctyl. Particular cycloalkyl are cyclopropyl, cyclobutyl, cyclopentyl and cyclohexyl. Cyclopropyl and cyclobutyl are particular examples.

The term "alkoxy", alone or in combination, signifies a group of the formula alkyl-O- in which the term "alkyl" has the previously given significance, such as methoxy, ethoxy, n-propoxy, isopropoxy, n-butoxy, isobutoxy, sec-butoxy and tert-butoxy, particularly methoxy and ethoxy.

The terms "cycloalkyloxy" or "cycloalkoxy", alone or in combination, signify a group of the formula cycloalkyl-O— in which the term "cycloalkyl" has the previously given significance, such as cyclobutyloxy, cyclopentyloxy or cyclohexyloxy.

The term "phenyloxy", alone or in combination, signifies a phenyl-O— group.

The term "oxy", alone or in combination, signifies the —O— group.

The terms "halogen" or "halo", alone or in combination, signifies fluorine, chlorine, bromine or iodine and particularly fluorine, chlorine or bromine, more particularly fluorine and chlorine. The term "halo", in combination with another group, denotes the substitution of said group with at least one halogen, particularly substituted with one to five halogens, particularly one to three halogens. Particular halogens are fluorine and chlorine.

The term "haloalkyl", alone or in combination, denotes an alkyl group substituted with at least one halogen, particularly substituted with one to five halogens, particularly one to three halogens. A particular "haloalkyl" is trifluoromethyl.

The terms "hydroxyl" and "hydroxy", alone or in combination, signify the —OH group.

The term "carbonyl", alone or in combination, signifies the —C(O)— group.

The term "carboxy" or "carboxyl", alone or in combination, signifies the —COOH group.

The term "amino", alone or in combination, signifies the primary amino group (—NH$_2$), the secondary amino group (—NH—), or the tertiary amino group (—N—).

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

"Pharmaceutically acceptable esters" means that the compound of formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compound of formula (I), similar to the metabolically labile esters, which are capable of producing the parent compound of formula (I) in vivo, are within the scope of this invention.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wutts, 3$^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

The invention relates in part to a compound of formula (I)

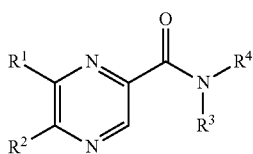

(I)

wherein
$R^1$ is halophenyl or cycloalkylalkoxy;
$R^2$ is selected from the group consisting of cycloalkyl, azetidinyl and difluoroazetidinyl;
one of $R^3$ and $R^4$ is hydrogen and the other one is —(CR$^5$R$^6$)—R$^7$;
or $R^2$ is cycloalkyl and $R^3$ and $R^4$ together with the nitrogen atom to which they are attached form piperidinyl;
$R^5$ and $R^6$ are independently selected from the group consisting of hydrogen, alkyl, haloalkyl, cycloalkyl, cycloalkylalkyl, phenyl and phenylalkyl;
or $R^5$ and $R^6$ together with the carbon atom to which they are attached form cycloalkyl;
$R^7$ is selected from the group consisting of cyano, carboxy, 5-methyl-[1,2,4]oxadiazol-3-yl, 5-amino-[1,2,4]oxadiazol-3-yl, 5-alkoxy-[1,2,4]oxadiazol-3-yl, thiazolyl, alkylthiazolyl, pyridinyl, alkylaminocarbonyl, hydroxyalkyl, alkoxyalkyl, aminocarbonyl, alkoxycarbonyl, dialkylaminocarbonyl, methanesulfonyl-alkyl, 2-[1,2,4]oxadiazol-5-yl)-alkyl, 2-methyl-2H-[1,2,4]triazol-3-yl, 2-(2-methyl-2H-[1,2,4]triazol-3-yl)-alkyl, 2,4-dihydro-[1,2,4]triazol-3-on-5-yl, 2-(2,4-dihydro-[1,2,4]triazol-3-on-5-yl)-alkyl, phenyl, phenylalkyl, pyridinylalkyl, pyrazolyl, pyrazolylalkyl, [1,2,4]triazol-1-yl, 2-([1,2,4]triazol-1-yl)-alkyl, alkylaminocarbonylalkyl, hydroxyalkylaminocarbonyl and hydroxyalkylaminocarbonylalkyl;

provided that when $R^2$ is azetidinyl or difluoroazetidinyl and $R^7$ is hydroxyalkyl, haloalkyl, thiazolyl, pyridinyl, 2-([1,2,4]oxadiazol-5-yl)-alkyl, pyridinylalkyl, pyrazolylalkyl, 2-([1,2,4]triazol-1-yl)-alkyl, aminocarbonyl or alkoxycarbonyl, then one of $R^5$ and $R^6$ is cycloalkyl, cycloalkylalkyl, phenyl or phenylalkyl and the other one is hydrogen or alkyl;
or a pharmaceutically acceptable salt or ester thereof.

The invention relates in particular to the following:
A compound of formula (I) wherein $R^1$ is cycloalkylalkoxy;
A compound of formula (I) wherein $R^1$ is cyclopropylmethoxy;
A compound of formula (I) wherein $R^2$ is cycloalkyl or difluoroazetidinyl;
A compound of formula (I) wherein $R^2$ is cyclopropyl or difluoroazetidinyl;
A compound of formula (I) wherein $R^2$ is cycloalkyl, in particular cyclopropyl, and $R^3$ and $R^4$ together with the nitrogen atom to which they are attached form piperidinyl or piperidinylamine;
A compound of formula (I) wherein $R^5$ and $R^6$ are independently selected from the group consisting of hydrogen, alkyl and cycloalkylalkyl;
A compound of formula (I) wherein $R^5$ and $R^6$ are independently selected from the group consisting of hydrogen, ethyl, tert-butyl, iso-butyl and cyclopropylmethyl;
A compound of formula (I) wherein $R^5$ and $R^6$ are independently selected from the group consisting of hydrogen, alkyl, cycloalkyl and cycloalkylalkyl;
A compound of formula (I) wherein $R^5$ and $R^6$ are independently selected from the group consisting of hydrogen, ethyl, tert-butyl, iso-butyl, cyclopropyl, cyclopropylmethyl and cyclobutylmethyl;
A compound of formula (I) wherein $R^5$ and $R^6$ are both alkyl at the same time, in particular both methyl at the same time;
A compound of formula (I) wherein one of $R^5$ and $R^6$ is alkyl and the other one is cycloalkyl or cycloalkylalkyl;
A compound of formula (I) wherein one of $R^5$ and $R^6$ is methyl and the other one is cyclopropyl or cyclopropylmethyl;
A compound of formula (I) wherein one of $R^5$ and $R^6$ is selected from the group consisting of ethyl, tert-butyl, iso-butyl and cyclopropylmethyl and the other one is hydrogen or ethyl;
A compound of formula (I) wherein one of $R^5$ and $R^6$ is selected from the group consisting of ethyl, tert-butyl, iso-butyl, cyclopropylmethyl and cyclobutylmethyl and the other one is hydrogen or ethyl.
A compound of formula (I) wherein $R^5$ and $R^6$ together with the carbon atom to which they are attached form cyclobutyl, cyclohexyl or oxetanyl, in particular cyclobutyl or cyclohexyl;
A compound of formula (I) wherein $R^7$ is selected from the group consisting of cyano, carboxy, 5-methyl-[1,2,4]oxadiazol-3-yl, 5-amino-[1,2,4]oxadiazol-3-yl, thiazolyl, alkylthiazolyl, pyridinyl, alkylaminocarbonyl, hydroxyalkyl, alkoxyalkyl, aminocarbonyl, dialkylaminocarbonyl, alkoxycarbonyl, 5-methyl-thiazol-2-yl, aminocarbonylalkyl and phenylalkyl;
A compound of formula (I) wherein $R^7$ is selected from the group consisting of alkoxyalkyl, aminocarbonyl, dialkylaminocarbonyl, alkoxycarbonyl, 5-methyl-thiazol-2-yl, aminocarbonylalkyl, 5-methyl-[1,2,4]oxadiazol-3-yl, hydroxyalkyl and phenylalkyl;

A compound of formula (I) wherein $R^7$ is selected from the group consisting of methoxycarbonyl, aminocarbonyl, dimethylaminocarbonyl, 5-methyl-thiazol-2-yl, 5-methyl-[1,2,4]oxadiazol-3-yl, aminocarbonylmethyl, hydroxymethyl, methoxyethyl and phenylethyl;

A compound of formula (I) wherein $R^7$ is selected from the group consisting of cyano, carboxy, 5-methyl-[1,2,4]oxadiazol-3-yl, 5-amino-[1,2,4]oxadiazol-3-yl, thiazolyl, alkylthiazolyl, pyridinyl, alkylaminocarbonyl, hydroxyalkyl, alkoxyalkyl, aminocarbonyl and dialkylaminocarbonyl;

A compound of formula (I) wherein $R^7$ is selected from the group consisting of cyano, carboxy, 5-methyl-[1,2,4]oxadiazol-3-yl, 5-amino-[1,2,4]oxadiazol-3-yl, thiazolyl, methylthiazolyl, pyridinyl, methylaminocarbonyl, hydroxymethyl, hydroxypropyl, methoxyalkyl, aminocarbonyl and dimethylaminocarbonyl;

A compound of formula (I) wherein $R^7$ is selected from the group consisting of alkoxyalkyl, aminocarbonyl and dialkylaminocarbonyl;

A compound of formula (I) wherein $R^7$ is selected from the group consisting of methoxycarbonyl, aminocarbonyl and dimethylaminocarbonyl;

A compound of formula (I) selected from the group consisting of 6-(3-Chloro-phenyl)-5-cyclopropyl-pyrazine-2-carboxylic acid [1-methyl-1-(5-methyl-[1,2,4]oxadiazol-3-yl)-ethyl]-amide;

6-(3-Chloro-phenyl)-5-cyclopropyl-pyrazine-2-carboxylic acid (cyano-dimethyl-methyl)-amide;

6-(3-Chloro-phenyl)-5-cyclopropyl-pyrazine-2-carboxylic acid [1-(5-methyl-[1,2,4]oxadiazol-3-yl)-cyclobutyl]-amide;

6-(3-Chloro-phenyl)-5-(3,3-difluoro-azetidin-1-yl)-pyrazine-2-carboxylic acid [1-methyl-1-(5-methyl-[1,2,4]oxadiazol-3-yl)-ethyl]-amide;

5-Azetidin-1-yl-6-(3-chloro-phenyl)-pyrazine-2-carboxylic acid [1-methyl-1-(5-methyl-[1,2,4]oxadiazol-3-yl)-ethyl]-amide;

6-(3-Chloro-phenyl)-5-cyclopropyl-pyrazine-2-carboxylic acid (1-methyl-1-thiazol-2-yl-ethyl)-amide;

6-(3-Chloro-phenyl)-5-cyclopropyl-pyrazine-2-carboxylic acid piperidin-1-ylamide;

6-Cyclopropylmethoxy-5-(3,3-difluoro-azetidin-1-yl)-pyrazine-2-carboxylic acid ((S)-2,2-dimethyl-1-methylcarbamoyl-propyl)-amide;

6-Cyclopropylmethoxy-5-(3,3-difluoro-azetidin-1-yl)-pyrazine-2-carboxylic acid [1-(5-methyl-[1,2,4]oxadiazol-3-yl)-cyclobutyl]-amide;

5-Cyclopropyl-6-cyclopropylmethoxy-pyrazine-2-carboxylic acid (3-hydroxy-1,1-dimethyl-propyl)-amide;

5-Cyclopropyl-6-cyclopropylmethoxy-pyrazine-2-carboxylic acid (1-hydroxymethyl-cyclobutyl)-amide;

5-Cyclopropyl-6-cyclopropylmethoxy-pyrazine-2-carboxylic acid [1-(5-methyl-[1,2,4]oxadiazol-3-yl)-cyclobutyl]-amide;

5-Cyclopropyl-6-cyclopropylmethoxy-pyrazine-2-carboxylic acid (1-hydroxymethyl-1-methyl-propyl)-amide;

5-Cyclopropyl-6-cyclopropylmethoxy-pyrazine-2-carboxylic acid ((S)-2,2-dimethyl-1-methylcarbamoyl-propyl)-amide;

5-Cyclopropyl-6-cyclopropylmethoxy-pyrazine-2-carboxylic acid ((S)-carbamoyl-phenyl-methyl)-amide;

6-Cyclopropylmethoxy-5-(3,3-difluoro-azetidin-1-yl)-pyrazine-2-carboxylic acid ((S)-1-cyclopropylmethyl-2-hydroxy-2-methyl-propyl)-amide;

5-Cyclopropyl-6-cyclopropylmethoxy-pyrazine-2-carboxylic acid ((S)-1-cyclopropylmethyl-2-hydroxy-2-methyl-propyl)-amide;

5-Cyclopropyl-6-cyclopropylmethoxy-pyrazine-2-carboxylic acid piperidin-1-ylamide;

5-Cyclopropyl-6-cyclopropylmethoxy-pyrazine-2-carboxylic acid (1-hydroxymethyl-2,2-dimethyl-propyl)-amide;

6-Cyclopropylmethoxy-5-(3,3-difluoro-azetidin-1-yl)-pyrazine-2-carboxylic acid [(S)-2-cyclopropyl-1-(5-methyl-[1,2,4]oxadiazol-3-yl)-ethyl]-amide;

6-Cyclopropylmethoxy-5-(3,3-difluoro-azetidin-1-yl)-pyrazine-2-carboxylic acid (1-cyclopropyl-2-hydroxy-ethyl)-amide;

6-Cyclopropylmethoxy-5-(3,3-difluoro-azetidin-1-yl)-pyrazine-2-carboxylic acid ((S)-carbamoyl-phenyl-methyl)-amide;

(S)-2-[(5-Cyclopropyl-6-cyclopropylmethoxy-pyrazine-2-carbonyl)-amino]-3,3-dimethyl-butyric acid methyl ester;

5-Cyclopropyl-6-cyclopropylmethoxy-pyrazine-2-carboxylic acid ((S)-2-cyclopropyl-1-methylcarbamoyl-ethyl)-amide;

5-Cyclopropyl-6-cyclopropylmethoxy-pyrazine-2-carboxylic acid ((S)-2-cyclopropyl-1-dimethylcarbamoyl-ethyl)-amide;

5-Cyclopropyl-6-cyclopropylmethoxy-pyrazine-2-carboxylic acid ((S)-3-methyl-1-methylcarbamoyl-butyl)-amide;

5-Cyclopropyl-6-cyclopropylmethoxy-pyrazine-2-carboxylic acid ((S)-1-dimethylcarbamoyl-3-methyl-butyl)-amide;

5-Cyclopropyl-6-cyclopropylmethoxy-pyrazine-2-carboxylic acid ((S)-1-carbamoyl-2-cyclopropyl-ethyl)-amide;

5-Cyclopropyl-6-cyclopropylmethoxy-pyrazine-2-carboxylic acid ((S)-1-carbamoyl-3-methyl-butyl)-amide;

2-[(5-Cyclopropyl-6-cyclopropylmethoxy-pyrazine-2-carbonyl)-amino]-2-ethyl-butyric acid methyl ester;

6-Cyclopropylmethoxy-5-(3,3-difluoro-azetidin-1-yl)-pyrazine-2-carboxylic acid ((S)-2-cyclopropyl-1-methylcarbamoyl-ethyl)-amide;

6-Cyclopropylmethoxy-5-(3,3-difluoro-azetidin-1-yl)-pyrazine-2-carboxylic acid ((S)-2-cyclopropyl-1-dimethylcarbamoyl-ethyl)-amide;

6-Cyclopropylmethoxy-5-(3,3-difluoro-azetidin-1-yl)-pyrazine-2-carboxylic acid ((S)-3-methyl-1-methylcarbamoyl-butyl)-amide;

6-Cyclopropylmethoxy-5-(3,3-difluoro-azetidin-1-yl)-pyrazine-2-carboxylic acid ((S)-1-dimethylcarbamoyl-3-methyl-butyl)-amide;

(S)-3-Cyclopropyl-2-[(5-cyclopropyl-6-cyclopropylmethoxy-pyrazine-2-carbonyl)-amino]-propionic acid methyl ester;

(S)-3-Cyclopropyl-2-{[6-cyclopropylmethoxy-5-(3,3-difluoro-azetidin-1-yl)-pyrazine-2-carbonyl]-amino}-propionic acid methyl ester;

5-Cyclopropyl-6-cyclopropylmethoxy-pyrazine-2-carboxylic acid ((S)-1-carbamoyl-2-phenyl-ethyl)-amide;

6-Cyclopropylmethoxy-5-(3,3-difluoro-azetidin-1-yl)-pyrazine-2-carboxylic acid ((S)-1-carbamoyl-2-phenyl-ethyl)-amide;

6-Cyclopropylmethoxy-5-(3,3-difluoro-azetidin-1-yl)-pyrazine-2-carboxylic acid ((S)-1-carbamoyl-2-cyclopropyl-ethyl)-amide;

5-Cyclopropyl-6-cyclopropylmethoxy-pyrazine-2-carboxylic acid [(S)-cyclopropyl-(5-methyl-[1,2,4]oxadiazol-3-yl)-methyl]-amide;

5-Cyclopropyl-6-cyclopropylmethoxy-pyrazine-2-carboxylic acid [(R)-cyclopropyl-(5-methyl-[1,2,4]oxadiazol-3-yl)-methyl]-amide;

6-Cyclopropylmethoxy-5-(3,3-difluoro-azetidin-1-yl)-pyrazine-2-carboxylic acid [(S)-cyclopropyl-(5-methyl-[1,2,4]oxadiazol-3-yl)-methyl]-amide;

6-Cyclopropylmethoxy-5-(3,3-difluoro-azetidin-1-yl)-pyrazine-2-carboxylic acid [(R)-cyclopropyl-(5-methyl-[1,2,4]oxadiazol-3-yl)-methyl]-amide;

(S)-2-[(5-Cyclopropyl-6-cyclopropylmethoxy-pyrazine-2-carbonyl)-amino]-3,3-dimethyl-butyric acid;

5-Cyclopropyl-6-cyclopropylmethoxy-pyrazine-2-carboxylic acid [1-methyl-1-(5-methyl-[1,2,4]oxadiazol-3-yl)-ethyl]-amide;

5-Cyclopropyl-6-cyclopropylmethoxy-pyrazine-2-carboxylic acid ((S)-1-pyridin-2-yl-ethyl)-amide;

6-Cyclopropylmethoxy-5-(3,3-difluoro-azetidin-1-yl)-pyrazine-2-carboxylic acid ((R)-2,2,2-trifluoro-1-pyridin-2-yl-ethyl)-amide;

6-Cyclopropylmethoxy-5-(3,3-difluoro-azetidin-1-yl)-pyrazine-2-carboxylic acid ((S)-2,2,2-trifluoro-1-pyridin-2-yl-ethyl)-amide;

5-Cyclopropyl-6-cyclopropylmethoxy-pyrazine-2-carboxylic acid ((S)-2,2,2-trifluoro-1-pyridin-2-yl-ethyl)-amide;

6-Cyclopropylmethoxy-5-(3,3-difluoro-azetidin-1-yl)-pyrazine-2-carboxylic acid (1-ethyl-1-methylcarbamoyl-propyl)-amide;

5-Cyclopropyl-6-cyclopropylmethoxy-pyrazine-2-carboxylic acid ((R)-1-hydroxymethyl-1,2-dimethyl-propyl)-amide;

5-Cyclopropyl-6-cyclopropylmethoxy-pyrazine-2-carboxylic acid ((S)-1-hydroxymethyl-1,2-dimethyl-propyl)-amide;

5-Cyclopropyl-6-cyclopropylmethoxy-pyrazine-2-carboxylic acid (1-ethyl-1-methylcarbamoyl-propyl)-amide;

5-Cyclopropyl-6-cyclopropylmethoxy-pyrazine-2-carboxylic acid [1-methyl-1-(4-methyl-thiazol-2-yl)-ethyl]-amide;

6-Cyclopropylmethoxy-5-(3,3-difluoro-azetidin-1-yl)-pyrazine-2-carboxylic acid [1-methyl-1-(4-methyl-thiazol-2-yl)-ethyl]-amide;

6-Cyclopropylmethoxy-5-(3,3-difluoro-azetidin-1-yl)-pyrazine-2-carboxylic acid [(R)-1-(5-methyl-[1,2,4]oxadiazol-3-yl)-ethyl]-amide;

5-Cyclopropyl-6-cyclopropylmethoxy-pyrazine-2-carboxylic acid [1-(5-amino-[1,2,4]oxadiazol-3-yl)-1-methyl-ethyl]-amide;

6-Cyclopropylmethoxy-5-(3,3-difluoro-azetidin-1-yl)-pyrazine-2-carboxylic acid [1-(5-amino-[1,2,4]oxadiazol-3-yl)-1-methyl-ethyl]-amide;

6-Cyclopropylmethoxy-5-(3,3-difluoro-azetidin-1-yl)-pyrazine-2-carboxylic acid ((S)-1-carbamoyl-1-phenyl-ethyl)-amide;

6-Cyclopropylmethoxy-5-(3,3-difluoro-azetidin-1-yl)-pyrazine-2-carboxylic acid [2-cyclopropyl-1-methyl-1-(5-methyl-[1,2,4]oxadiazol-3-yl)-ethyl]-amide;

6-Cyclopropylmethoxy-5-(3,3-difluoro-azetidin-1-yl)-pyrazine-2-carboxylic acid [1-cyclopropyl-1-(5-methyl-[1,2,4]oxadiazol-3-yl)-ethyl]-amide; and 5-Cyclopropyl-6-cyclopropylmethoxy-pyrazine-2-carboxylic acid [1-cyclopropyl-1-(5-methyl-[1,2,4]oxadiazol-3-yl)-ethyl]-amide.

The invention relates also in particular to a compound of formula (I) selected from the group consisting of:

5-Cyclopropyl-6-cyclopropylmethoxy-pyrazine-2-carboxylic acid [(S)-carbamoyl-(4-fluoro-phenyl)-methyl]-amide;

6-Cyclopropylmethoxy-5-(3,3-difluoro-azetidin-1-yl)-pyrazine-2-carboxylic acid [(S)-carbamoyl-(4-fluoro-phenyl)-methyl]-amide;

5-Cyclopropyl-6-cyclopropylmethoxy-pyrazine-2-carboxylic acid [(S)-2-cyclopropyl-1-(5-methyl-[1,2,4]oxadiazol-3-yl)-ethyl]-amide;

(S)-2-{[6-Cyclopropylmethoxy-5-(3,3-difluoro-azetidin-1-yl)-pyrazine-2-carbonyl]-amino}-4-methyl-pentanoic acid methyl ester;

6-Cyclopropylmethoxy-5-(3,3-difluoro-azetidin-1-yl)-pyrazine-2-carboxylic acid [(S)-3-methyl-1-(2,2,2-trifluoro-ethylcarbamoyl)-butyl]-amide;

6-Cyclopropylmethoxy-5-(3,3-difluoro-azetidin-1-yl)-pyrazine-2-carboxylic acid [(S)-carbamoyl-(4-chloro-phenyl)-methyl]-amide;

5-Cyclopropyl-6-cyclopropylmethoxy-pyrazine-2-carboxylic acid (4-hydroxy-1,1-dimethyl-butyl)-amide;

5-Cyclopropyl-6-cyclopropylmethoxy-pyrazine-2-carboxylic acid (1,1-dimethyl-3-pyridin-4-yl-propyl)-amide;

5-Cyclopropyl-6-cyclopropylmethoxy-pyrazine-2-carboxylic acid [1,1-dimethyl-2-(5-methyl-2-phenyl-oxazol-4-yl)-ethyl]-amide;

5-Cyclopropyl-6-cyclopropylmethoxy-pyrazine-2-carboxylic acid (1,1-dimethyl-3-pyridin-4-yl-butyl)-amide;

1-{[6-Cyclopropylmethoxy-5-(3,3-difluoro-azetidin-1-yl)-pyrazine-2-carbonyl]-amino}-cyclobutanecarboxylic acid methyl ester;

5-Cyclopropyl-6-cyclopropylmethoxy-pyrazine-2-carboxylic acid [1-methyl-1-(5-methyl-thiazol-2-yl)-ethyl]-amide;

6-Cyclopropylmethoxy-5-(3,3-difluoro-azetidin-1-yl)-pyrazine-2-carboxylic acid [1-methyl-1-(5-methyl-thiazol-2-yl)-ethyl]-amide;

5-Cyclopropyl-6-cyclopropylmethoxy-pyrazine-2-carboxylic acid ((5)-1-carbamoylmethyl-2-methyl-propyl)-amide;

6-Cyclopropylmethoxy-5-(3,3-difluoro-azetidin-1-yl)-pyrazine-2-carboxylic acid ((5)-1-carbamoylmethyl-2-methyl-propyl)-amide;

(+)-6-Cyclopropylmethoxy-5-(3,3-difluoro-azetidin-1-yl)-pyrazine-2-carboxylic acid [2-cyclopropyl-1-methyl-1-(5-methyl-[1,2,4]oxadiazol-3-yl)-ethyl]-amide;

(−)-6-Cyclopropylmethoxy-5-(3,3-difluoro-azetidin-1-yl)-pyrazine-2-carboxylic acid [2-cyclopropyl-1-methyl-1-(5-methyl-[1,2,4]oxadiazol-3-yl)-ethyl]-amide;

2-Cyclopropyl-2-{[6-cyclopropylmethoxy-5-(3,3-difluoro-azetidin-1-yl)-pyrazine-2-carbonyl]-amino}-propionic acid methyl ester;

(+)-6-Cyclopropylmethoxy-5-(3,3-difluoro-azetidin-1-yl)-pyrazine-2-carboxylic acid ((1R,2S)-rel-2-carbamoyl-cyclohexyl)-amide;

(+)-5-Cyclopropyl-6-cyclopropylmethoxy-pyrazine-2-carboxylic acid cis-2-carbamoyl-cyclohexyl)-amide;

(+)-5-Cyclopropyl-6-cyclopropylmethoxy-pyrazine-2-carboxylic acid cis-2-carbamoyl-cyclohexyl)-amide;

5-Cyclopropyl-6-cyclopropylmethoxy-pyrazine-2-carboxylic acid (3-carbamoylmethyl-oxetan-3-yl)-amide;

6-Cyclopropylmethoxy-5-(3,3-difluoro-azetidin-1-yl)-pyrazine-2-carboxylic acid (3-carbamoylmethyl-oxetan-3-yl)-amide;

(+)-6-Cyclopropylmethoxy-5-(3,3-difluoro-azetidin-1-yl)-pyrazine-2-carboxylic acid [1-cyclopropyl-1-(5-methyl-[1,2,4]oxadiazol-3-yl)-ethyl]-amide;

(−)-6-Cyclopropylmethoxy-5-(3,3-difluoro-azetidin-1-yl)-pyrazine-2-carboxylic acid [1-cyclopropyl-1-(5-methyl-[1,2,4]oxadiazol-3-yl)-ethyl]-amide;

6-Cyclopropylmethoxy-5-(3,3-difluoro-azetidin-1-yl)-pyrazine-2-carboxylic acid (1-carbamoyl-2-methyl-propyl)-amide;

6-Cyclopropylmethoxy-5-(3,3-difluoro-azetidin-1-yl)-pyrazine-2-carboxylic acid (1-carbamoyl-cyclohexyl)-amide;

6-Cyclopropylmethoxy-5-(3,3-difluoro-azetidin-1-yl)-pyrazine-2-carboxylic acid (1-hydroxymethyl-cyclohexyl)-amide;
6-Cyclopropylmethoxy-5-(3,3-difluoro-azetidin-1-yl)-pyrazine-2-carboxylic acid (1-dimethylcarbamoyl-2-methyl-propyl)-amide;
5-Cyclopropyl-6-cyclopropylmethoxy-pyrazine-2-carboxylic acid (1-dimethylcarbamoyl-2-methyl-propyl)-amide;
6-Cyclopropylmethoxy-5-(3,3-difluoro-azetidin-1-yl)-pyrazine-2-carboxylic acid (5-chloro-thiophen-2-yl)-amide;
5-Cyclopropyl-6-cyclopropylmethoxy-pyrazine-2-carboxylic acid (1-hydroxymethyl-cyclohexyl)-amide;
5-Cyclopropyl-6-cyclopropylmethoxy-pyrazine-2-carboxylic acid (3-methoxy-1,1-dimethyl-propyl)-amide;
6-Cyclopropylmethoxy-5-(3,3-difluoro-azetidin-1-yl)-pyrazine-2-carboxylic acid (2-cyclobutyl-1-methylcarbamoyl-ethyl)-amide;
6-Cyclopropylmethoxy-5-(3,3-difluoro-azetidin-1-yl)-pyrazine-2-carboxylic acid (2-cyclobutyl-1-dimethylcarbamoyl-ethyl)-amide;
5-Cyclopropyl-6-cyclopropylmethoxy-pyrazine-2-carboxylic acid (2-cyclobutyl-1-methylcarbamoyl-ethyl)-amide;
6-Cyclopropylmethoxy-5-(3,3-difluoro-azetidin-1-yl)-pyrazine-2-carboxylic acid (3-methoxy-1,1-dimethyl-propyl)-amide;
6-Cyclopropylmethoxy-5-(3,3-difluoro-azetidin-1-yl)-pyrazine-2-carboxylic acid (1-cyclobutylmethyl-2-hydroxy-ethyl)-amide;
6-Cyclopropylmethoxy-5-(3,3-difluoro-azetidin-1-yl)-pyrazine-2-carboxylic acid (1-carbamoyl-2-cyclobutyl-ethyl)-amide;
6-Cyclopropylmethoxy-5-(3,3-difluoro-azetidin-1-yl)-pyrazine-2-carboxylic acid (1,1-dimethyl-3-phenyl-propyl)-amide;
5-Cyclopropyl-6-cyclopropylmethoxy-pyrazine-2-carboxylic acid (2-cyclobutyl-1-dimethylcarbamoyl-ethyl)-amide;
5-Cyclopropyl-6-cyclopropylmethoxy-pyrazine-2-carboxylic acid (1-carbamoyl-2-cyclobutyl-ethyl)-amide;
5-Cyclopropyl-6-cyclopropylmethoxy-pyrazine-2-carboxylic acid (1-cyclobutylmethyl-2-hydroxy-ethyl)-amide;
5-Cyclopropyl-6-cyclopropylmethoxy-pyrazine-2-carboxylic acid (2-carbamoyl-1,1-dimethyl-ethyl)-amide; and
6-Cyclopropylmethoxy-5-(3,3-difluoro-azetidin-1-yl)-pyrazine-2-carboxylic acid (2-carbamoyl-1,1-dimethyl-ethyl)-amide.

The invention relates in particular to a compound of formula (I) selected from
(S)-2-[(5-Cyclopropyl-6-cyclopropylmethoxy-pyrazine-2-carbonyl)-amino]-3,3-dimethyl-butyric acid methyl ester;
5-Cyclopropyl-6-cyclopropylmethoxy-pyrazine-2-carboxylic acid ((S)-1-dimethylcarbamoyl-3-methyl-butyl)-amide;
5-Cyclopropyl-6-cyclopropylmethoxy-pyrazine-2-carboxylic acid ((S)-1-carbamoyl-2-cyclopropyl-ethyl)-amide;
5-Cyclopropyl-6-cyclopropylmethoxy-pyrazine-2-carboxylic acid ((S)-1-carbamoyl-3-methyl-butyl)-amide;
2-[(5-Cyclopropyl-6-cyclopropylmethoxy-pyrazine-2-carbonyl)-amino]-2-ethyl-butyric acid methyl ester; and
(S)-3-Cyclopropyl-2-{[6-cyclopropylmethoxy-5-(3,3-difluoro-azetidin-1-yl)-pyrazine-2-carbonyl]-amino}-propionic acid methyl ester.

The invention relates also in particular to a compound of formula (I) selected from
(S)-2-{[6-Cyclopropylmethoxy-5-(3,3-difluoro-azetidin-1-yl)-pyrazine-2-carbonyl]-amino}-4-methyl-pentanoic acid methyl ester;
6-Cyclopropylmethoxy-5-(3,3-difluoro-azetidin-1-yl)-pyrazine-2-carboxylic acid [1-methyl-1-(5-methyl-thiazol-2-yl)-ethyl]-amide;
(−)-6-Cyclopropylmethoxy-5-(3,3-difluoro-azetidin-1-yl)-pyrazine-2-carboxylic acid [2-cyclopropyl-1-methyl-1-(5-methyl-[1,2,4]oxadiazol-3-yl)-ethyl]-amide;
2-Cyclopropyl-2-{[6-cyclopropylmethoxy-5-(3,3-difluoro-azetidin-1-yl)-pyrazine-2-carbonyl]-amino}-propionic acid methyl ester;
6-Cyclopropylmethoxy-5-(3,3-difluoro-azetidin-1-yl)-pyrazine-2-carboxylic acid (3-carbamoylmethyl-oxetan-3-yl)-amide;
6-Cyclopropylmethoxy-5-(3,3-difluoro-azetidin-1-yl)-pyrazine-2-carboxylic acid (1-hydroxymethyl-cyclohexyl)-amide;
6-Cyclopropylmethoxy-5-(3,3-difluoro-azetidin-1-yl)-pyrazine-2-carboxylic acid (3-methoxy-1,1-dimethyl-propyl)-amide;
6-Cyclopropylmethoxy-5-(3,3-difluoro-azetidin-1-yl)-pyrazine-2-carboxylic acid (1-cyclobutylmethyl-2-hydroxy-ethyl)-amide; and
6-Cyclopropylmethoxy-5-(3,3-difluoro-azetidin-1-yl)-pyrazine-2-carboxylic acid (1,1-dimethyl-3-phenyl-propyl)-amide.

The compounds of formula (I) can be prepared by a process, which process comprises coupling a compound of formula II

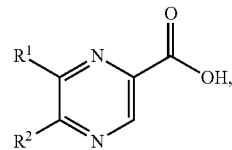

wherein $R^1$ an $R^2$ are as defined herein before, with an amine of the formula III

wherein $R^3$ and $R^4$ are as defined herein before, by amide coupling methods known in the art, as for example with the help of an amide coupling agent under basic conditions, and, if desired, converting the resulting compound of formula (I) into a pharmaceutically acceptable salt thereof.

Compounds of formula III or II may contain functional groups that would interfere with the coupling procedures described for the amide coupling step (II to I). In this case it is understood that III or II need to be suitably protected by methods known in the art before conducting the amide coupling procedure and compounds need to be deprotected after the coupling step by methods known in the art to deliver compounds of formula (I).

Coupling agents for the reaction of compounds of formula II with amines of formula III are for example N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU), or O-benzotriazole-N,N,N',N'-tetramethyl-uronium-hexafluoro-phosphate (HBTU). Particular coupling agents are TBTU and HATU. Suitable bases include triethylamine, N-methylmorpholine and particularly diisopropylethylamine. Alternative methods known in the art may commence by preparing the acid chloride from II and coupling with an amine of formula III in the presence of a suitable base.

The synthesis of the compounds with the general structure (I) can, for example, be accomplished according to the following schemes. Unless otherwise indicated, $R^1$ to $R^4$ are as defined above.

Following the procedure according to scheme 1, compound AA (3,5-dibromo-2-pyrazinamine, CAN 24241-18-7) can be used as starting material for the synthesis of compounds I-a where $R^1$ is halophenyl ($R^{1'}$ is halophenyl).

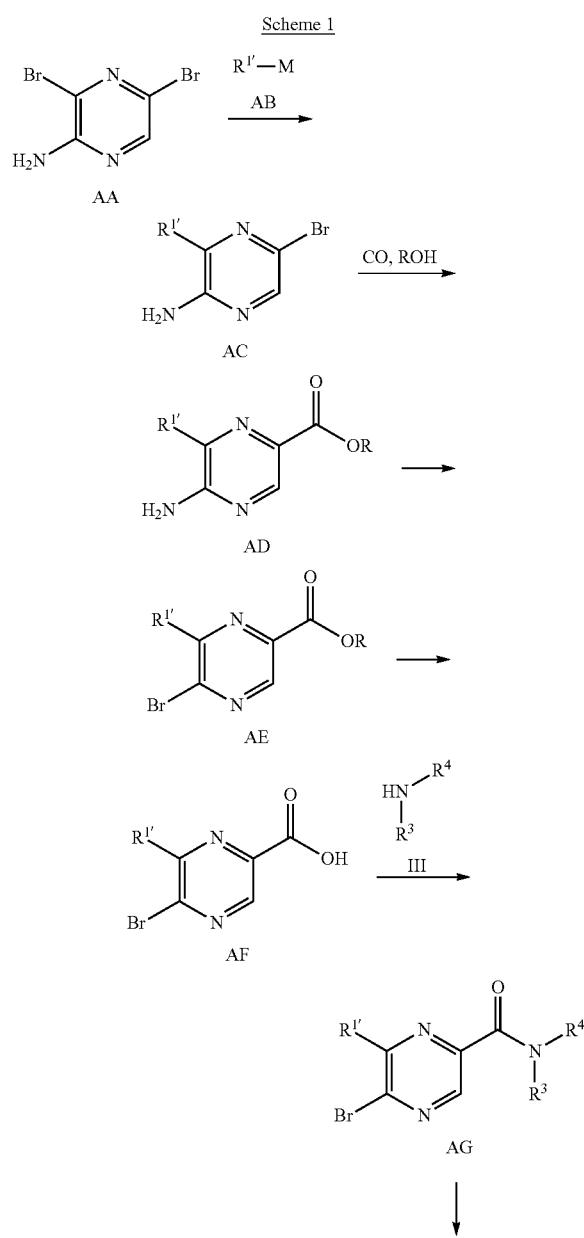

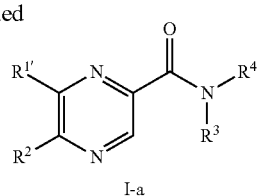

Compound AC can be prepared from AA by coupling a suitably substituted aryl-metal species of formula AB, particularly an arylboronic acid or arylboronic acid ester in the presence of a suitable catalyst, in particular a palladium catalyst and more particularly tetrakis(triphenylphosphine)-palladium(0) and a base such as triethylamine, potassium phosphate, and in particular sodium carbonate in an inert solvent such as dimethylformamide, toluene, tetrahydrofurane, acetonitrile and in particular dimethoxyethane at temperatures from room temperature to the boiling point of the solvent mixture.

Compounds of the general formula AD can be obtained from compounds of the general formula AC by palladium (II), particularly palladium(II) acetate catalyzed carbonylation in the presence of a suitable base such as a tertiary amine base, particularly triethylamine in a suitable solvent such as an alcohol, particularly methanol.

Compounds of the general formula AE can be obtained from compounds of the general formula AD by reaction with nitrosating agents such as a metal nitrite or an organic nitrite more particularly isoamylnitrite, in the presence of a bromide source such as hydrobromic acid or more particularly trimethylbromosilane in a suitable solvent such as halogenated hydrocarbons more particularly dibromomethane.

The saponification of the ester of general formula AE by methods well known to the ones skilled in the art—using e.g. aqueous LiOH, NaOH or KOH in tetrahydrofuran/ethanol or another suitable solvent at temperatures between 0° C. and the reflux temperature of the solvent employed—leads to an acid of general formula AF.

Compound AG can be prepared from AF and the corresponding amine of formula III by suitable amide bond forming reactions. These reactions are known in the art. For example coupling reagents like N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU), and O-benzotriazole-N,N,N',N'-tetramethyl-uronium-hexafluoro-phosphate (HBTU) can be employed to affect such transformation. Alternative methods known in the art may commence by preparing the acid chloride from AF and coupling with an amine of formula III in the presence of a suitable base. A convenient method is to use for example 1-chloro-N,N,2-trimethylpropenylamine and a base, for example N-ethyl-N-isopropylpropan-2-amine (DIEA) in an inert solvent such as for example dimethylformamide at room temperature.

Amines III are either commercially available, described in the literature, can be synthesized by a person skilled in the art or obtained as described in the experimental part.

Compounds I-a where $R^2$ is cycloalkyl can be prepared from AG by coupling a suitably substituted cycloalkyl or cycloalkenyl metal species, particularly a cyclopropyl metal species, like cyclopropylzinc(II) chloride, or cyclopropylboronic acid or cyclopropyltrifluoro-borate salts with AG in the presence of a suitable catalyst, particularly a palladium catalyst like tetrakis-(triphenyl-phosphine)palladium, or [1,3-bis (2,6-diisopropylphenyl)imidazol-2-ylidene](3-chloropyridyl)-palladium(II) dichloride, or palladium(II)acetate in an inert solvent such as THF or toluene at room temperature up to the reflux temperature of the solvent. The person skilled in the art will appreciate that for coupling the cycloalkyl- or cycloalkenyl-boron species the addition of a suitable base, like potassium phosphate is necessary for the reaction to commence. In cases where the practitioner skilled in the art chooses to couple with a cycloalkenyl metal species, like cycloalkenylboronic acid esters, compounds I-a will be obtained only after an additional hydrogenation step, for example by hydrogenation with hydrogen gas in the presence of a palladium catalyst, for example palladium on charcoal, in an inert solvent, for example ethanol, at suitable temperatures and pressures, particularly at ambient temperature and pressure.

Compounds I-a where $R^2$ is azetidinyl or difluoroazetidinyl can be prepared from AG by reacting with the corresponding azetidine in the presence of a base, particularly DBU or triethylamine, in an inert solvent, particularly DMSO or dioxane at temperatures ranging from room temperature to 45° C.

Following the procedure according to scheme 2, compound BA (5-chloro-pyrazine-2-carboxylic acid methyl ester, CAN 33332-25-1) can be used as starting material for the synthesis of compounds I-b where $R^2$ is azetidinyl or difluoroazetidinyl ($R^{2'}$ is azetidinyl or difluoroazetidinyl). BA is either commercially available, or can be synthesized by a person skilled in the art as described in the literature.

Compound BB can be prepared from BA by reacting with the corresponding azetidine in the presence of a base, particularly triethylamine, in an inert solvent, particularly dioxane at temperatures ranging from room temperature to 45° C.

Conversion of compound BB to BC can be achieved by electrophilic aromatic bromination in a suitable solvent, particularly by bromination with N-bromosuccinimide in chloroform at elevated temperature, particularly at 60° C., or by using other conditions known in the literature.

The saponification of the ester of general formula BC by methods well known to the ones skilled in the art—using e.g. aqueous LiOH, NaOH or KOH in tetrahydrofuran/ethanol or another suitable solvent at temperatures between 0° C. and the reflux temperature of the solvent employed—leads to the acid of general formula BD.

Scheme 2

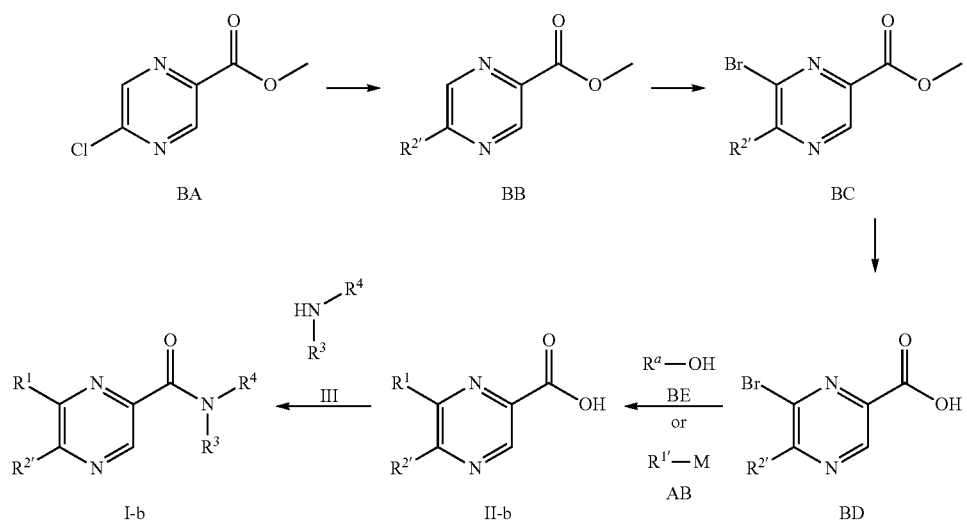

If one of the starting materials, compounds of formula III, contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, 3$^{rd}$ edition) can be introduced before the critical step applying methods well known in the art. Such protecting groups can be removed at a later stage of the synthesis using standard methods known in the art.

If one or more compounds of formula III contain chiral centers, pyridines of formula I-a can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Compounds BD can be transformed to compounds II-b for compounds where $R^1$ is cycloalkylalkoxy ($R^a$ is cycloalkylalkyl) by reaction with a suitably substituted primary or secondary alcohol BE in the presence of a base, for example potassium hydroxide, with or without an inert solvent, for example DMSO, at temperatures ranging from room temperature to the reflux temperature of the solvent, particularly at room temperature.

Alternatively, compound BD can be converted to compounds II-b for compounds where $R^1$ is halophenyl ($R^{1'}$ is halophenyl) by coupling a suitably substituted aryl-metal species of formula AB, particularly an arylboronic acid or arylboronic acid ester in the presence of a suitable catalyst and more particularly palladium(II)chloride-dppf (1,1'-bis (diphenylphosphino)-ferrocene) complexes and a base, particularly potassium carbonate in an inert solvent such as dimethylformamide.

Compound II-b can be further elaborated to compound I-b by coupling a compound of formula II-b with an amine of the formula III by amide coupling methods known in the art, as for example with the help of an amide coupling agent under basic conditions. For example coupling reagents like N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU), and O-benzotriazole-N,N,N',N'-tetramethyl-uronium-hexafluoro-phosphate (HBTU) can be employed to affect such transformation. A convenient method is to use for example O-benzotriazole-N,N,N',N'-tetramethyl-uronium-hexafluoro-phosphate (HBTU) and a base, for example N-ethyl-N-isopropylpropan-2-amine (DIEA) in an inert solvent such as for example dimethylformamide at room temperature. Alternative methods known in the art may commence by preparing the acid chloride from II-b and coupling with an amine of formula III in the presence of a suitable base.

Amines III are either commercially available, described in the literature, can be synthesized by a person skilled in the art or obtained as described in the experimental part.

If one of the starting materials, compounds of formulae BE or III, contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, 3$^{rd}$ edition) can be introduced before the critical step applying methods well known in the art. Such protecting groups can be removed at a later stage of the synthesis using standard methods known in the art.

If one or more compounds of formulae BE or III contain chiral centers, pyridines of formula I-b can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 3, compound AA (3,5-dibromo-2-pyrazinamine, CAN 24241-18-7) can be used as starting material for the synthesis of compounds I-c where $R^1$ is cycloalkylalkoxy ($R^{1''}$ is cycloalkylalkoxy) and $R^2$ is cycloalkyl ($R^{2''}$ is cycloalkyl).

Compound AA can be transformed to compounds CB for compounds where $R^1$ is cycloalkylalkoxy ($R^{1''}$ is cycloalkylalkoxy and $R^a$ is cycloalkylalkyl) by reaction with a suitably substituted primary or secondary alcohol BE in the presence of a base, for example sodium hydride, with or without an inert solvent, for example DMF, at temperatures ranging from room temperature to the reflux temperature of the solvent, particularly at room temperature.

The Boc-protection of compounds of general formula CB by methods well known to the ones skilled in the art—using e.g. di-tert-butyl dicarbonate in an inert solvent, particularly dichloromethane in the presence of a catalytic amount of base, particularly dimethylaminopyridine—leads to compounds of general formula CC if an excess of di-tert-butyl dicarbonate is employed in the reaction.

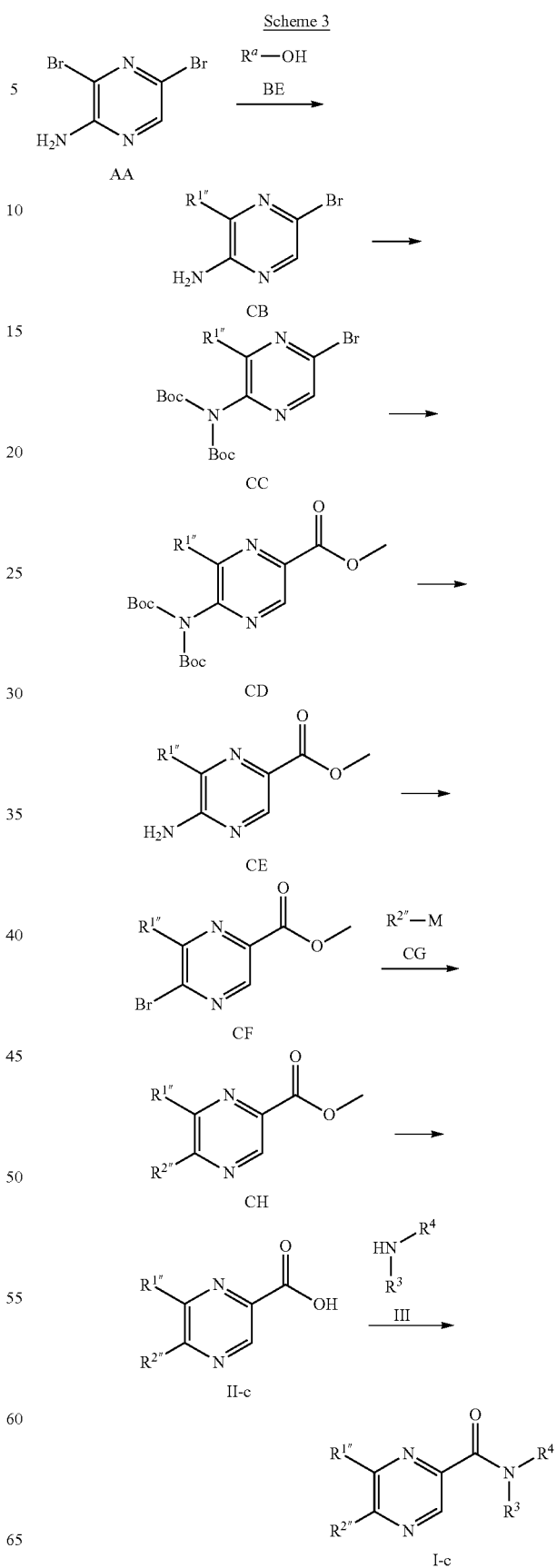

Scheme 3

Compounds of the general formula CD can be obtained from compounds of the general formula CC by palladium (II), particularly palladium(II) acetate catalyzed carbonylation in the presence of a suitable base such as a tertiary amine base, particularly triethylamine in a suitable solvent such as an alcohol, particularly methanol.

The solvolysis of boc-protected compounds of general formula CD by methods well known to the ones skilled in the art—using e.g. a protic solvent, particularly methanol at elevated temperatures, particularly reflux temperature—leads to compounds of general formula CE.

Compounds of the general formula CF can be obtained from compounds of the general formula CE by reaction with nitrosating agents such as a metal nitrite or an organic nitrite more particularly tert-butyl nitrite, in the presence of a bromide source such as hydrobromic acid or more particularly trimethylbromosilane in a suitable solvent such as halogenated hydrocarbons more particularly dibromomethane.

Compounds CH where $R^2$ is cycloalkyl ($R^{2''}$ is cycloalkyl) can be prepared from CF by coupling a suitably substituted cycloalkyl or cycloalkenyl metal species CG particularly a cyclopropylboronic acid or cyclopropyltrifluoro-borate salt with CF in the presence of a suitable catalyst, particularly a palladium catalyst like palladium(II)acetate in the presence of cyclohexylphosphine in an inert solvent such as toluene at room temperature up to the reflux temperature of the solvent in the presence of a suitable base, like potassium phosphate. In cases where the practitioner skilled in the art chooses to couple with a cycloalkenyl metal species, like cycloalkenylboronic acid esters, compounds CH will be obtained only after an additional hydrogenation step, for example by hydrogenation with hydrogen gas in the presence of a palladium catalyst, for example palladium on charcoal, in an inert solvent, for example ethanol, at suitable temperatures and pressures, particularly at ambient temperature and pressure.

The saponification of the ester of general formula CH by methods well known to the ones skilled in the art—using e.g. aqueous LiOH, NaOH or KOH in tetrahydrofuran/ethanol or another suitable solvent at temperatures between 0° C. and the reflux temperature of the solvent employed—leads to the acid of general formula II-c.

Compound II-c can be further elaborated to compound I-c by coupling a compound of formula II-c with an amine of the formula III by amide coupling methods known in the art, as for example with the help of an amide coupling agent under basic conditions. For example coupling reagents like N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU), and O-benzotriazole-N,N,N',N'-tetramethyl-uronium-hexafluoro-phosphate (HBTU) can be employed to affect such transformation. A convenient method is to use for example O-benzotriazole-N,N,N',N'-tetramethyl-uronium-hexafluoro-phosphate (HBTU) and a base, for example N-ethyl-N-isopropylpropan-2-amine (DIEA) in an inert solvent such as for example dimethylformamide at room temperature. Alternative methods known in the art may commence by preparing the acid chloride from II-c and coupling with an amine of formula III in the presence of a suitable base.

Amines III are either commercially available, described in the literature, can be synthesized by a person skilled in the art or obtained as described in the experimental part.

If one of the starting materials, compounds of formulae BE, CG or III, contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, $3^{rd}$ edition) can be introduced before the critical step applying methods well known in the art. Such protecting groups can be removed at a later stage of the synthesis using standard methods known in the art.

If one or more compounds of formulae BE, CG or III contain chiral centers, pyridines of formula I-b can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

The invention further relates to a process for the preparation of a compound of formula (I) comprising the reaction of a compound of formula (A)

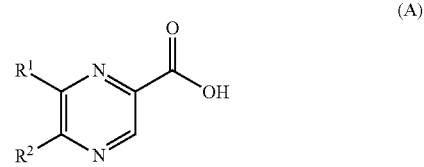

(A)

with a compound of formula $NHR^3R^4$, an amide bond forming coupling agent and a base, wherein $R^1$ to $R^4$ are as defined above.

Examples of amide bond forming coupling agents are N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) and O-benzotriazole-N,N,N',N'-tetramethyl-uronium-hexafluoro-phosphate (HBTU).

Examples of suitable bases are tertiary amine bases like triethylamine, N-methylmorpholine, N,N-diisopropylethylamine or 4-(dimethylamino)-pyridine.

The reaction temperature is for example room temperature.

A convenient method is to use for example HBTU and a base, for example N-methylmorpholine in an inert solvent such as for example dimethylformamide at room temperature.

The invention further relates to a compound of formula (I) for use as therapeutically active substance.

The invention further relates to a pharmaceutical composition comprising a compound of formula (I) and a therapeutically inert carrier.

The use of a compound of formula (I) for the treatment or prophylaxis of pain, in particular chronic pain, atherosclerosis, regulation of bone mass, inflammation, ischemia, reperfusion injury, systemic fibrosis, liver fibrosis, lung fibrosis, kidney fibrosis, chronic allograft nephropathy, congestive heart failure, myocardial infarction, systemic sclerosis, glomerulonephropathy, thermal injury, burning, hypertrophic scars, keloids, gingivitis pyrexia, liver cirrhosis or tumors is another object of the invention.

The use of a compound of formula (I) for the preparation of a medicament for the treatment or prophylaxis of chronic pain, in particular chronic pain, atherosclerosis, regulation of bone mass, inflammation, ischemia, reperfusion injury, systemic fibrosis, liver fibrosis, lung fibrosis, kidney fibrosis, chronic allograft nephropathy, congestive heart failure, myocardial infarction, systemic sclerosis, glomerulonephropathy, thermal injury, burning, hypertrophic scars, keloids, gingivitis pyrexia, liver cirrhosis or tumors is a further object of the invention.

The invention also relates to a compound of formula (I) for the treatment or prophylaxis of pain, in particular chronic pain, atherosclerosis, regulation of bone mass, inflammation, ischemia, reperfusion injury, systemic fibrosis, liver fibrosis, lung fibrosis, kidney fibrosis, chronic allograft nephropathy, congestive heart failure, myocardial infarction, systemic sclerosis, glomerulonephropathy, thermal injury, burning, hypertrophic scars, keloids, gingivitis pyrexia, liver cirrhosis or tumors.

The invention particularly relates to a compound of formula (I) for the treatment or prophylaxis of ischemia, reperfusion injury, liver fibrosis or kidney fibrosis, in particular ischemia or reperfusion injury.

The invention is further directed to a compound of formula (I), when manufactured according to a process according to the invention.

A method for the treatment or prophylaxis of pain, in particular chronic pain, atherosclerosis, regulation of bone mass, inflammation, ischemia, reperfusion injury, systemic fibrosis, liver fibrosis, lung fibrosis, kidney fibrosis, chronic allograft nephropathy, congestive heart failure, myocardial infarction, systemic sclerosis, glomerulonephropathy, thermal injury, burning, hypertrophic scars, keloids, gingivitis pyrexia, liver cirrhosis or tumors, which method comprises administering an effective amount of a compound of formula (I) is also an object of the invention.

Another embodiment of the invention provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The invention will now be illustrated by the following examples which have no limiting character.

EXAMPLES

Abbreviations
MS=mass spectrometry; EI=electron ionization; ESI=electrospray; NMR data are reported in parts per million (δ) relative to internal tetramethylsilane and are referenced to the deuterium lock signal from the sample solvent ($d_6$-DMSO unless otherwise stated); coupling constants (J) are in Hertz, mp=melting point; bp=boiling point; DIEA=N-ethyl-N-isopropylpropan-2-amine; DBU=1,8-Diazabicyclo[5.4.0]undec-7-ene; DMF=dimethylformamide; DMSO=dimethylsulfoxide; dppf=1,1'-bis(diphenylphosphino)ferrocene; HATU=2-(3H-[1,2,3]triazolo[4,5-b]pyridin-3-yl)-1,1,3,3-tetramethylisouronium hexafluorophosphate(V); HBTU=O-benzotriazole-N,N,N',N'-tetramethyl-uronium-hexafluorophosphate; HPLC=LC=high performance liquid chromatography; m-CPBA=meta-chloroperoxybenzoic acid; Rt=retention time; TBTU=O-(benzotriazol-1-yl)-N,N,N',N'-tetramethyl-uronium-tetrafluoroborate; TEMPO=2,2,6,6-tetra-methylpiperidine 1-oxyl radical; TBME=methyl tert-butylether, THF=tetrahydrofuran; TFA=trifluoroacetic acid; tlc=thin layer chromatography; CAN=CAS Registry Number.

Example 1

6-(3-Chloro-phenyl)-5-cyclopropyl-pyrazine-2-carboxylic acid [1-methyl-1-(5-methyl-[1,2,4]oxadiazol-3-yl)-ethyl]amide a) 5-Bromo-3-(3-chloro-phenyl)-pyrazin-2-ylamine

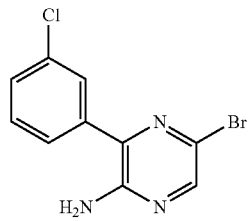 [SMILES: Nc1ncc(Br)nc1-c1cccc(Cl)c1]

3,5-Dibromo-2-pyrazinamine (CAN 24241-18-7; 45.1 g, 0.178 mol) was dissolved in dimethoxyethane (450 mL). To this solution was added 4-chlorophenylboronic acid (27.8 g, 0.178 mol), sodium carbonate (37.7 g, 0.356 mol) and tetrakis (triphenylphosphine)-palladium(0) (10.28 g, 0.009 mol). The mixture was stirred over night at 110° C. and afterwards cooled to room temperature. Citric acid solution (10%, 200 mL) was added and the mixture was extracted with ethyl acetate. The organic phases were washed successively with sodium bicarbonate solution (10%, 300 mL) and brine (200 mL); combined, treated with charcoal (3.8 g), dried with Na₂SO₄ and, after filtration concentrated. The title compound (30.7 g, 61%) was isolated by crystallization from the concentrated solution; MS (EI): 285 (M+H).

b) 5-Amino-6-(3-chloro-phenyl)-pyrazine-2-carboxylic acid methyl ester

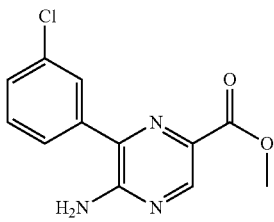 [SMILES: COC(=O)c1cnc(N)c(-c2cccc(Cl)c2)n1]

To a solution of 5-bromo-3-(3-chloro-phenyl)-pyrazin-2-ylamine (5.1 g, 18 mmol) in methanol (30 mL) was added PdCl₂.dppf.CH₂Cl₂ (0.51 g, 0.6 mmol) and triethylamine (5 mL) and the mixture was stirred under an atmosphere of 70 bar carbon monoxide at 110° C. for 20 hours. After expansion and cooling citric acid solution (10%, 150 mL) and ethyl acetate (300 mL) were added and solids were removed by filtration. The organic phase was separated, stirred for 1 hour with charcoal, dried with Na₂SO₄ and, after filtration concentrated. The title compound (1.36 g, 27%) was isolated by crystallization from the concentrated solution; MS (EI): 263.9 (M+H).

c) 5-Bromo-6-(3-chloro-phenyl)-pyrazine-2-carboxylic acid methyl ester

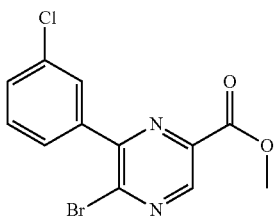 [SMILES: COC(=O)c1cnc(Br)c(-c2cccc(Cl)c2)n1]

5-Amino-6-(3-chloro-phenyl)-pyrazine-2-carboxylic acid methyl ester (18.1 g, 61 mmol) was suspended in dibromomethane (190 mL). To this suspension was added isopentyl nitrite (8.8 g, 73 mmol) and the mixture was stirred at room temperature for 15 minutes. Bromotrimethylsilane (11.6 g, 73 mmol) was added drop by drop (exothermic reaction) and the resulting solution was stirred at room temperature for 1 hour. The mixture was partitioned between water (190 mL) and ethyl acetate and the organic phase was dried with MgSO₄, filtered and concentrated in vacuo. The crude material was purified by chromatography (silica gel, 550 g, 1:1 dichloromethane in n-heptane) to give the desired product (11.3 g, 54%) as yellow solid; MS (EI): 328.5 (M+H).

d) 5-Bromo-6-(3-chloro-phenyl)-pyrazine-2-carboxylic acid

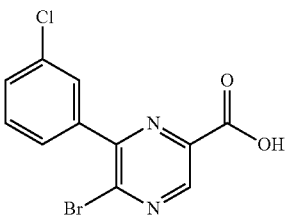 [SMILES: O=C(O)c1cnc(Br)c(-c2cccc(Cl)c2)n1]

To a solution of 5-bromo-6-(3-chloro-phenyl)-pyrazine-2-carboxylic acid methyl ester (11.3 g, 35 mmol) in THF (170 mL) was added 1M of lithium hydroxide in water (40 mL) and the mixture was stirred at ambient temperature for 1.5 hours. Citric acid solution (10%, 90 mL) was added and the organic layer was separated and concentrated in vacuo. The residue was recrystallized from n-heptane to give the title compound (12.0 g, quant.) as white crystalline solid; MS (ESI): 312.5 (M−H).

e) 5-Bromo-6-(3-chloro-phenyl)-pyrazine-2-carboxylic acid [1-methyl-1-(5-methyl-[1,2,4]oxadiazol-3-yl)-ethyl]-amide

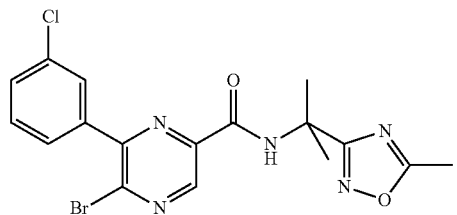 [SMILES: Cc1nc(C(C)(C)NC(=O)c2cnc(Br)c(-c3cccc(Cl)c3)n2)no1]

5-Bromo-6-(3-chloro-phenyl)-pyrazine-2-carboxylic acid (0.200 g, 638 µmol) was suspended in dichloromethane (1 mL) and 1-chloro-N,N,2-trimethylpropenylamine (98.0 mg, 97.0 µl, 734 µmol) was added dropwise at room temperature. After 30 min stirring the brown solution was added drop by drop to a solution of α,α,5-trimethyl-1,2,4-oxadiazole-3-methanamine hydrochloride (CAN 1240526-27-5; 142 mg, 797 µmol) and ethyldiisopropylamine (206 mg, 264 µl, 1.59 mmol) in DMF (1 mL) and the reaction mixture was stirred at room temperature for 30 minutes. The mixture was extracted with ethyl acetate and 1M citric acid solution; the organic phase was dried with MgSO4; filtered and concentrated in vacuo. The crude material was purified by flash chromatography (silica gel, 20 g, 5% to 50% ethyl acetate in n-heptane) to give the desired product (126 mg, 45%) as white foam; MS (EI): 436.0 (M+H).

f) 6-(3-Chloro-phenyl)-5-cyclopropyl-pyrazine-2-carboxylic acid [1-methyl-1-(5-methyl-[1,2,4]oxadiazol-3-yl)-ethyl]-amide

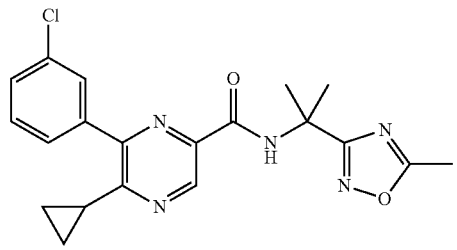 [SMILES: Cc1nc(C(C)(C)NC(=O)c2cnc(C3CC3)c(-c3cccc(Cl)c3)n2)no1]

5-Bromo-6-(3-chloro-phenyl)-pyrazine-2-carboxylic acid [1-methyl-1-(5-methyl-[1,2,4]oxadiazol-3-yl)-ethyl]-amide (0.100 g, 229 μmol), and tetrakis-(triphenyl-phosphine)palladium (13.2 mg, 11.4 μmol) were dissolved in THF (2.5 mL). Cyclopropylzinc(II)bromide (0.5M in THF, 1800 μl, 900 μmol) was added drop by drop at 0° C. and the reaction mixture was stirred at room temperature for 1.5 hours and at reflux temperature overnight. The mixture was partitioned between water and ethyl acetate and the organic phase was dried with MgSO$_4$, filtered and concentrated in vacuo. The crude material was purified by flash chromatography (silica gel, 10 g, 5% to 40% ethyl acetate in n-heptane) to give the desired product (24 mg, 26%) as white solid; MS (EI): 398.2 (M+H). As side product 11 mg of 6-(3-chloro-phenyl)-5-cyclopropyl-pyrazine-2-carboxylic acid (cyano-dimethyl-methyl)-amide (Example 2) was isolated.

Example 2

6-(3-Chloro-phenyl)-5-cyclopropyl-pyrazine-2-carboxylic acid (cyano-dimethyl-methyl)-amide

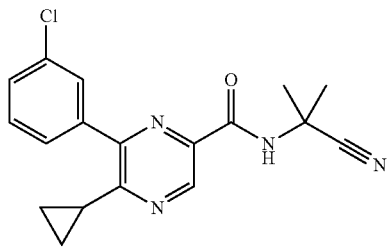 [SMILES: CC(C)(C#N)NC(=O)c1cnc(C2CC2)c(-c2cccc(Cl)c2)n1]

The title compound was isolated as side product during preparation of Example 1 (11 mg, 14%) as white solid; MS (EI): 341.1 (M+H).

Example 3

6-(3-Chloro-phenyl)-5-cyclopropyl-pyrazine-2-carboxylic acid [1-(5-methyl-[1,2,4]oxadiazol-3-yl)-cyclobutyl]-amide a) 6-(3-Chloro-phenyl)-5-cyclopropyl-pyrazine-2-carboxylic acid

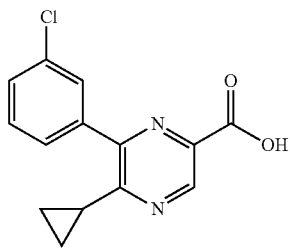 [SMILES: O=C(O)c1cnc(C2CC2)c(-c2cccc(Cl)c2)n1]

5-Bromo-6-(3-chloro-phenyl)-pyrazine-2-carboxylic acid (Example 1d, 0.200 g, 638 mmol), and [1,3-bis(2,6-diisopropylphenyl)imidazol-2-ylidene](3-chloropyridyl)-palladium (II) dichloride (22.2 mg, 31.9 μmol) were dissolved in THF (5 mL) and 1,3-dimethyl-2-imidazolidinone (1 mL). Cyclopropylzinc(II)bromide (0.5 M in THF, 3.83 mL, 1.91 mmol) was added drop by drop at room temperature and the reaction mixture was stirred at reflux temperature for 2 hours. More cyclopropylzinc(II)bromide (0.5 M in THF, 1.91 mL, 957 μmol) was added and stirring at reflux temperature continued for another 2 hours. The mixture was partitioned between water and ethyl acetate and the organic phase was dried with MgSO$_4$, filtered and concentrated in vacuo. The crude material was purified by reverse phase chromatography to give the desired product (52 mg, 30%) as light yellow oil; MS (ESI): 273.2 (M−H).

b) 6-(3-Chloro-phenyl)-5-cyclopropyl-pyrazine-2-carboxylic acid [1-(5-methyl-[1,2,4]oxadiazol-3-yl)-cyclobutyl]-amide

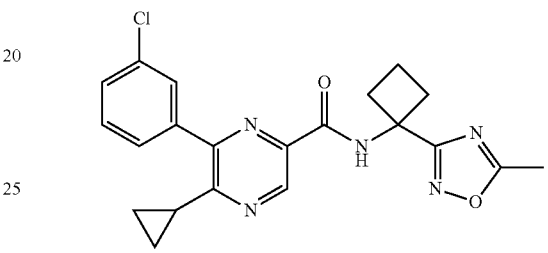

The title compound was synthesized in analogy to Example 1e, using 6-(3-chloro-phenyl)-5-cyclopropyl-pyrazine-2-carboxylic acid and 1-(5-methyl-1,2,4-oxadiazol-3-yl)-cyclobutanamine hydrochloride (CAN 1170897-128-5) as starting materials, and isolated (43 mg, 58%) as white solid; MS (EI): 410.2 (M+H).

Example 4

6-(3-Chloro-phenyl)-5-(3,3-difluoro-azetidin-1-yl)-pyrazine-2-carboxylic acid [1-methyl-1-(5-methyl-[1,2,4]oxadiazol-3-yl)-ethyl]-amide

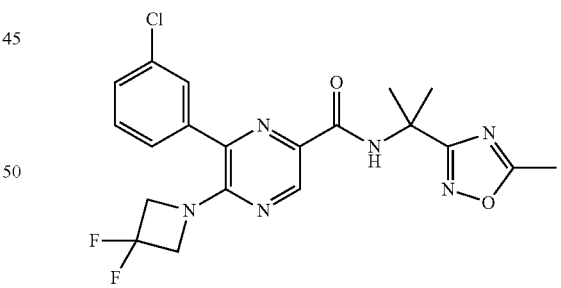

5-Bromo-6-(3-chloro-phenyl)-pyrazine-2-carboxylic acid [1-methyl-1-(5-methyl-[1,2,4]oxadiazol-3-yl)-ethyl]-amide (Example 1e, 0.075 g, 172 μmol) was added to a solution containing 3,3-difluoroazetidine hydrochloride (77.9 mg, 601 μmol) and DBU (91.5 mg, 89.8 μl, 601 μmol) in DMSO (1 mL). The reaction mixture was stirred at room temperature for 2 hours and extracted with ethyl acetate and 10% citric acid. The organic phase was dried with MgSO$_4$, filtered and concentrated in vacuo. The crude material was purified by reverse phase chromatography to give the desired product (8 mg, 10%) as colorless oil; MS (ESI): 449.1 (M+H).

Example 5

5-Azetidin-1-yl-6-(3-chloro-phenyl)-pyrazine-2-carboxylic acid [1-methyl-1-(5-methyl-[1,2,4]oxadiazol-3-yl)-ethyl]-amide

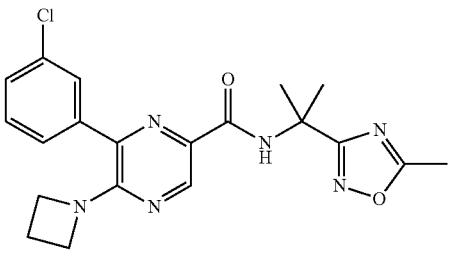 [SMILES: Cc1nc(C(C)(C)NC(=O)c2cnc(N3CCC3)c(-c3cccc(Cl)c3)n2)no1]

The title compound was synthesized in analogy to Example 4, using 5-bromo-6-(3-chloro-phenyl)-pyrazine-2-carboxylic acid [1-methyl-1-(5-methyl-[1,2,4]oxadiazol-3-yl)-ethyl]-amide (Example 1e) and azetidine as starting materials, and isolated (29 mg, 41%) as light yellow oil; MS (EI): 413.2 (M+H).

Example 6

6-(3-Chloro-phenyl)-5-cyclopropyl-pyrazine-2-carboxylic acid (1-methyl-1-thiazol-2-yl-ethyl)-amide

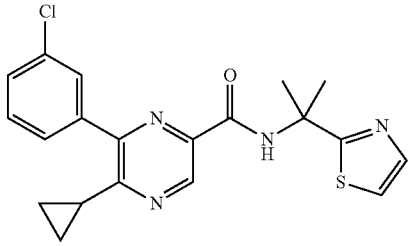 [SMILES: CC(C)(NC(=O)c1cnc(C2CC2)c(-c2cccc(Cl)c2)n1)c1nccs1]

6-(3-Chloro-phenyl)-5-cyclopropyl-pyrazine-2-carboxylic acid triethylamine salt (1:1) (Example 3a, 0.077 g, 205 μmol) was suspended in DMF (770 μL). TBTU (78.9 mg, 246 mmol), DIEA (106 mg, 136 μl) and α,α-dimethyl-2-thiazolemethanamine hydrochloride (43.9 mg, 246 μmol) were added and the reaction mixture was stirred at room temperature for 2 hours. The mixture was extracted with ethyl acetate and water; the organic phase was dried over MgSO$_4$, filtered and concentrated in vacuo. The crude material was purified by flash chromatography (silica gel, 10 g, 5% to 50% ethyl acetate in n-heptane) to give the desired product (48 mg, 59%) as white solid; LC-MS (UV peak area, ESI) 94%, 399.1042 (M+H).

Example 7

6-(3-Chloro-phenyl)-5-cyclopropyl-pyrazine-2-carboxylic acid piperidin-1-ylamide

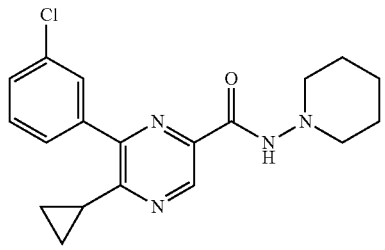 [SMILES: O=C(NN1CCCCC1)c1cnc(C2CC2)c(-c2cccc(Cl)c2)n1]

The title compound was synthesized in analogy to Example 6, using 6-(3-chloro-phenyl)-5-cyclopropyl-pyrazine-2-carboxylic acid (Example 3a) and 1-amino-piperidine as starting materials, and isolated (29 mg, 40%) as white solid; LC-MS (UV peak area, ESI) 100%, 357.1485 (M+H).

Example 8

6-Cyclopropylmethoxy-5-(3,3-difluoro-azetidin-1-yl)-pyrazine-2-carboxylic acid ((S)-2,2-dimethyl-1-methylcarbamoyl-propyl)-amide a) 5-(3,3-Difluoro-azetidin-1-yl)-pyrazine-2-carboxylic acid methyl ester

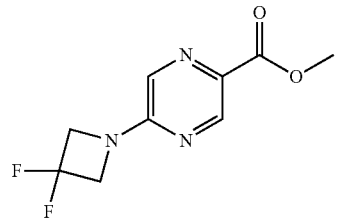 [SMILES: COC(=O)c1cnc(N2CC(F)(F)C2)cn1]

5-Chloro-pyrazine-2-carboxylic acid methyl ester (CAN 33332-25-1; 15 g, 86.92 mmol) was dissolved in dioxane (100 mL). To this solution was added 3,3-difluoroazetidine hydrochloride (CAN 288315-03-7; 13.51 g, 104.31 mmol), and triethyl amine (31.3 mL, 226 mmol). The mixture was stirred 22 hours at 45° C. and afterwards cooled to room temperature. Brine solution (100 mL) was added and the mixture was extracted with ethyl acetate. The organic phases were washed successively with sodium bicarbonate solution (10%, 300 mL) and brine (200 mL); dried with Na$_2$SO$_4$ and filtered and concentrated in vacuo. The crude material was purified by flash chromatography (silica gel, 200 g, 30% to 50% ethyl acetate in hexane) to give the desired product (15 g, 75.3%) as white solid; LC-MS (UV peak area, ESI) 98.6%, 230.4 (M+H).

b) 6-Bromo-5-(3,3-difluoro-azetidin-1-yl)-pyrazine-2-carboxylic acid methyl ester

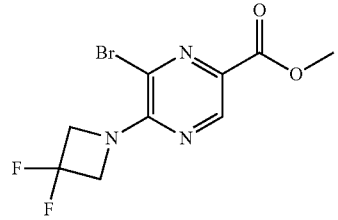 [SMILES: COC(=O)c1cnc(N2CC(F)(F)C2)c(Br)n1]

To a solution of 5-(3,3-difluoro-azetidin-1-yl)-pyrazine-2-carboxylic acid methyl ester (16.5 g, 72.05 mmol) in chloroform (200 mL) was added N-bromosuccinimide (25.64 g, 151.34 mmol) portion wise at 60° C. and the mixture was stirred at 60° C. for 20 hours. After cooling, water (400 mL) was added and the organic phase was separated, the organic phase was washed successively with water (200 mL), brine (200 mL); dried with Na$_2$SO$_4$, filtered and concentrated in vacuo. The crude material was purified by flash chromatography (silica gel, 200 g, 50% ethyl acetate in hexane) to give the desired product (17 g, 77.2%) as light yellow solid; LC-MS (UV peak area, ESI) 97.84%, 308.0 (M+H).

c) 6-Bromo-5-(3,3-difluoro-azetidin-1-yl)-pyrazine-2-carboxylic acid

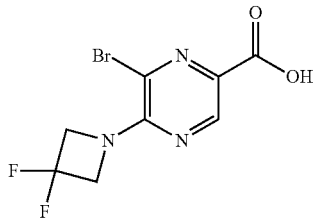 [SMILES: O=C(O)c1cnc(N2CC(F)(F)C2)c(Br)n1]

To a solution of 6-bromo-5-(3,3-difluoro-azetidin-1-yl)-pyrazine-2-carboxylic acid methyl ester (6.0 g, 19.48 mmol) in THF (20 mL) and H₂O (10 mL) was added lithium hydroxide (1.06 g, 25.32 mmol) and the mixture was stirred at ambient temperature for 5 hours. Solvent was concentrated in vacuo and residue was diluted with H₂O (30 mL). The aqueous phase was acidified with hydrochloric acid (1M, pH~2-3) and the solid was separated. The solid was triturated with toluene (25 mL) and dried in vacuo to give the title compound (4.0 g, 70.17%) as white crystalline solid; LC-MS (UV peak area, ESI) 100%, 294.2 (M+H).

d) 6-Cyclopropylmethoxy-5-(3,3-difluoro-azetidin-1-yl)-pyrazine-2-carboxylic acid

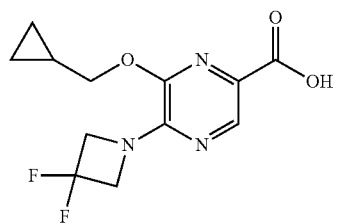 [SMILES: O=C(O)c1cnc(N2CC(F)(F)C2)c(OCC2CC2)n1]

To a solution of cyclopropyl-methanol (4.96 mL, 61.21 mmol) in dry dimethyl sulfoxide (90 mL) was added potassium hydroxide (5.89 g, 107.12 mmol) portion wise at ambient temperature. To this mixture was added a solution of 6-bromo-5-(3,3-difluoro-azetidin-1-yl)-pyrazine-2-carboxylic acid (9.0 g, 30.61 mmol) in dimethyl sulfoxide (10 mL). The reaction mixture was stirred at ambient temperature for 3 hours. Water (100 mL) was added and the aqueous was acidified with aqueous hydrochloric acid (10%, pH~3-4), and the solid was filtered. The solid was triturated with toluene (50 mL) and dried in vacuo to give the title compound (8.0 g, 91.64%) as white crystalline solid; LC-MS (UV peak area, ESI) 100%, 286.2 (M+H).

e) 6-Cyclopropylmethoxy-5-(3,3-difluoro-azetidin-1-yl)-pyrazine-2-carboxylic acid ((S)-2,2-dimethyl-1-methylcarbamoyl-propyl)-amide

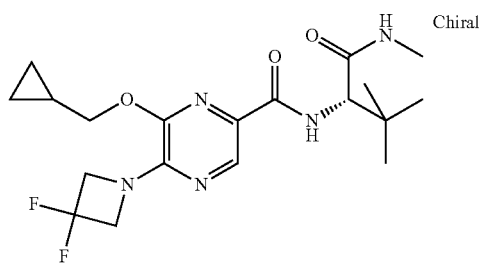 [SMILES: CNC(=O)[C@@H](NC(=O)c1cnc(N2CC(F)(F)C2)c(OCC2CC2)n1)C(C)(C)C]

6-Cyclopropylmethoxy-5-(3,3-difluoro-azetidin-1-yl)-pyrazine-2-carboxylic acid (Example 8d, 0.1 g, 35 mmol) was suspended in DMF (3 mL). HBTU (266.14 mg, 0.7 mmol), DIEA (0.31 mL, 1.75 mmol) and (S)-2-amino-3,3,N-trimethyl-butyramide (CAN 89226-12-0, 52.82 mg, 0.42 mmol) were added and the reaction mixture was stirred at ambient temperature for 12 hours. The mixture was extracted with ethyl acetate and water; the organic phase was dried over Na₂SO₄, filtered and concentrated in vacuo. The crude material was purified by reverse phase preparative HPLC (Gemini-NX-C18, 5 μ, 30×100 mm/acetonitrile/0.1% ammonia in water) to give the desired product (15 mg, 10.39%) as white solid; LC-MS (UV peak area, ESI) 96.48%, 412.6 (M+H).

Example 9

6-Cyclopropylmethoxy-5-(3,3-difluoro-azetidin-1-yl)-pyrazine-2-carboxylic acid [1-(5-methyl-[1,2,4]oxadiazol-3-yl)-cyclobutyl]-amide

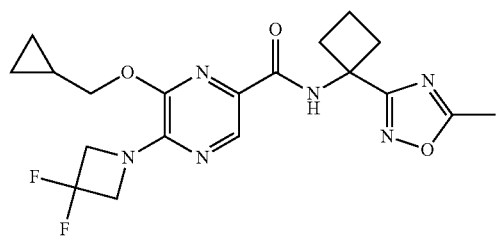 [SMILES: Cc1nc(C2(NC(=O)c3cnc(N4CC(F)(F)C4)c(OCC4CC4)n3)CCC2)no1]

The title compound was synthesized in analogy to Example 8e, using 6-cyclopropylmethoxy-5-(3,3-difluoro-azetidin-1-yl)-pyrazine-2-carboxylic acid (Example 8d, 100 mg, 0.35 mmol) and 1-(5-methyl-1,2,4-oxadiazol-3-yl)-cyclobutanamine (CAN 1170897-128-5, 64.42 mg, 0.42 mmol) as starting materials, and isolated (25 mg, 16.95%) as off white solid; LC-MS (UV peak area, ESI) 99.10%, 421.4 (M+H).

Example 10

5-Cyclopropyl-6-cyclopropylmethoxy-pyrazine-2-carboxylic acid (3-hydroxy-1,1-dimethyl-propyl)-amide a) 5-Bromo-3-cyclopropylmethoxy-pyrazin-2-ylamine

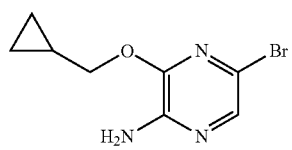

To a solution of cyclopropyl-methanol (16.47 mL, 205.62 mmol) in dimethyl sulfoxide (200 mL) was added sodium hydride (60% in oil, 4.93 g, 205.62 mmol) at 0° C. and the reaction mixture was stirred at 0° C. for 2 hours. To this suspension was added 3,5-dibromo-pyrazin-2-ylamine (20 g, 79.09 mmol) in dimethyl sulfoxide (40 mL) and the mixture was stirred at ambient temperature for 12 hours. The mixture was partitioned between water (300 mL) and ethyl acetate and the organic phase was dried with Na₂SO₄, filtered and concentrated in vacuo. The crude material was purified by chromatography (silica gel, 500 g, 10% ethyl acetate in hexane) to give the desired product (14 g, 72.52%) as yellow solid; LC-MS (UV peak area, ESI) 94.69%, 244.0 (M+H).

b) Di-tert-butyl[5-bromo-3-(cyclopropylmethoxy)pyrazin-2-yl]imidodicarbonate

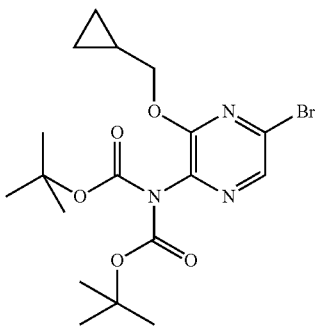 [SMILES: CC(C)(C)OC(=O)N(C(=O)OC(C)(C)C)c1ncc(Br)nc1OCC1CC1]

To a solution of 5-bromo-3-cyclopropylmethoxy-pyrazin-2-ylamine (30 g, 122.91 mmol) in dichloromethane (200 mL) were added di-tert-butyl dicarbonate (67.7 mL, 307.26 mmol) and 4-dimethylaminopyridine (1.49 g, 12.29 mmol). The reaction mixture was stirred at ambient temperature for 18 hours. The mixture was partitioned between water (300 mL) and dichloromethane and the organic phase was separated, washed with brine, dried with $Na_2SO_4$, filtered and concentrated in vacuo. The crude material was purified by chromatography (silica gel, 600 g, 5%-7% ethyl acetate in hexane) to give the desired product (45 g, 82.77%) as yellow oil; LC-MS (UV peak area, ESI) 94.69%, 445.0 (M+H).

c) Methyl 5-[bis(tert-butoxycarbonyl)amino]-6-(cyclopropylmethoxy)pyrazine-2-carboxylate

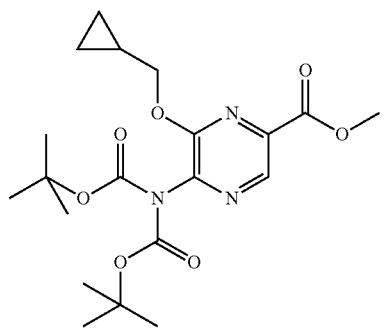 [SMILES: COC(=O)c1cnc(N(C(=O)OC(C)(C)C)C(=O)OC(C)(C)C)c(OCC2CC2)n1]

To a solution of di-tert-butyl[5-bromo-3-(cyclopropylmethoxy)pyrazin-2-yl]imido-dicarbonate (20 g, 45.05 mmol) in methanol (200 mL) was added $PdCl_2.dppf.CH_2Cl_2$ (4.04 g, 4.95 mmol) and triethylamine (9.5 mL, 67.57 mmol) and the mixture was stirred under an atmosphere of 32 bar carbon monoxide at 80° C. for 5 hours. After expansion and cooling, the solid was removed by filtration. The organic phase was separated, washed with brine (300 mL), dried with $Na_2SO_4$, filtered and concentrated in vacuo. The crude material was purified by chromatography (Combi-Flash, 120 g, 15%-20% ethyl acetate in hexane) to give the desired product (14 g, 73.68%) as yellow semi-solid; LC-MS (UV peak area, ESI) 96.14%, 424.4 (M+H).

d) 5-Amino-6-cyclopropylmethoxy-pyrazine-2-carboxylic acid methyl ester

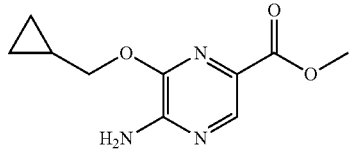 [SMILES: COC(=O)c1cnc(N)c(OCC2CC2)n1]

Methyl 5-[bis(tert-butoxycarbonyl)amino]-6-(cyclopropylmethoxy)pyrazine-2-carboxylate (15 g, 35.46 mmol) was suspended in methanol (150 mL) and water (225 mL) and the mixture was heated at 100° C. for 12 hours. After cooling, white solid was formed, filtered and dried in vacuo to give the title compound (5.7 g, 72.15%) as off white solid; LC-MS (UV peak area, ESI) 99.68%, 224.2 (M+H).

e) 5-Bromo-6-cyclopropylmethoxy-pyrazine-2-carboxylic acid methyl ester

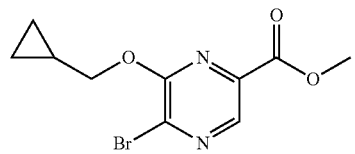 [SMILES: COC(=O)c1cnc(Br)c(OCC2CC2)n1]

5-Amino-6-cyclopropylmethoxy-pyrazine-2-carboxylic acid methyl ester (10 g, 44.84 mmol) was suspended in dibromomethane (150 mL). To this suspension were added trimethylsilyl bromide (14.8 mL, 112.11 mmol) followed by tert-butyl nitrite (57.5 mL, 448.43 mmol) at 0° C. and the mixture was stirred at that temperature for 3 hours. The mixture was partitioned between water (190 mL) and ethyl acetate and the organic phase was washed with brine (200 mL), dried with $Na_2SO_4$, filtered and concentrated in vacuo. The crude material was purified by chromatography (Combi-Flash, 80 g, 20% ethyl acetate in hexane) to give the desired product (6.3 g, 46.6%) as white solid; LC-MS (UV peak area, ESI) 90.68%, 287.2 (M+H).

f) 5-Cyclopropyl-6-cyclopropylmethoxy-pyrazine-2-carboxylic acid methyl ester

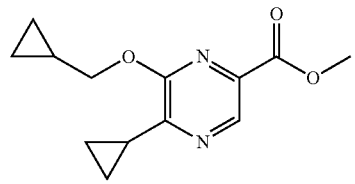 [SMILES: COC(=O)c1cnc(C2CC2)c(OCC2CC2)n1]

5-Bromo-6-cyclopropylmethoxy-pyrazine-2-carboxylic acid methyl ester (5 g, 17.42 mmol), potassium phosphate tribasic (12.9 g, 60.98 mmol) and palladium(II)acetate (389 mg, 1.74 µmol) were dissolved in toluene (45 mL) and water (5 mL) and the reaction mixture was degassed with argon for 15 minutes. Cyclopropylboronic acid (2.9 g, 34.84 mmol) and tricyclohexylphosphine (0.487 g, 1.74 mmol) were added and the reaction mixture was stirred at 60° C. for 16 hours. The mixture was partitioned between water and ethyl acetate and the organic phase was washed with brine (100 mL), dried with $Na_2SO_4$, filtered and concentrated in vacuo. The crude material was purified by chromatography (Combi-Flash, 80 g, 10%-15% ethyl acetate in hexane) to give the desired product (2.6 g, 60.11%) as white solid; LC-MS (UV peak area, ESI) 98.87%, 249.2 (M+H).

g) 5-Cyclopropyl-6-cyclopropylmethoxy-pyrazine-2-carboxylic acid

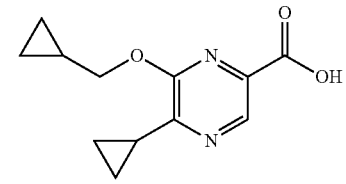 [SMILES: O=C(O)c1cnc(C2CC2)c(OCC2CC2)n1]

To a solution of 5-cyclopropyl-6-cyclopropylmethoxy-pyrazine-2-carboxylic acid methyl ester (7 g, 28.23 mmol) in THF (20 mL) and $H_2O$ (10 mL) was added lithium hydroxide (1.54 g, 26.69 mmol) and the mixture was stirred at ambient temperature for 4.5 hours. Solvent was concentrated in vacuo and residue was diluted with $H_2O$ (20 mL). The aqueous phase was acidified with hydrochloric acid (1M, pH~2-3) and the solid was separated. The solid was triturated with toluene (25 ml) and dried in vacuo to give the title compound (5.3 g, 86.6%) as white crystalline solid; LC-MS (UV peak area, ESI) 93.2%, 233.2 (M−H).

h) 5-Cyclopropyl-6-cyclopropylmethoxy-pyrazine-2-carboxylic acid (3-hydroxy-1,1-dimethyl-propyl)-amide

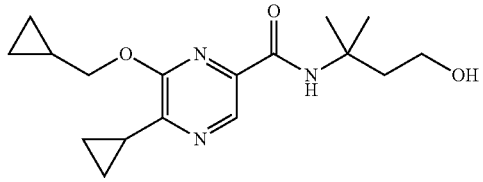 [SMILES: CC(C)(CCO)NC(=O)c1cnc(C2CC2)c(OCC2CC2)n1]

The title compound was synthesized in analogy to Example 8e, using 5-cyclopropyl-6-cyclopropylmethoxy-pyrazine-2-carboxylic acid (Example 10 g, 100 mg, 0.43 mmol) and 3-amino-3-methyl-1-butanol (CAN 42514-50-1; 58.46 mg, 0.51 mmol) as starting materials, and isolated (15 mg, 10.9%) as off white solid; LC-MS (UV peak area, ESI) 100%, 320.4 (M+H).

Example 11

5-Cyclopropyl-6-cyclopropylmethoxy-pyrazine-2-carboxylic acid (1-hydroxymethyl-cyclobutyl)-amide

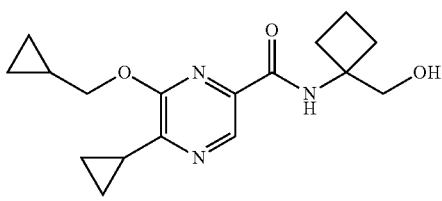 [SMILES: O=C(NC1(CO)CCC1)c1cnc(C2CC2)c(OCC2CC2)n1]

The title compound was synthesized in analogy to Example 8e, using 5-cyclopropyl-6-cyclopropylmethoxy-pyrazine-2-carboxylic acid (Example 10 g, 100 mg, 0.43 mmol) and 1-amino-cyclobutanemethanol (CAN 180205-34-9, 66.02 mg, 0.64 mmol) as starting materials, and isolated (50 mg, 36.86%) as off white solid; LC-MS (UV peak area, ESI) 97.56%, 318.4 (M+H).

Example 12

5-Cyclopropyl-6-cyclopropylmethoxy-pyrazine-2-carboxylic acid [1-(5-methyl-[1,2,4]oxadiazol-3-yl)-cyclobutyl]-amide

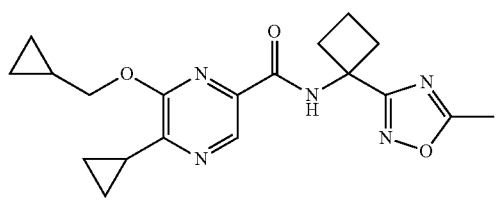 [SMILES: Cc1nc(C2(NC(=O)c3cnc(C4CC4)c(OCC4CC4)n3)CCC2)no1]

The title compound was synthesized in analogy to Example 8e, using 5-cyclopropyl-6-cyclopropylmethoxy-pyrazine-2-carboxylic acid (Example 10 g, 100 mg, 0.43 mmol) and 1-(5-methyl-1,2,4-oxadiazol-3-yl)-cyclobutanamine (CAN 1170897-128-5, 98.07 mg, 0.64 mmol) as start-ing materials, and isolated (50 mg, 31.67%) as off white solid; LC-MS (UV peak area, ESI) 99.91%, 370.0 (M+H).

Example 13

5-Cyclopropyl-6-cyclopropylmethoxy-pyrazine-2-carboxylic acid (1-hydroxymethyl-1-methyl-propyl)-amide

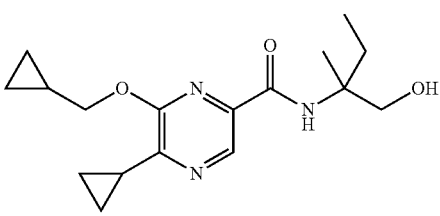 [SMILES: CCC(C)(CO)NC(=O)c1cnc(C2CC2)c(OCC2CC2)n1]

The title compound was synthesized in analogy to Example 8e, using 5-cyclopropyl-6-cyclopropylmethoxy-pyrazine-2-carboxylic acid (Example 10 g, 100 mg, 0.43 mmol) and 2-amino-2-methyl-1-butanol (CAN 10196-30-2, 64.74 mg, 0.64 mmol) as starting materials, and isolated (12 mg, 8.79%) as off white solid, LC-MS (UV peak area, ESI) 100%, 320.4 (M+H).

Example 14

5-Cyclopropyl-6-cyclopropylmethoxy-pyrazine-2-carboxylic acid ((S)-2,2-dimethyl-1-methylcarbamoyl-propyl)-amide

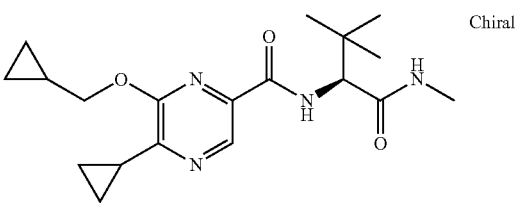 [SMILES: CNC(=O)[C@@H](NC(=O)c1cnc(C2CC2)c(OCC2CC2)n1)C(C)(C)C]

The title compound was synthesized in analogy to Example 8e, using 5-cyclopropyl-6-cyclopropylmethoxy-pyrazine-2-carboxylic acid (Example 10 g, 100 mg, 0.43 mmol) and (S)-2-amino-3,3,N-trimethyl-butyramide (CAN 89226-12-0, 106.7 mg, 0.64 mmol) as starting materials, and isolated (45 mg, 29.4%) as off white solid, LC-MS (UV peak area, ESI) 100%, 361.4 (M+H).

Example 15

5-Cyclopropyl-6-cyclopropylmethoxy-pyrazine-2-carboxylic acid ((S)-carbamoyl-phenyl-methyl)-amide

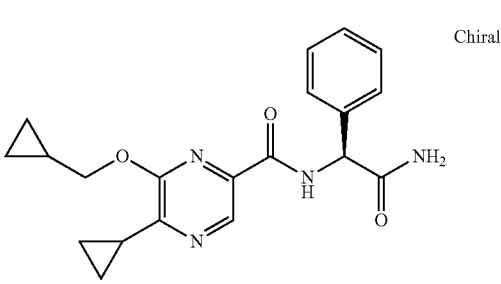 [SMILES: NC(=O)[C@@H](NC(=O)c1cnc(C2CC2)c(OCC2CC2)n1)c1ccccc1]

5-Cyclopropyl-6-cyclopropylmethoxy-pyrazine-2-carboxylic acid (Example 10 g, 100 mg, 0.43 mmol) was suspended in DMF (3 mL). TBTU (224.14 mg, 0.85 mmol), DIEA (0.31 mL, 2.24 mmol) and (αS)-α-amino-benzeneacetamide (CAN 6485-52-5, 51.2 mg, 0.51 mmol) were added and the reaction mixture was stirred at room temperature for 12 hours. The mixture was extracted with ethyl acetate and water; the organic phase was dried over Na₂SO4, filtered and concentrated in vacuo. The crude material was purified by reverse phase preparative HPLC (Xbridge-C18, 5 μ, 19×250 mm/acetonitrile/0.1% ammonia in water) to give the desired product (15 mg, 9.58%) as white solid; LC-MS (UV peak area, ESI) 93.20%, 367.4 (M+H).

Example 16

6-Cyclopropylmethoxy-5-(3,3-difluoro-azetidin-1-yl)-pyrazine-2-carboxylic acid ((S)-1-cyclopropylmethyl-2-hydroxy-2-methyl-propyl)-amide a) (S)-Methyl 2-(tert-butoxycarbonylamino)-3-cyclopropylpropanoate

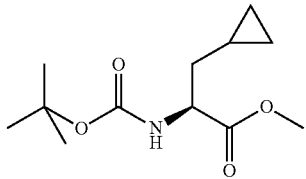 [SMILES: COC(=O)[C@H](CC1CC1)NC(=O)OC(C)(C)C]

To a mixture of (S)-2-(tert-butoxycarbonylamino)-3-cyclopropylpropanoic acid (CAN 89483-06-7, 6.792 g, 30 mmol) and K₂CO₃ (8.173 g, 59 mmol) in DMF (100 mL) was added MeI (10.37 g, 73 mmol). The reaction mixture was stirred overnight at room temperature. After filtration, the filtrate was concentrated to give the title compound as yellow oil (6.44 g, 89%); MS (EI): =266.2 [M+Na]⁺.

b) (S)-tert-Butyl 1-cyclopropyl-3-hydroxy-3-methylbutan-2-ylcarbamate

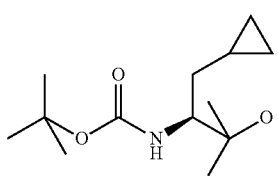 [SMILES: CC(C)(C)OC(=O)N[C@@H](CC1CC1)C(C)(C)O]

To a solution of (5)-methyl 2-(tert-butoxycarbonylamino)-3-cyclopropylpropanoate (0.972 g, 4 mmol) in THF (20 mL) was added a solution of MeMgBr in diethyl ether (3 M, 3.34 mL, 10 mmol) at 0° C. The resulting mixture was stirred at 0° C. for 3 h. Then it was quenched with water. The mixture was diluted with ethyl acetate (20 mL) and brine (20 mL). The organic layer was washed with brine (20 mL) again, dried over anhydrous sodium sulfate and concentrated to give the title compound as white solid (0.8 g, 82%); MS (EI):=266.2 [M+Na]⁺.

c) (S)-3-Amino-4-cyclopropyl-2-methyl-butan-2-ol

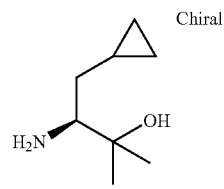

A solution of (S)-tert-butyl 1-cyclopropyl-3-hydroxy-3-methylbutan-2-ylcarbamate (0.8 g, 3 mmol) in ethyl acetate was saturated with hydrochloride (10 mL) and stirred for 1 h at room temperature. After diluting with water (20 mL), the layers were separated and the water phase was washed with ethyl acetate (20 mL). Then it was adjusted with 1 N NaOH to pH=8~9 and extracted with methylene chloride (3×20 mL). The combined organic layer was dried over anhydrous sodium sulfate and concentrated to give the title compound as yellow oil (0.3 g, 64%); MS (EI): =144.2 [M+Na]⁺.

d) 6-Cyclopropylmethoxy-5-(3,3-difluoro-azetidin-1-yl)-pyrazine-2-carboxylic acid ((S)-1-cyclopropylmethyl-2-hydroxy-2-methyl-propyl)-amide

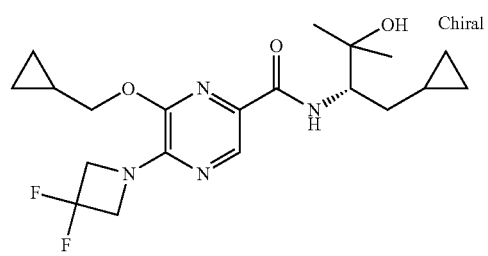 [SMILES: CC(C)(O)[C@H](CC1CC1)NC(=O)c1cnc(N2CC(F)(F)C2)c(OCC2CC2)n1]

The title compound was synthesized in analogy to Example 15, using 6-cyclopropylmethoxy-5-(3,3-difluoro-azetidin-1-yl)-pyrazine-2-carboxylic acid (Example 8d, 100 mg, 0.35 mmol) and (S)-3-amino-4-cyclopropyl-2-methyl-butan-2-ol (60.21 mg, 0.42 mmol) as starting materials, and isolated (50 mg, 34.72%) as white solid, LC-MS (UV peak area, ESI) 96.42%, 410.8 (M+H).

Example 17

5-Cyclopropyl-6-cyclopropylmethoxy-pyrazine-2-carboxylic acid ((S)-1-cyclopropylmethyl-2-hydroxy-2-methyl-propyl)-amide

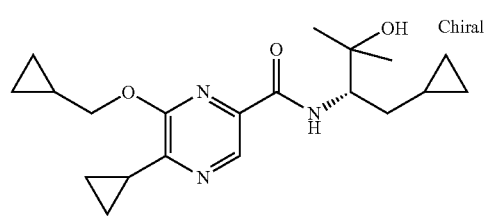 [SMILES: CC(C)(O)[C@H](CC1CC1)NC(=O)c1cnc(C2CC2)c(OCC2CC2)n1]

The title compound was synthesized in analogy to Example 15, using 5-cyclopropyl-6-cyclopropylmethoxy-pyrazine-2-carboxylic acid (Example 10 g, 100 mg, 0.43 mmol) and (S)-3-amino-4-cyclopropyl-2-methyl-butan-2-ol (87.83 mg, 0.64 mmol) as starting materials, and isolated (20 mg, 13.03%) as off white solid, LC-MS (UV peak area, ESI) 98.68%, 360.8 (M+H).

Example 18

5-Cyclopropyl-6-cyclopropylmethoxy-pyrazine-2-carboxylic acid piperidin-1-ylamide

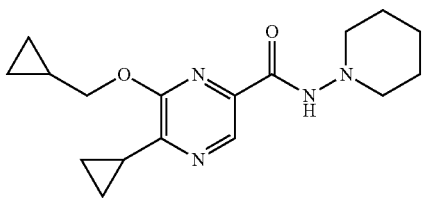 [SMILES: O=C(NN1CCCCC1)c1cnc(C2CC2)c(OCC2CC2)n1]

The title compound was synthesized in analogy to Example 15, using 5-cyclopropyl-6-cyclopropylmethoxy-pyrazine-2-carboxylic acid (Example 10 g, 100 mg, 0.43 mmol) and 1-amino-piperidine (CAN 2213-43-6; 76.9 mg, 0.51 mmol) as starting materials, and isolated (17 mg, 12.57%) as white solid; (UV peak area, ESI) 100%, 316.6 (M+H).

Example 19

5-Cyclopropyl-6-cyclopropylmethoxy-pyrazine-2-carboxylic acid (1-hydroxymethyl-2,2-dimethyl-propyl)-amide

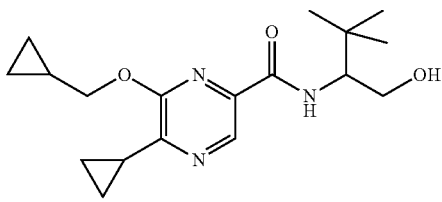 [SMILES: CC(C)(C)C(CO)NC(=O)c1cnc(C2CC2)c(OCC2CC2)n1]

The title compound was synthesized in analogy to Example 15, using 5-cyclopropyl-6-cyclopropylmethoxy-pyrazine-2-carboxylic acid (Example 10 g, 100 mg, 0.43 mmol) and 2-amino-3,3-dimethyl-1-butanol (CAN 3907-02-6, 74.8 mg, 0.64 mmol) as starting materials, and isolated (40 mg, 28.16%) as light yellow sticky solid; LC-MS (UV peak area, ESI) 89.43%, 334.2 (M+H).

Example 20

6-Cyclopropylmethoxy-5-(3,3-difluoro-azetidin-1-yl)-pyrazine-2-carboxylic acid [(S)-2-cyclopropyl-1-(5-methyl-[1,2,4]oxadiazol-3-yl)-ethyl]-amide a) (S)-tert-butyl 1-amino-3-cyclopropyl-1-oxopropan-2-yl-carbamate

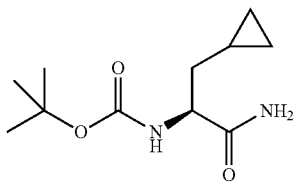 [SMILES: CC(C)(C)OC(=O)N[C@@H](CC1CC1)C(N)=O]

A mixture of (S)-2-(tert-butoxycarbonylamino)-3-cyclopropylpropanoic acid (CAN 89483-06-7, 10 g, 44 mmol), di-tert-butyl dicarbonate (CAN:24424-99-5, 14.28 g, 66 mmol) and pyridine (2.4 mL) in acetonitrile (200 mL) was stirred at room temperature for 20 min. Ammonia (10 mL) was added dropwise for 20 min. The resulting reaction mixture was stirred for 4 h. During removal of most of the solvent under reduced pressure the product precipitated and the solid was filtered off and washed with acetonitrile (20 mL). The solid was dried under reduced pressure to give the title compound (7.73 g, 78%) as white solid; MS (EI): 251.2 [M+Na]⁺.

b) (S)-tert-Butyl 1-cyano-2-cyclopropylethylcarbamate

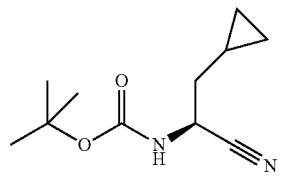

To a solution of (S)-tert-butyl 1-amino-3-cyclopropyl-1-oxopropan-2-ylcarbamate (3.7 g, 16 mmol) and triethylamine (6.55 g, 65 mmol) in methylene chloride (50 mL) was added trifluoroacetic acid anhydride (6.81 g, 32 mmol) dropwise at 0° C. The resulting mixture was allowed to warm to room temperature and stirred for 4 h. The mixture was washed with water (150 mL), citric acid (150 mL, 5 M) and brine (150 mL). The organic phase was dried over anhydrous sodium sulfate and concentrated to give product (3.31 g, 97%) as a yellow solid; MS (EI): 233.1 [M+Na]⁺.

c) (S,Z)-tent-Butyl 1-amino-3-cyclopropyl-1-(hydroxyimino)propan-2-ylcarbamate

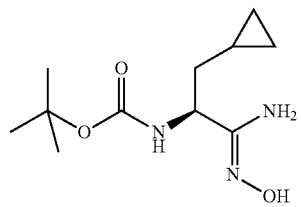 [SMILES: CC(C)(C)OC(=O)N[C@@H](CC1CC1)/C(N)=N/O]

Potassium carbonate (2.18 g, 16 mmol) was dissolved in water (8 mL) and hydroxylamine hydrochloride (1.1 g, 16 mmol) was added. A solution of (S)-tert-butyl 1-cyano-2-cyclopropylethylcarbamate (3.31 g, 16 mmol) in ethanol (24 mL) was added thereto and the resulting reaction mixture was stirred for 72 h. After evaporation of solvents, the residue was dissolved with ethyl acetate (20 mL) and then filtered. The filtrate was concentrated to yield crude product as yellow solid (3.61 g, 94%); MS (EI): 244.2 [M+H]⁺.

d) (S)-tent-Butyl 2-cyclopropyl-1-(5-methyl-1,2,4-oxadiazol-3-yl)ethylcarbamate

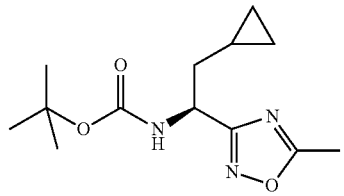 [SMILES: Cc1nc([C@H](CC2CC2)NC(=O)OC(C)(C)C)no1]

To a solution of acetic acid (0.224 g, 4 mmol) in DMF (5 mL) was added N,N'-carbonyldiimidazole (0.6 g, 4 mmol) and the mixture was stirred for 0.5 h at room temperature. (S,Z)-tert-butyl 1-amino-3-cyclopropyl-1-(hydroxyimino)propan-2-ylcarbamate (0.84 g, 3 mmol) was added and the mixture was heated to 120° C. and stirred for 4 h. After evaporation of solvents, the residue was purified by column chromatography (silica gel, 20 g, eluting with 10% ethyl acetate in petroleum ether) to give the title compound (0.5 g; 54%) as yellow solid; MS (EI): 290.1 [M+Na]⁺.

e) (S)-2-Cyclopropyl-1-(5-methyl-[1,2,4]oxadiazol-3-yl)-ethylamine

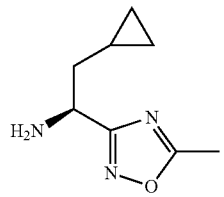

A solution of (S)-tert-butyl 2-cyclopropyl-1-(5-methyl-1,2,4-oxadiazol-3-yl)ethylcarbamate (0.5 g, 2 mmol) in sat. hydrochloric acid (10 mL) was stirred at room temperature for 1 h. Then water (20 mL) was added. The water phase was washed with ethyl acetate (2×20 mL) and adjusted with 2 M sodium hydroxide solution to pH=9~10. It was then extracted with ethyl acetate (2×20 mL). The organic layer was washed with brine (20 mL), dried over anhydrous sodium sulfate and concentrated to give crude product as a white solid (0.25 g, 80%); MS (EI): 168.2 [M+H]+.

f) 6-Cyclopropylmethoxy-5-(3,3-difluoro-azetidin-1-yl)-pyrazine-2-carboxylic acid [(S)-2-cyclopropyl-1-(5-methyl-[1,2,4]oxadiazol-3-yl)-ethyl]-amide

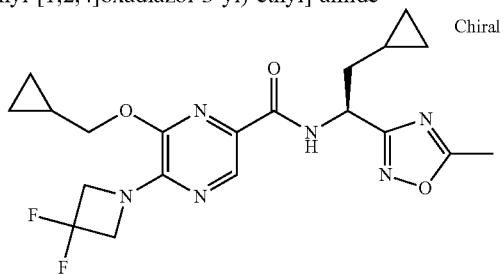

The title compound was synthesized in analogy to Example 15, using 6-cyclopropylmethoxy-5-(3,3-difluoro-azetidin-1-yl)-pyrazine-2-carboxylic acid (Example 8d, 100 mg, 0.35 mmol) and (S)-2-cyclopropyl-1-(5-methyl-[1,2,4]oxadiazol-3-yl)-ethylamine (88.51 mg, 0.53 mmol) as starting materials, and isolated (12 mg, 7.8%) as white solid, LC-MS (UV peak area, ESI) 97.53%, 435.51 (M+H).

Example 21

6-Cyclopropylmethoxy-5-(3,3-difluoro-azetidin-1-yl)-pyrazine-2-carboxylic acid (1-cyclopropyl-2-hydroxy-ethyl)-amide

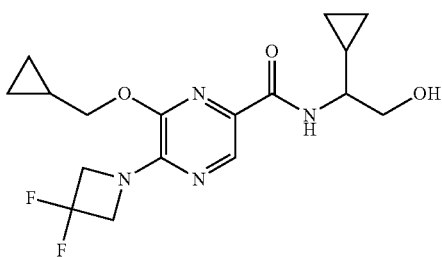 [SMILES: O=C(NC(CO)C1CC1)c1cnc(N2CC(F)(F)C2)c(OCC2CC2)n1]

The title compound was synthesized in analogy to Example 15, using 6-cyclopropylmethoxy-5-(3,3-difluoro-azetidin-1-yl)-pyrazine-2-carboxylic acid (Example 8d, 100 mg, 0.35 mmol) and β-amino-cyclopropaneethanol (CAN 776315-67-4, 78.94 mg, 0.53 mmol) as starting materials, and isolated (20 mg, 14.91%) as light brown solid; LC-MS (UV peak area, ESI) 97.84%, 368.9 (M+H).

Example 22

6-Cyclopropylmethoxy-5-(3,3-difluoro-azetidin-1-yl)-pyrazine-2-carboxylic acid ((S)-carbamoyl-phenyl-methyl)-amide

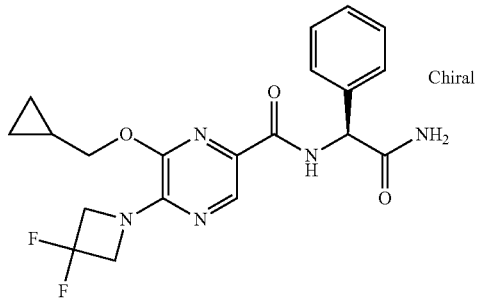 [SMILES: NC(=O)[C@@H](NC(=O)c1cnc(N2CC(F)(F)C2)c(OCC2CC2)n1)c1ccccc1]

The title compound was synthesized in analogy to Example 15, using 6-cyclopropylmethoxy-5-(3,3-difluoro-azetidin-1-yl)-pyrazine-2-carboxylic acid (Example 8d, 100 mg, 0.35 mmol) and (S)-2-amino-2-phenyl-acetamide (CAN 6485-52-5, 52.6 mg, 0.53 mmol) as starting materials, and isolated (25 mg, 17.07%) as light brown solid; LC-MS (UV peak area, ESI) 98.31%, 418.0 (M+H).

Example 23

(S)-2-[(5-Cyclopropyl-6-cyclopropylmethoxy-pyrazine-2-carbonyl)-amino]-3,3-dimethyl-butyric acid methyl ester

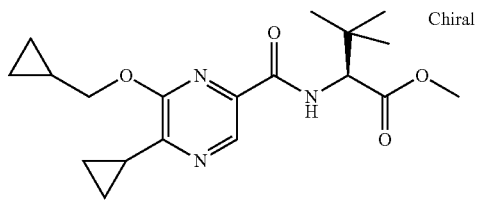 [SMILES: COC(=O)[C@@H](NC(=O)c1cnc(C2CC2)c(OCC2CC2)n1)C(C)(C)C]

The title compound was synthesized in analogy to Example 6, using 5-cyclopropyl-6-cyclopropylmethoxy-pyrazine-2-carboxylic acid (Example 10 g) and 3-methyl-L-valine methyl ester hydrochloride (1:1) (CAN 63038-27-7) as starting materials, and isolated (98 mg, 91%) as light yellow oil; LC-MS (UV peak area, ESI) 100%, 362.2081 (M+H).

Example 24

5-Cyclopropyl-6-cyclopropylmethoxy-pyrazine-2-carboxylic acid ((S)-2-cyclopropyl-1-methylcarbamoyl-ethyl)-amide a) ((S)-2-Cyclopropyl-1-methylcarbamoyl-ethyl)-carbamic acid tert-butyl ester

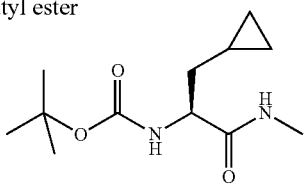

(S)-2-(tert-Butoxycarbonylamino)-3-cyclopropylpropanoic acid (2.0 g, 8.72 mmol) was combined with DMF (30 mL) to give a white suspension. At room temperature TBTU (3.08 g, 9.6 mmol) and DIEA (5.64 g, 7.47 ml, 43.6 mmol) were added followed by addition of methanamine hydrochloride (648 mg, 9.6 mmol). The suspension was stirred for 16 hours at room temperature and concentrated in vacuo to give 8.7 g of a light pink residue which was suspended in ethyl acetate (150 mL) and methanol (5 mL). Ice water and 2N sodium hydroxide solution (35 mL) were added and the mixture was stirred for 1 minute. The phases were separated, the water phase was extracted with ethyl acetate (70 mL), and organic phases were combined, dried with MgSO₄ and concentrated in vacuo. The residue was purified by chromatography (silica gel 0.063-0.200 mm, 100 g, ethyl acetate/n-heptane 3:1) to give the desired product (1.2 g, 56%) as white solid; MS (ESI): 243.1707 (M+H).

b) (S)-2-Amino-3-cyclopropyl-N-methyl-propionamide hydrochloride (1:1)

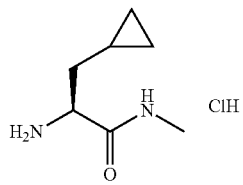

((S)-2-Cyclopropyl-1-methylcarbamoyl-ethyl)-carbamic acid tert-butyl ester (1.15 g, 4.75 mmol) was dissolved in ethanol (10 mL). A solution of 4M–HCl in dioxane (4.75 mL, 19.0 mmol) was added at room temperature and the mixture was stirred for 16 hours at room temperature. Solvents were removed in vacuo, and the residue was stirred for 1 hour with diethyl ether (10 mL). Filtration and drying of the precipitate delivered the desired product (0.79 g, 93%) as white solid; MS (ESI): 143.1173 (M+H).

c) 5-Cyclopropyl-6-cyclopropylmethoxy-pyrazine-2-carboxylic acid ((S)-2-cyclopropyl-1-methylcarbamoyl-ethyl)-amide

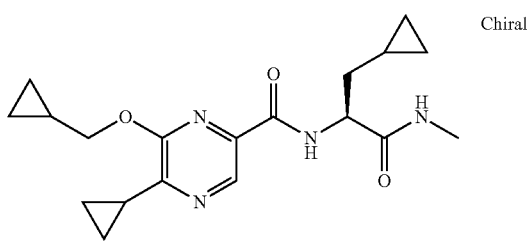 [SMILES: CNC(=O)[C@H](CC1CC1)NC(=O)c1cnc(C2CC2)c(OCC2CC2)n1]

The title compound was synthesized in analogy to Example 6, using 5-cyclopropyl-6-cyclopropylmethoxy-pyrazine-2-carboxylic acid (Example 10 g) and (S)-2-amino-3-cyclopropyl-N-methyl-propionamide hydrochloride (1:1) (Example 24b) as starting materials, and isolated (77 mg, 89%) as light yellow oil; LC-MS (UV peak area, ESI) 100%, 359.2081 (M+H).

Example 25

5-Cyclopropyl-6-cyclopropylmethoxy-pyrazine-2-carboxylic acid ((S)-2-cyclopropyl-1-dimethylcarbamoyl-ethyl)-amide a) ((S)-2-Cyclopropyl-1-dimethylcarbamoyl-ethyl)-carbamic acid tert-butyl ester

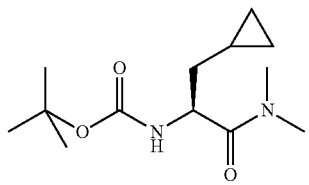 [SMILES: CN(C)C(=O)[C@H](CC1CC1)NC(=O)OC(C)(C)C]

(S)-2-(tert-Butoxycarbonylamino)-3-cyclopropylpropanoic acid (2.0 g, 8.72 mmol) was combined with DMF (30 mL) to give a white suspension. At room temperature TBTU (3.08 g, 9.6 mmol) and DIEA (5.64 g, 7.47 ml, 43.6 mmol) were added followed by addition of dimethylamine hydrochloride (782 mg, 9.6 mmol). The suspension was stirred for 16 hours at room temperature and concentrated in vacuo to give 8.7 g of a light pink residue which was suspended in ethyl acetate (150 mL) and methanol (5 mL). Ice water and 2N sodium hydroxide solution (35 mL) were added and the mixture was stirred for 1 minute. The phases were separated, the water phase was extracted with ethyl acetate (70 mL), and organic phases were combined, dried with MgSO₄ and concentrated in vacuo. The residue was purified by chromatography (silica gel 0.063-0.200 mm, 100 g, ethyl acetate/n-heptane 3:1) to give the desired product (1.24 g, 56%) as white solid; GC-MS (EI): 256 (M).

b) (S)-2-Amino-3-cyclopropyl-N,N-dimethyl-propionamide hydrochloride (1:1)

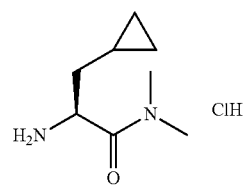

((S)-2-Cyclopropyl-1-dimethylcarbamoyl-ethyl)-carbamic acid tert-butyl ester (1.20 g, 4.68 mmol) was dissolved in ethanol (10 mL). A solution of 4M HCl in dioxane (4.68 mL, 19.0 mmol) was added at room temperature and the mixture was stirred for 16 hours at room temperature. Solvents were removed in vacuo, and the residue was stirred for 1 hour with diethyl ether (10 mL). Filtration and drying of the precipitate delivered the desired product (0.82 g, 91%) as white solid; MS (ESI): 157.1337 (M+H).

c) 5-Cyclopropyl-6-cyclopropylmethoxy-pyrazine-2-carboxylic acid ((S)-2-cyclopropyl-1-dimethylcarbamoyl-ethyl)-amide

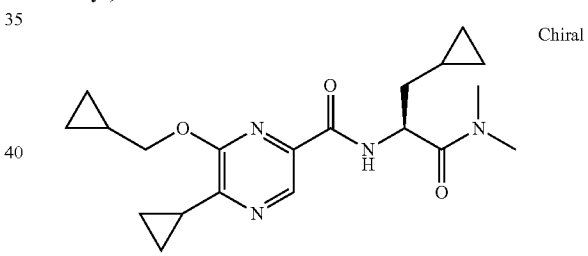

The title compound was synthesized in analogy to Example 6, using 5-cyclopropyl-6-cyclopropylmethoxy-pyrazine-2-carboxylic acid (Example 10 g) and (S)-2-amino-3-cyclopropyl-N,N-dimethyl-propionamide hydrochloride (1:1) (Example 25b) as starting materials, and isolated (80 mg, 86%) as light yellow oil; LC-MS (UV peak area, ESI) 100%, 373.2231 (M+H).

Example 26

5-Cyclopropyl-6-cyclopropylmethoxy-pyrazine-2-carboxylic acid ((S)-3-methyl-1-methylcarbamoyl-butyl)-amide

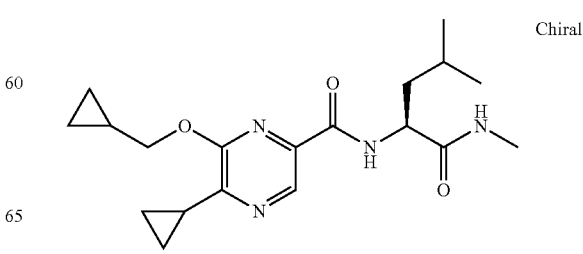

The title compound was synthesized in analogy to Example 6, using 5-cyclopropyl-6-cyclopropylmethoxy-pyrazine-2-carboxylic acid (Example 10 g) and (2S)-2-amino-N,4-dimethyl-pentanamide monohydrochloride (CAN 99145-71-8) as starting materials, and isolated (67 mg, 87%) as off-white solid; LC-MS (UV peak area, ESI) 100%, 361.2232 (M+H).

Example 27

5-Cyclopropyl-6-cyclopropylmethoxy-pyrazine-2-carboxylic acid ((S)-1-dimethylcarbamoyl-3-methyl-butyl)-amide

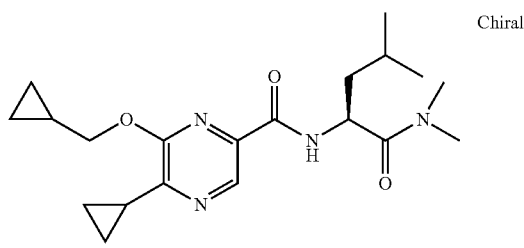 [SMILES: CC(C)C[C@H](NC(=O)c1cnc(C2CC2)c(OCC2CC2)n1)C(=O)N(C)C]

The title compound was synthesized in analogy to Example 6, using 5-cyclopropyl-6-cyclopropylmethoxy-pyrazine-2-carboxylic acid (Example 10 g) and (2S)-2-amino-N,N,4-trimethyl-pentanamide hydrochloride (1:1) (CAN 207595-81-1) as starting materials, and isolated (68 mg, 85%) as yellow solid; LC-MS (UV peak area, ESI) 100%, 375.2387 (M+H).

Example 28

5-Cyclopropyl-6-cyclopropylmethoxy-pyrazine-2-carboxylic acid ((S)-1-carbamoyl-2-cyclopropyl-ethyl)-amide

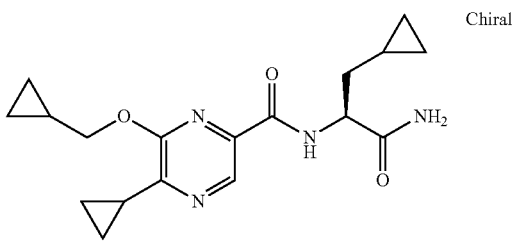 [SMILES: NC(=O)[C@H](CC1CC1)NC(=O)c1cnc(C2CC2)c(OCC2CC2)n1]

The title compound was synthesized in analogy to Example 6, using 5-cyclopropyl-6-cyclopropylmethoxy-pyrazine-2-carboxylic acid (Example 10 g) and (S)-α-amino-cyclopropanepropanamide (CAN 156077-93-9) as starting materials, and isolated (22 mg, 30%) as light yellow oil; LC-MS (UV peak area, ESI) 100%, 345.1929 (M+H).

Example 29

5-Cyclopropyl-6-cyclopropylmethoxy-pyrazine-2-carboxylic acid ((S)-1-carbamoyl-3-methyl-butyl)-amide

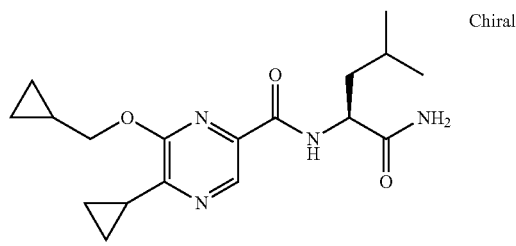 [SMILES: CC(C)C[C@H](NC(=O)c1cnc(C2CC2)c(OCC2CC2)n1)C(N)=O]

The title compound was synthesized in analogy to Example 6, using 5-cyclopropyl-6-cyclopropylmethoxy-pyrazine-2-carboxylic acid (Example 10 g) and (2S)-2-amino-4-methyl-pentanamide hydrochloride (1:1) (CAN 10466-61-2) as starting materials, and isolated (46 mg, 62%) as light yellow gum; LC-MS (UV peak area, ESI) 100%, 347.2081 (M+H).

Example 30

2-[(5-Cyclopropyl-6-cyclopropylmethoxy-pyrazine-2-carbonyl)-amino]-2-ethyl-butyric acid methyl ester

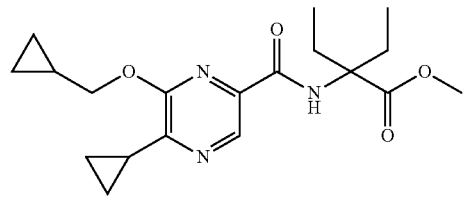 [SMILES: CCC(CC)(NC(=O)c1cnc(C2CC2)c(OCC2CC2)n1)C(=O)OC]

The title compound was synthesized in analogy to Example 6, using 5-cyclopropyl-6-cyclopropylmethoxy-pyrazine-2-carboxylic acid (Example 10 g) and 2-amino-2-ethyl-butanoic acid methyl ester hydrochloride (1:1) (CAN 92398-54-4) as starting materials, and isolated (86 mg, 93%) as yellow oil; LC-MS (UV peak area, ESI) 100%, 362.2071 (M+H).

Example 31

6-Cyclopropylmethoxy-5-(3,3-difluoro-azetidin-1-yl)-pyrazine-2-carboxylic acid ((S)-2-cyclopropyl-1-methylcarbamoyl-ethyl)-amide

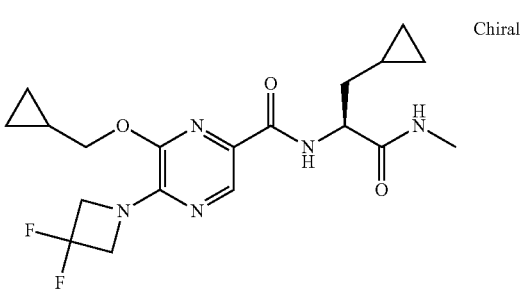 [SMILES: CNC(=O)[C@H](CC1CC1)NC(=O)c1cnc(N2CC(F)(F)C2)c(OCC2CC2)n1]

The title compound was synthesized in analogy to Example 6, using 6-cyclopropyl-methoxy-5-(3,3-difluoro-azetidin-1-yl)-pyrazine-2-carboxylic acid (Example 8d) and (S)-2-amino-3-cyclopropyl-N-methyl-propionamide hydrochloride (1:1) (Example 24b) as starting materials, and isolated (64 mg, 89%) as white solid; LC-MS (UV peak area, ESI) 100%, 410.2001 (M+H).

Example 32

6-Cyclopropylmethoxy-5-(3,3-difluoro-azetidin-1-yl)-pyrazine-2-carboxylic acid ((S)-2-cyclopropyl-1-dimethylcarbamoyl-ethyl)-amide

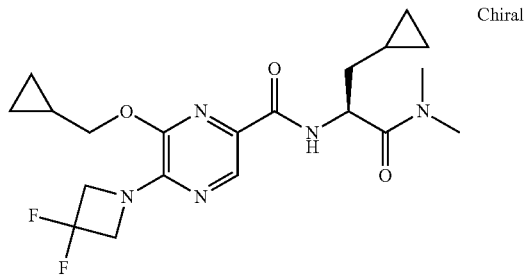 [SMILES: CN(C)C(=O)[C@H](CC1CC1)NC(=O)c1cnc(N2CC(F)(F)C2)c(OCC2CC2)n1]

The title compound was synthesized in analogy to Example 6, using 6-cyclopropyl-methoxy-5-(3,3-difluoro-azetidin-1-yl)-pyrazine-2-carboxylic acid (Example 8d) and (S)-2-amino-3-cyclopropyl-N,N-dimethyl-propionamide hydrochloride (1:1) (Example 25b) as starting materials, and isolated (63 mg, 85%) as white solid; LC-MS (UV peak area, ESI) 100%, 424.2155 (M+H).

Example 33

6-Cyclopropylmethoxy-5-(3,3-difluoro-azetidin-1-yl)-pyrazine-2-carboxylic acid ((S)-3-methyl-1-methylcarbamoyl-butyl)-amide

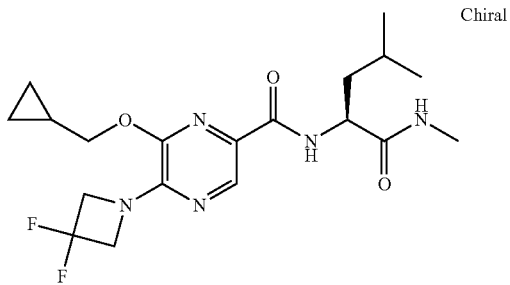 [SMILES: CNC(=O)[C@H](CC(C)C)NC(=O)c1cnc(N2CC(F)(F)C2)c(OCC2CC2)n1]

The title compound was synthesized in analogy to Example 6, using 6-cyclopropyl-methoxy-5-(3,3-difluoro-azetidin-1-yl)-pyrazine-2-carboxylic acid (Example 8d) and (2S)-2-amino-N,4-dimethyl-pentanamide monohydrochloride (CAN 99145-71-8) as starting materials, and isolated (59 mg, 82%) as white solid; LC-MS (UV peak area, ESI) 100%, 412.2155 (M+H).

Example 34

6-Cyclopropylmethoxy-5-(3,3-difluoro-azetidin-1-yl)-pyrazine-2-carboxylic acid ((S)-1-dimethylcarbamoyl-3-methyl-butyl)-amide

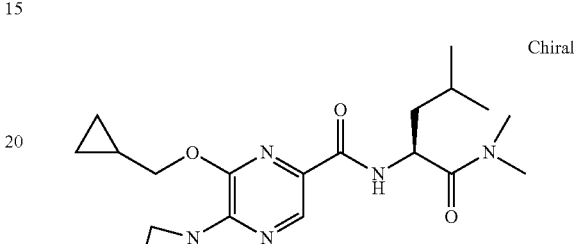

The title compound was synthesized in analogy to Example 6, using 6-cyclopropyl-methoxy-5-(3,3-difluoro-azetidin-1-yl)-pyrazine-2-carboxylic acid (Example 8d) and (2S)-2-amino-N,N,4-trimethyl-pentanamide hydrochloride (1:1) (CAN 207595-81-1) as starting materials, and isolated (63 mg, 85%) as white solid; LC-MS (UV peak area, ESI) 100%, 426.2311 (M+H).

Example 35

(S)-3-Cyclopropyl-2-[(5-cyclopropyl-6-cyclopropylmethoxy-pyrazine-2-carbonyl)-amino]-propionic acid methyl ester

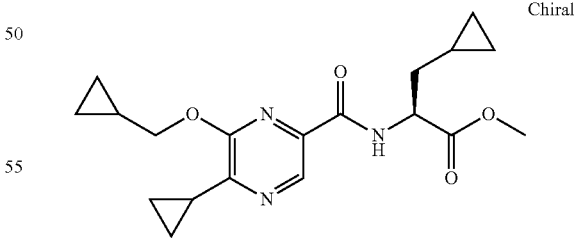

The title compound was synthesized in analogy to Example 6, using 5-cyclopropyl-6-cyclopropylmethoxy-pyrazine-2-carboxylic acid (Example 10 g) and (αS)-α-amino-cyclopropanepropanoic acid methyl ester hydrochloride (1:1) (CAN 206438-31-5) as starting materials, and isolated (80 mg, 75%) as yellow oil; LC-MS (UV peak area, ESI) 100%, 360.1920 (M+H).

Example 36

(S)-3-Cyclopropyl-2-{[6-cyclopropylmethoxy-5-(3,3-difluoro-azetidin-1-yl)-pyrazine-2-carbonyl]-amino}-propionic acid methyl ester

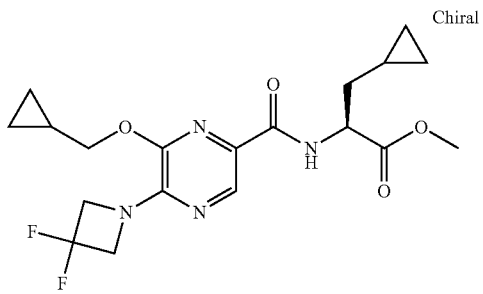 [SMILES: COC(=O)[C@H](CC1CC1)NC(=O)c1cnc(N2CC(F)(F)C2)c(OCC2CC2)n1]

The title compound was synthesized in analogy to Example 6, using 6-cyclopropyl-methoxy-5-(3,3-difluoro-azetidin-1-yl)-pyrazine-2-carboxylic acid (Example 8d) and (αS)-α-amino-cyclopropanepropanoic acid methyl ester hydrochloride (1:1) (CAN 206438-31-5) as starting materials, and isolated (83 mg, 82%) as light yellow oil; LC-MS (UV peak area, ESI) 100%, 411.1836 (M+H).

Example 37

5-Cyclopropyl-6-cyclopropylmethoxy-pyrazine-2-carboxylic acid ((S)-1-carbamoyl-2-phenyl-ethyl)-amide

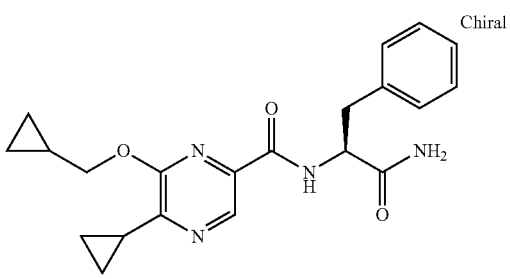 [SMILES: NC(=O)[C@H](Cc1ccccc1)NC(=O)c1cnc(C2CC2)c(OCC2CC2)n1]

The title compound was synthesized in analogy to Example 15, using 5-cyclopropyl-6-cyclopropylmethoxy-pyrazine-2-carboxylic acid (Example 10 g, 100 mg, 0.43 mmol) and (S)-2-amino-3-phenyl-propionamide hydrochloride (1:1) (CAN 5241-58-7, 118.84 mg, 0.64 mmol) as starting materials, and isolated (60 mg, 37.03%) as colorless sticky solid; LC-MS (UV peak area, ESI) 100%, 381.4 (M+H).

Example 38

6-Cyclopropylmethoxy-5-(3,3-difluoro-azetidin-1-yl)-pyrazine-2-carboxylic acid ((S)-1-carbamoyl-2-phenyl-ethyl)-amide

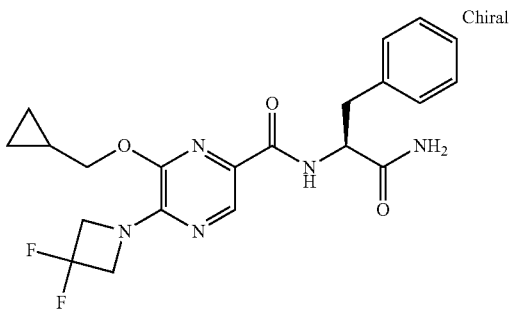 [SMILES: NC(=O)[C@H](Cc1ccccc1)NC(=O)c1cnc(N2CC(F)(F)C2)c(OCC2CC2)n1]

The title compound was synthesized in analogy to Example 15, using 6-cyclopropyl-methoxy-5-(3,3-difluoro-azetidin-1-yl)-pyrazine-2-carboxylic acid (Example 8d, 100 mg, 0.35 mmol) and (S)-2-amino-3-phenyl-propionamide hydrochloride (1:1) (CAN 5241-58-7, 87.84 mg, 0.53 mmol) as starting materials, and isolated (75 mg, 49.6%) as colorless sticky solid; LC-MS (UV peak area, ESI) 100%, 432.2 (M+H).

Example 39

6-Cyclopropylmethoxy-5-(3,3-difluoro-azetidin-1-yl)-pyrazine-2-carboxylic acid ((S)-1-carbamoyl-2-cyclopropyl-ethyl)-amide

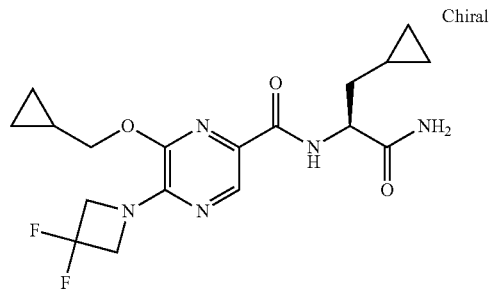 [SMILES: NC(=O)[C@H](CC1CC1)NC(=O)c1cnc(N2CC(F)(F)C2)c(OCC2CC2)n1]

The title compound was synthesized in analogy to Example 6, using 6-cyclopropyl-methoxy-5-(3,3-difluoro-azetidin-1-yl)-pyrazine-2-carboxylic acid (Example 8d) and (S)-α-amino-cyclopropanepropanamide (CAN 156077-93-9) as starting materials, and isolated (40 mg, 57%) as white solid; LC-MS (UV peak area, ESI) 100%, 396.1845 (M+H).

Example 40

5-Cyclopropyl-6-cyclopropylmethoxy-pyrazine-2-carboxylic acid [(SR)-cyclopropyl-(5-methyl-[1,2,4]oxadiazol-3-yl)-methyl]-amide a) 5-Cyclopropyl-6-cyclopropylmethoxy-pyrazine-2-carboxylic acid [(cyclopropyl-(5-methyl-[1,2,4]oxadiazol-3-yl)-methyl]-amide

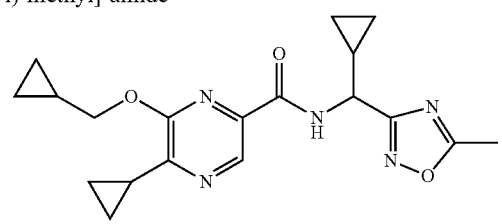

The title compound was synthesized in analogy to Example 6, using 5-cyclopropyl-6-cyclopropylmethoxy-pyrazine-2-carboxylic acid (Example 10 g) and α-cyclopropyl-5-methyl-1,2,4-oxadiazole-3-methanamine (CAN 1291557-80-6) as starting materials, and isolated (95 mg, 86%) as light yellow solid; LC-MS (UV peak area, ESI) 100%, 370.1876 (M+H).

b) 5-Cyclopropyl-6-cyclopropylmethoxy-pyrazine-2-carboxylic acid [(SR)-(cyclopropyl-(5-methyl-[1,2,4]oxadiazol-3-yl)-methyl]-amide

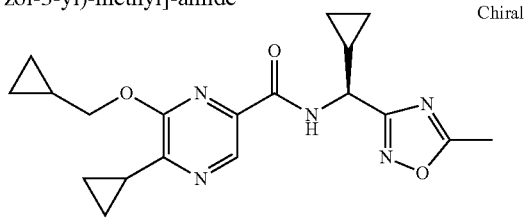

The enantiomers of 5-cyclopropyl-6-cyclopropyl-methoxy-pyrazine-2-carboxylic acid [(cyclopropyl-(5-methyl-[1,2,4]oxadiazol-3-yl)-methyl]-amide (Example 40a) were separated by chiral HPLC (ChiralPak AD, 10% 2-propanol/n-heptane). The (+) enantiomer was isolated as colorless viscous oil; LC-MS (UV peak area/ESI) 100%, 370.1874 (M+H); (+) enantiomer, $\alpha_D^{20}$ (MeOH)=31.0°.

Example 41

5-Cyclopropyl-6-cyclopropylmethoxy-pyrazine-2-carboxylic acid [(RS)-cyclopropyl-(5-methyl-[1,2,4]oxadiazol-3-yl)-methyl]-amide

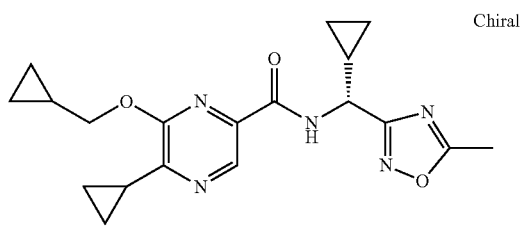 [SMILES: Cc1nc([C@H](NC(=O)c2cnc(C3CC3)c(OCC3CC3)n2)C2CC2)no1]

The enantiomers of 5-cyclopropyl-6-cyclopropyl-methoxy-pyrazine-2-carboxylic acid [(cyclopropyl-(5-methyl-[1,2,4]oxadiazol-3-yl)-methyl]-amide (Example 40a) were separated by chiral HPLC (ChiralPak AD, 10% 2-propanol/n-heptane). The (−) enantiomer was isolated as colorless viscous oil; LC-MS (UV peak area/ESI) 100%, 370.1874 (M+H); (−) enantiomer, $\alpha_D^2$ (MeOH)=−26.0°.

Example 42

6-Cyclopropylmethoxy-5-(3,3-difluoro-azetidin-1-yl)-pyrazine-2-carboxylic acid [(SR)-cyclopropyl-(5-methyl-[1,2,4]oxadiazol-3-yl)-methyl]-amide a) 6-Cyclopropylmethoxy-5-(3,3-difluoro-azetidin-1-yl)-pyrazine-2-carboxylic acid [(cyclopropyl-(5-methyl-[1,2,4]oxadiazol-3-yl)-methyl]-amide

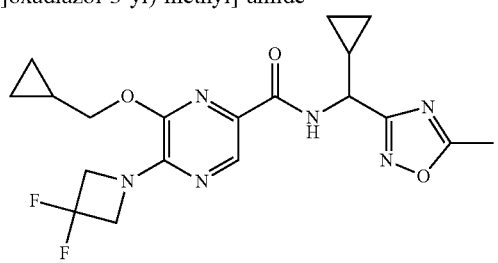

The title compound was synthesized in analogy to Example 6, using 6-cyclopropyl-methoxy-5-(3,3-difluoro-azetidin-1-yl)-pyrazine-2-carboxylic acid (Example 8d) and α-cyclopropyl-5-methyl-1,2,4-oxadiazole-3-methanamine (CAN 1291557-80-6) as starting materials, and isolated (86 mg, 83%) as white solid; LC-MS (UV peak area, ESI) 100%, 421.1792 (M+H).

b) 6-Cyclopropylmethoxy-5-(3,3-difluoro-azetidin-1-yl)-pyrazine-2-carboxylic acid [(SR)-cyclopropyl-(5-methyl-[1,2,4]oxadiazol-3-yl)-methyl]-amide

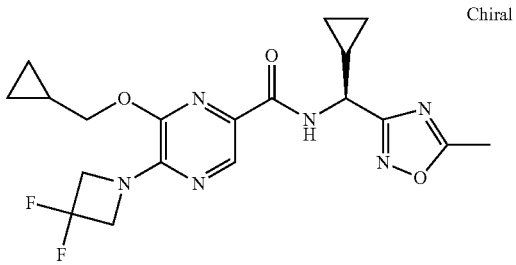 [SMILES: Cc1nc([C@@H](NC(=O)c2cnc(N3CC(F)(F)C3)c(OCC3CC3)n2)C2CC2)no1]

The enantiomers of 6-cyclopropylmethoxy-5-(3,3-difluoro-azetidin-1-yl)-pyrazine-2-carboxylic acid [(cyclopropyl-(5-methyl-[1,2,4]oxadiazol-3-yl)-methyl]-amide (Example 42a) were separated by chiral HPLC (ChiralPak AD, 20% ethanol/n-heptane). The (+) enantiomer was isolated as white solid; LC-MS (UV peak area/ESI) 100%, 421.1794 (M+H); $\alpha_D^{20}$ (MeOH)=+55.4°.

Example 43

6-Cyclopropylmethoxy-5-(3,3-difluoro-azetidin-1-yl)-pyrazine-2-carboxylic acid [(RS)-cyclopropyl-(5-methyl-[1,2,4]oxadiazol-3-yl)-methyl]-amide

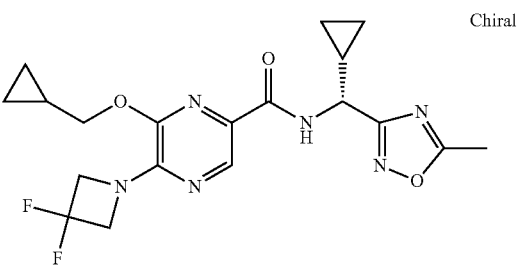 [SMILES: Cc1nc([C@H](NC(=O)c2cnc(N3CC(F)(F)C3)c(OCC3CC3)n2)C2CC2)no1]

The enantiomers of 6-cyclopropylmethoxy-5-(3,3-difluoro-azetidin-1-yl)-pyrazine-2-carboxylic acid [(cyclopropyl-(5-methyl-[1,2,4]oxadiazol-3-yl)-methyl]-amide (Example 42a) were separated by chiral HPLC (ChiralPak AD, 20% ethanol/n-heptane). The (−) enantiomer was isolated as white solid; LC-MS (UV peak area/ESI) 100%, 421.1794 (M+H); $\alpha_D^{20}$ (MeOH)=−52.2°.

Example 44

(S)-2-[(5-Cyclopropyl-6-cyclopropylmethoxy-pyrazine-2-carbonyl)-amino]-3,3-dimethyl-butyric acid

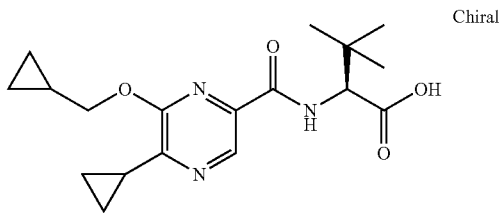 [SMILES: CC(C)(C)[C@H](NC(=O)c1cnc(C2CC2)c(OCC2CC2)n1)C(=O)O]

To a solution of (S)-2-[(5-cyclopropyl-6-cyclopropylmethoxy-pyrazine-2-carbonyl)-amino]-3,3-dimethyl-butyric acid methyl ester (58 mg, 160 µmol) in THF (3 mL) was added lithium hydroxide (30 mg, 715 µmol) in water (1 mL) and the mixture was stirred at reflux temperature for 3 hours. After cooling the mixture was poured into water (10 mL), acidified with 1 N HCl (1 mL) and extracted with TBME. Organic phases were combined, dried with Na2SO4, filtered and concentrated in vacuo to give the title compound (61 mg, quant.) as white solid; LC-MS (UV peak area/ESI) 100%, 348.1920 (M+H).

Example 45

5-Cyclopropyl-6-cyclopropylmethoxy-pyrazine-2-carboxylic acid [1-methyl-1-(5-methyl-[1,2,4]oxadiazol-3-yl)-ethyl]-amide

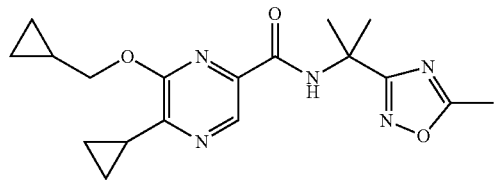 [SMILES: Cc1nc(C(C)(C)NC(=O)c2cnc(C3CC3)c(OCC3CC3)n2)no1]

The title compound was synthesized in analogy to Example 6, using 5-cyclopropyl-6-cyclopropylmethoxy-pyrazine-2-carboxylic acid (Example 10 g) and α,α,5-trimethyl-1,2,4-oxadiazole-3-methanamine hydrochloride (CAN 1240526-27-5) as starting materials, and isolated (64 mg, 84%) as light yellow solid; LC-MS (UV peak area, ESI) 100%, 358.1869 (M+H).

Example 46

5-Cyclopropyl-6-cyclopropylmethoxy-pyrazine-2-carboxylic acid ((S)-1-pyridin-2-yl-ethyl)-amide

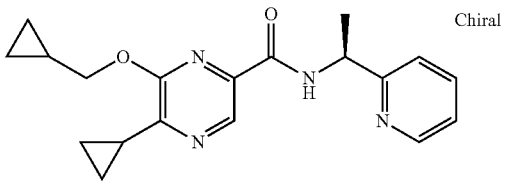 [SMILES: C[C@H](NC(=O)c1cnc(C2CC2)c(OCC2CC2)n1)c1ccccn1]

The title compound was synthesized in analogy to Example 15, using 5-cyclopropyl-6-cyclopropylmethoxy-pyrazine-2-carboxylic acid (Example 10 g, 100 mg, 0.43 mmol) and (αS)-α-methyl-2-pyridinemethanamine hydrochloride (1:1) (100.0 mg, 0.64 mmol) as starting materials, and isolated (15 mg, 13.03%) as off white solid, LC-MS (UV peak area, ESI) 97.58%, 339.0 (M+H).

Example 47

6-Cyclopropylmethoxy-5-(3,3-difluoro-azetidin-1-yl)-pyrazine-2-carboxylic acid ((R)-2,2,2-trifluoro-1-pyridin-2-yl-ethyl)-amide a) (2,2,2-Trifluoro-1-pyridin-2-yl-ethyl)-carbamic acid (1R,2S,5R)-2-isopropyl-5-methyl-cyclohexyl ester

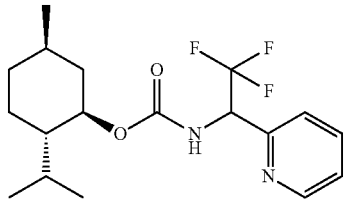

α-(Trifluoromethyl)-2-pyridinemethanamine (CAN 503173-14-6, 2.0 g, 11.4 mmol) and DIEA (2.94 g, 3.97 ml, 22.7 mmol) were combined with THF (20 mL) with ice cooling to give a light yellow solution. (−)-Menthyl chloroformate (2.73 g, 12.5 mmol) in THF (20 mL) was added drop by drop during 30 minutes at 0° C. The reaction mixture was stirred for 4 h at 0° C. Afterwards the mixture was poured into ethyl acetate (50 mL) and washed with water (2×25 mL). The aqueous layer was back-extracted with ethyl acetate (50 mL). The organic phases were combined, dried with Na2SO4 and concentrated in vacuo. The residue was purified by preparative HPLC to give the title compound (4.1 g, quant.) as white solid which was used in the next step without further purification; MS: (EI) 359.2 (M+H).

b) ((R)-2,2,2-Trifluoro-1-pyridin-2-yl-ethyl)-carbamic acid (1R,2S,5R)-2-isopropyl-5-methyl-cyclohexyl ester

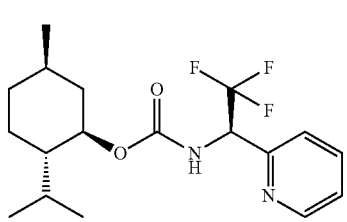 [SMILES: CC(C)[C@@H]1CC[C@@H](C)C[C@H]1OC(=O)N[C@H](c1ccccn1)C(F)(F)F]

The title compound (1.42 g) was isolated by chiral HPLC (ChiralPak AD, ethanol/n-heptane). The (−)-enantiomer was isolated; MS: (EI) 359.2 (M+H).

c) (R)-2,2,2-Trifluoro-1-pyridin-2-yl-ethylamine

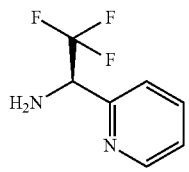

((R)-2,2,2-Trifluoro-1-pyridin-2-yl-ethyl)-carbamic acid (1R,2S,5R)-2-isopropyl-5-methyl-cyclohexyl ester (1200 mg, 3.35 mmol) was dissolved in dichloromethane (20 mL) and cooled to 0° C. To this solution was at 0° C. added TFA (4.44 g, 3 ml, 38.9 mmol) and then triflic acid (1.69 g, 1000 µl, 11.3 mmol). The yellow reaction mixture was stirred at 0° C.

for 8 hours and at room temperature for 18 hours before it was concentrated in vacuo. The residue was poured into ethyl acetate (100 mL) and extracted with 1M NaOH (1×20 mL). The aqueous phase was extracted with ethyl acetate (100 mL), organic phases were combined, dried with Na2SO4 and concentrated in vacuo. The residue, a yellow oil, was purified by flash chromatography (silica gel, 20 g, 0% to 100% ethyl acetate in n-heptane) to give the title compound (0.38 g, 65%) as a colorless oil; LC-MS (ESI) 177.0635 (M+H); (−) enantiomer.

d) 6-Cyclopropylmethoxy-5-(3,3-difluoro-azetidin-1-yl)-pyrazine-2-carboxylic acid ((R)-2,2,2-trifluoro-1-pyridin-2-yl-ethyl)-amide

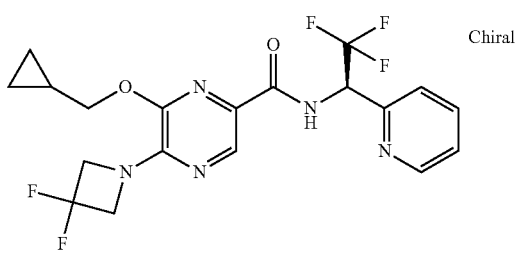 [SMILES: O=C(N[C@H](c1ccccn1)C(F)(F)F)c1cnc(N2CC(F)(F)C2)c(OCC2CC2)n1]

The title compound was synthesized in analogy to Example 6, using 6-cyclopropyl-methoxy-5-(3,3-difluoro-azetidin-1-yl)-pyrazine-2-carboxylic acid (Example 8d) and (R)-2,2,2-trifluoro-1-pyridin-2-yl-ethylamine (Example 47c) as starting materials, and isolated (78 mg, 86%) as white solid; LC-MS (UV peak area, ESI) 100%, 444.1447 (M+H).

Example 48

6-Cyclopropylmethoxy-5-(3,3-difluoro-azetidin-1-yl)-pyrazine-2-carboxylic acid ((S)-2,2,2-trifluoro-1-pyridin-2-yl-ethyl)-amide a) ((S)-2,2,2-Trifluoro-1-pyridin-2-yl-ethyl)-carbamic acid (1R,2S,5R)-2-isopropyl-5-methyl-cyclohexyl ester

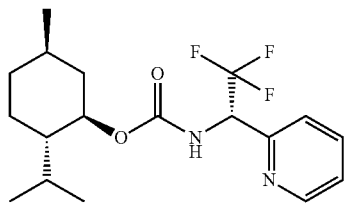 [SMILES: CC(C)[C@@H]1CC[C@@H](C)C[C@H]1OC(=O)N[C@@H](c1ccccn1)C(F)(F)F]

The title compound (1.50 g) was isolated by chiral HPLC by chiral HPLC (ChiralPak AD, ethanol/n-heptane). The (+)-enantiomer was isolated; MS: (EI) 359.2 (M+H).

b) (S)-2,2,2-Trifluoro-1-pyridin-2-yl-ethylamine

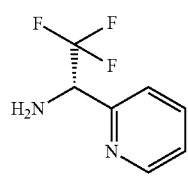 [SMILES: N[C@@H](c1ccccn1)C(F)(F)F]

((S)-2,2,2-Trifluoro-1-pyridin-2-yl-ethyl)-carbamic acid (1R,2S,5R)-2-isopropyl-5-methyl-cyclohexyl ester (1200 mg, 3.35 mmol) was dissolved in dichloromethane (20 mL) and cooled to 0° C. To this solution was at 0° C. added TFA (4.44 g, 3 ml, 38.9 mmol) and then triflic acid (1.69 g, 1000 μl, 11.3 mmol). The yellow reaction mixture was stirred at 0° C. for 8 hours and at room temperature for 23 hours before it was concentrated in vacuo. The residue was poured into ethyl acetate (100 mL) and extracted with 1M NaOH (1×20 mL). The aqueous phase was extracted with ethyl acetate (100 mL), organic phases were combined, dried with Na2SO4 and concentrated in vacuo. The residue, a yellow oil, was purified by flash chromatography (silica gel, 20 g, 0% to 100% ethyl acetate in n-heptane) to give the title compound (0.37 g, 63%) as a colorless oil; MS (EI) 177.1 (M+H); $\alpha_D^{20}$ (MeOH)=+10.5°.

c) 6-Cyclopropylmethoxy-5-(3,3-difluoro-azetidin-1-yl)-pyrazine-2-carboxylic acid ((S)-2,2,2-trifluoro-1-pyridin-2-yl-ethyl)-amide

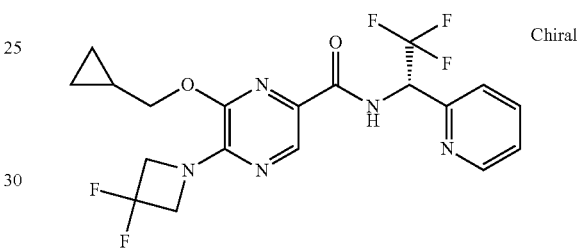

The title compound was synthesized in analogy to Example 6, using 6-cyclopropyl-methoxy-5-(3,3-difluoro-azetidin-1-yl)-pyrazine-2-carboxylic acid (Example 8d) and (R)-2,2,2-trifluoro-1-pyridin-2-yl-ethylamine (Example 48b) as starting materials, and isolated (66 mg, 85%) as white solid; LC-MS (UV peak area, ESI) 100%, 444.1448 (M+H).

Example 49

5-Cyclopropyl-6-cyclopropylmethoxy-pyrazine-2-carboxylic acid ((S)-2,2,2-trifluoro-1-pyridin-2-yl-ethyl)-amide

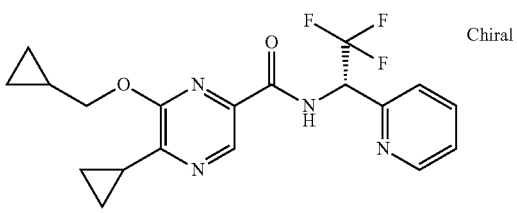 [SMILES: O=C(N[C@@H](c1ccccn1)C(F)(F)F)c1cnc(C2CC2)c(OCC2CC2)n1]

The title compound was synthesized in analogy to Example 6, using 5-cyclopropyl-6-cyclopropylmethoxy-pyrazine-2-carboxylic acid (Example 10 g) and (S)-2,2,2-trifluoro-1-pyridin-2-yl-ethylamine (Example 48b) as starting materials, and isolated (71 mg, 85%) as light yellow gum; LC-MS (UV peak area, ESI) 100%, 393.1524 (M+H).

Example 50

6-Cyclopropylmethoxy-5-(3,3-difluoro-azetidin-1-yl)-pyrazine-2-carboxylic acid (1-ethyl-1-methylcarbamoyl-propyl)-amide

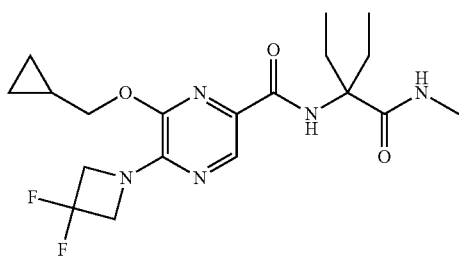 [SMILES: CCC(CC)(NC(=O)c1cnc(N2CC(F)(F)C2)c(OCC2CC2)n1)C(=O)NC]

The title compound was synthesized in analogy to Example 15, using 6-cyclopropyl-methoxy-5-(3,3-difluoro-azetidin-1-yl)-pyrazine-2-carboxylic acid (Example 8d, 100 mg, 0.35 mmol) and 2-amino-2-ethyl-N-methyl-butyramide hydrochloride (1:1) (61.6 mg, 0.53 mmol) as starting materials, and isolated (30 mg, 19.33%) as colorless sticky solid, LC-MS (UV peak area, ESI) 96.50%, 412.4 (M+H).

Example 51

5-Cyclopropyl-6-cyclopropylmethoxy-pyrazine-2-carboxylic acid ((R)-1-hydroxymethyl-1,2-dimethyl-propyl)-amide

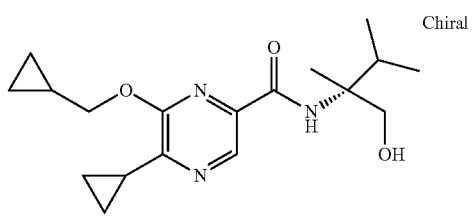 [SMILES: CC(C)[C@](C)(CO)NC(=O)c1cnc(C2CC2)c(OCC2CC2)n1]

Chiral

The title compound was synthesized in analogy to Example 15, using 5-cyclopropyl-6-cyclopropylmethoxy-pyrazine-2-carboxylic acid (Example 10 g; 100 mg, 0.42 mmol) and (2R)-2-amino-2,3-dimethyl-1-butanol (CAN 155158-75-1, 107.06 mg, 0.64 mmol) as starting materials, and isolated (20 mg, 14.04%) as off white sticky solid, LC-MS (UV peak area, ESI) 100%, 334.4 (M+H).

Example 52

5-Cyclopropyl-6-cyclopropylmethoxy-pyrazine-2-carboxylic acid ((S)-1-hydroxymethyl-1,2-dimethyl-propyl)-amide

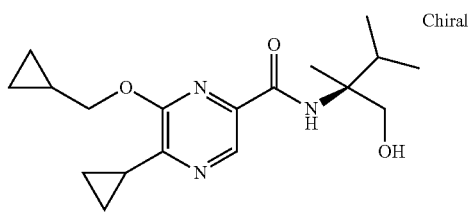 [SMILES: CC(C)[C@@](C)(CO)NC(=O)c1cnc(C2CC2)c(OCC2CC2)n1]

Chiral

The title compound was synthesized in analogy to Example 15, using 5-cyclopropyl-6-cyclopropylmethoxy-pyrazine-2-carboxylic acid (Example 10 g; 100 mg, 0.42 mmol) and (2S)-2-amino-2,3-dimethyl-1-butanol (CAN 956102-64-0, 107.06 mg, 0.64 mmol) as starting materials, and isolated (25 mg, 16.04%) as off white sticky solid, LC-MS (UV peak area, ESI) 90.02%, 334.4 (M+H).

Example 53

5-Cyclopropyl-6-cyclopropylmethoxy-pyrazine-2-carboxylic acid (1-ethyl-1-methylcarbamoyl-propyl)-amide

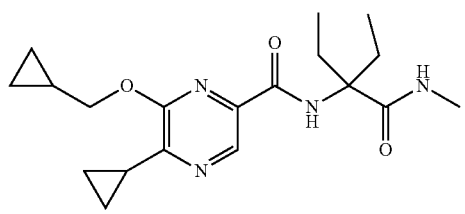 [SMILES: CCC(CC)(NC(=O)c1cnc(C2CC2)c(OCC2CC2)n1)C(=O)NC]

The title compound was synthesized in analogy to Example 15, using 5-cyclopropyl-6-cyclopropylmethoxy-pyrazine-2-carboxylic acid (Example 10 g; 100 mg, 0.42 mmol) and 2-amino-2-ethyl-N-methyl-butyramide (78.2 mg, 0.64 mmol) as starting materials, and isolated (12 mg, 9.44%) as colorless sticky solid, LC-MS (UV peak area, ESI) 97.47%, 361.4 (M+H).

Example 54

5-Cyclopropyl-6-cyclopropylmethoxy-pyrazine-2-carboxylic acid [1-methyl-1-(4-methyl-thiazol-2-yl)-ethyl]-amide

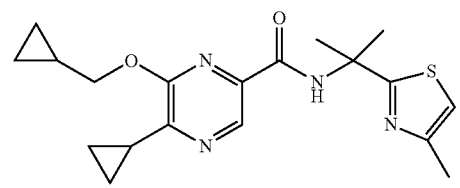 [SMILES: Cc1csc(C(C)(C)NC(=O)c2cnc(C3CC3)c(OCC3CC3)n2)n1]

The title compound was synthesized in analogy to Example 15, using 5-cyclopropyl-6-cyclopropylmethoxy-pyrazine-2-carboxylic acid (Example 10 g; 100 mg, 0.42 mmol) and α,α,4-trimethyl-2-thiazolemethanamine (CAN 859466-62-9, 78.2 mg, 0.64 mmol) as starting materials, and isolated (12 mg, 9.22%) as colorless sticky solid, LC-MS (UV peak area, ESI) 99.24%, 373.4 (M+H).

Example 55

6-Cyclopropylmethoxy-5-(3,3-difluoro-azetidin-1-yl)-pyrazine-2-carboxylic acid [1-methyl-1-(4-methyl-thiazol-2-yl)-ethyl]-amide

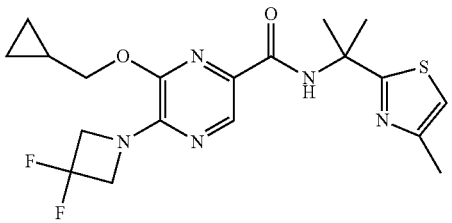 [SMILES: Cc1csc(C(C)(C)NC(=O)c2cnc(N3CC(F)(F)C3)c(OCC3CC3)n2)n1]

The title compound was synthesized in analogy to Example 15, using 6-cyclopropyl-methoxy-5-(3,3-difluoro-azetidin-1-yl)-pyrazine-2-carboxylic acid (Example 8d, 100 mg, 0.35 mmol) and α,α,4-trimethyl-2-thiazolemethanamine (87.28 mg, 0.53 mmol) as starting materials, and isolated (20 mg, 13.47%) as colorless sticky solid, LC-MS (UV peak area, ESI) 97.93%, 424.0 (M+H).

Example 56

6-Cyclopropylmethoxy-5-(3,3-difluoro-azetidin-1-yl)-pyrazine-2-carboxylic acid [(R)-1-(5-methyl-[1,2,4]oxadiazol-3-yl)-ethyl]amide

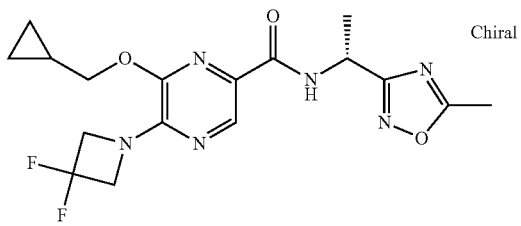 [SMILES: Cc1nc([C@@H](C)NC(=O)c2cnc(N3CC(F)(F)C3)c(OCC3CC3)n2)no1]

The title compound was synthesized in analogy to Example 15, using 6-cyclopropyl-methoxy-5-(3,3-difluoro-azetidin-1-yl)-pyrazine-2-carboxylic acid (Example 8d, 100 mg, 0.35 mmol) and (αR)-α,5-dimethyl-1,2,4-oxadiazole-3-methanamine (CAN 1150339-59-5, 66.7 mg, 0.52 mmol) as starting materials, and isolated (55 mg, 39.78%) as off white solid, LC-MS (UV peak area, ESI) 95.17%, 395.4 (M+H).

Example 57

5-Cyclopropyl-6-cyclopropylmethoxy-pyrazine-2-carboxylic acid [1-(5-amino-[1,2,4]oxadiazol-3-yl)-1-methyl-ethyl]-amide a) [1-(5-Amino-[1,2,4]oxadiazol-3-yl)-1-methyl-ethyl]-carbamic acid tert-butyl ester

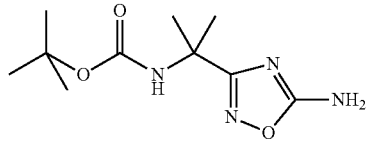 [SMILES: CC(C)(C)OC(=O)NC(C)(C)c1noc(N)n1]

(Z)-[1-(N-Hydroxycarbamimidoyl)-1-methyl-ethyl]-carbamic acid tert-butyl ester (CAN 1251430-04-2, 5.9 g, 27.2 mmol) was dissolved in DMF (11.8 mL). To this solution was added at room temperature piperidine-1-carbonitrile (3.29 g, 3.46 ml) and the reaction mixture was stirred for 2.5 hours at 130° C. After cooling the mixture was added to ice water (400 mL) and extracted with ethyl acetate (3×200 mL). The organic phases were washed with ice water, combined, dried with Na$_2$SO$_4$ and concentrated in vacuo. The residue was purified by chromatography (silica gel, 200 g, 1:1 ethyl acetate/n-heptane) to give the title compound (5.0 g, 76%) as white solid; LC-MS (UV peak area, ESI) 83%, 243.1453 (M+H).

b) 3-(1-Amino-1-methyl-ethyl)-[1,2,4]oxadiazol-5-ylamine hydrochloride (1:1)

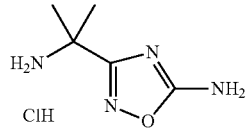

[1-(5-Amino-[1,2,4]oxadiazol-3-yl)-1-methyl-ethyl]-carbamic acid tert-butyl ester (1.6 g, 6.6 mmol) was dissolved in ethanol (30 mL). 4M HCl in dioxane (6.6 mL, 26.4 mmol) was added and the reaction mixture was stirred for 16 hours at room temperature. The mixture was in vacuo and dried to give the title compound (1.2 g, quant.) as off-white solid; MS (ESI) 143.0927(M+H).

c) 5-Cyclopropyl-6-cyclopropylmethoxy-pyrazine-2-carboxylic acid [1-(5-amino-[1,2,4]oxadiazol-3-yl)-1-methyl-ethyl]-amide

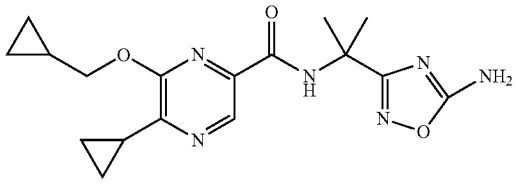 [SMILES: CC(C)(NC(=O)c1cnc(C2CC2)c(OCC2CC2)n1)c1noc(N)n1]

The title compound was synthesized in analogy to Example 6, using 5-cyclopropyl-6-cyclopropylmethoxy-pyrazine-2-carboxylic acid (Example 10 g) and 3-(1-amino-1-methyl-ethyl)-[1,2,4]oxadiazol-5-ylamine hydrochloride (1:1) (Example 57b) as starting materials, and isolated (57 mg, 75%) as off-white solid; LC-MS (UV peak area, ESI) 100%, 359.1825 (M+H).

Example 58

6-Cyclopropylmethoxy-5-(3,3-difluoro-azetidin-1-yl)-pyrazine-2-carboxylic acid [1-(5-amino-[1,2,4]oxadiazol-3-yl)-1-methyl-ethyl]-amide

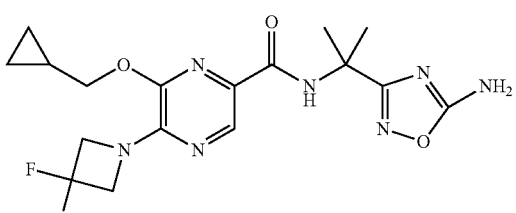

The title compound was synthesized in analogy to Example 6, using 6-cyclopropyl-methoxy-5-(3,3-difluoro-azetidin-1-yl)-pyrazine-2-carboxylic acid (Example 8d) and 3-(1-amino-1-methyl-ethyl)-[1,2,4]oxadiazol-5-ylamine hydrochloride (1:1) (Example 57b) as starting materials, and isolated (40 mg, 56%) as white solid; LC-MS (UV peak area, ESI) 100%, 410.1744 (M+H).

Example 59

6-Cyclopropylmethoxy-5-(3,3-difluoro-azetidin-1-yl)-pyrazine-2-carboxylic acid ((S)-1-carbamoyl-1-phenyl-ethyl)-amide

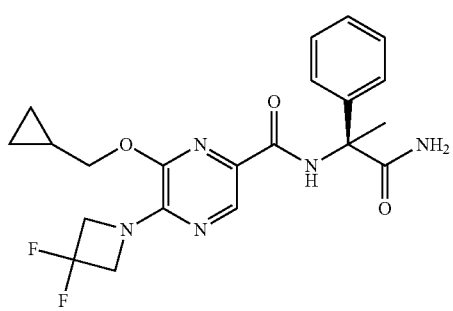

Chiral

The title compound was synthesized in analogy to Example 15, using 6-cyclopropyl-methoxy-5-(3,3-difluoro-azetidin-1-yl)-pyrazine-2-carboxylic acid (Example 8d, 100 mg, 0.35 mmol) and (S)-α-amino-α-methyl-benzeneacetamide (CAN 30358-55-5, 88.42 mg, 0.52 mmol) as starting materials, and isolated (85 mg, 56%) as white solid; LC-MS (UV peak area, ESI) 94.87%, 432.4 (M+H).

Example 60

6-Cyclopropylmethoxy-5-(3,3-difluoro-azetidin-1-yl)-pyrazine-2-carboxylic acid [2-cyclopropyl-1-methyl-1-(5-methyl-[1,2,4]oxadiazol-3-yl)-ethyl]-amide a) 2-Amino-3-cyclopropyl-2-methyl-propionitrile

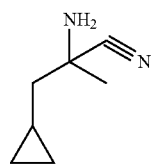

To a solution of 1-cyclopropyl-propan-2-one (CAN 4160-75-2; 1.0 g, 10.2 mmol) and aqueous ammonia (25% in water, 10 mL) in ethanol (10 mL) was added ammonium chloride (1.63 g, 30.6 mmol). The reaction mixture was stirred at ambient temperature for 1 hour. To this was added potassium cyanide (1 g, 15.30 mmol) portion wise, and the reaction mixture was stirred at ambient temperature for 12 h. Ice water (50 mL) was added and extracted with ethyl acetate (3×50 mL). The organic phases were washed with ice-water, combined, dried with $Na_2SO_4$ and concentrated in vacuo to give the title compound (0.8 g, 62.99%) as yellow oil; NMR (400 MHz, DMSO) δ=2.52 (bds, 2H); 1.6-1.5 (m, 1H); 1.49-1.4 (m, 1H); 1.39 (S, 3H); 0.85-0.75 (m, 1H); 0.49-0.44 (m, 2H); 0.16-0.14 (m, 2H).

b) (1-Cyano-2-cyclopropyl-1-methyl-ethyl)-carbamic acid tert-butyl ester

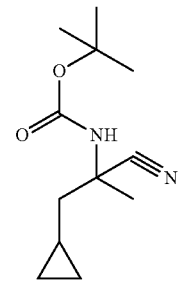 [SMILES: CC(C#N)(CC1CC1)NC(=O)OC(C)(C)C]

To a solution of 2-amino-3-cyclopropyl-2-methyl-propionitrile (1.0 g, 6.4 mmol) and triethyl amine (3.36 mL, 19.8 mmol) in dichloromethane (20 mL) was added di-tert-butyl dicarbonate (CAN 24424-99-5, 2.38 mL, 9.47 mmol). The reaction mixture was stirred at ambient temperature for 12 hours. The organic phase was washed with ice water, brine, dried with $Na_2SO_4$ and concentrated in vacuo. The residue was purified by chromatography (silica gel, 50 g, 1:9 ethyl acetate/n-hexane) to give the title compound (1.2 g, 66%) as light yellow liquid; LC-MS (UV peak area, ESI) 83%, 225.14 (M+H).

c) [2-Cyclopropyl-1-(N-hydroxycarbamimidoyl)-1-methyl-ethyl]-carbamic acid tert-butyl ester

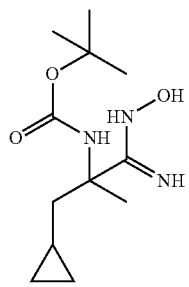 [SMILES: CC(C)(C)OC(=O)NC(C)(CC1CC1)C(=N)NO]

Sodium bicarbonate (247.52 mg, 2.94 mmol) was dissolved in water (2 mL) and hydroxylamine hydrochloride (204.747 mg, 2.94 mmol) was added. A solution of (1-cyano-2-cyclopropyl-1-methyl-ethyl)-carbamic acid tert-butyl ester (600 mg, 2.69 mmol) in ethanol (10 mL) was added thereto and the resulting reaction mixture was heated at 80° C. for 12 hours. After evaporation of solvents, the residue was dissolved with ethyl acetate (20 mL) and then filtered. The filtrate was concentrated in vacuo. The residue was purified by chromatography (silica gel, 25 g, 3:7 ethyl acetate/n-hexane) to give the title compound (450 mg, 66%) as white solid; LC-MS (UV peak area, ESI) 100%, 258.4 (M+H).

d) 2-Cyclopropyl-1-methyl-1-(5-methyl-[1,2,4]oxadiazol-3-yl)-ethyl]-carbamic acid tert-butyl ester

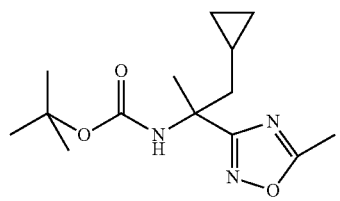 [SMILES: Cc1nc(C(C)(CC2CC2)NC(=O)OC(C)(C)C)no1]

A solution of [2-cyclopropyl-1-(N-hydroxycarbamimidoyl)-1-methyl-ethyl]-carbamic acid tert-butyl ester (300 mg, 1.16 mmol) in acetic anhydride (10 mL) was heated to 120° C. and stirred for 4 hours. After evaporation of solvents, the residue was purified by column chromatography (silica gel, 20 g, eluting with 20% ethyl acetate in petroleum ether) to give the title compound (0.2 g; 61%) as colorless sticky liquid; LC-MS (UV peak area, ESI) 90%, 282.2 (M+H).

e) 2-Cyclopropyl-1-methyl-1-(5-methyl-[1,2,4]oxadiazol-3-yl)-ethylamine

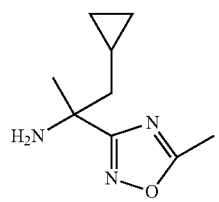

To a solution of 2-cyclopropyl-1-methyl-1-(5-methyl-[1,2,4]oxadiazol-3-yl)-ethyl]-carbamic acid tert-butyl ester (0.2 g, 0.7 mmol) in methanol (5 mL) was added hydrochloric acid (4N in dioxin, 0.87 mL, 3.5 mmol) and the reaction mixture was stirred at ambient temperature for 4 hours. Then water (20 mL) was added. The water phase was washed with ethyl acetate (2×20 mL) and adjusted with 2 M sodium hydroxide solution to pH=9~10. It was then extracted with ethyl acetate (2×20 mL). The organic layer was washed with brine (20 mL), dried over anhydrous $Na_2SO_4$ and concentrated to give crude product as a white solid (0.1 g, 78%); LC-MS (UV peak area, ESI) 80%, 182.0 (M+H).

f) 6-Cyclopropylmethoxy-5-(3,3-difluoro-azetidin-1-yl)-pyrazine-2-carboxylic acid [2-cyclopropyl-1-methyl-1-(5-methyl-[1,2,4]oxadiazol-3-yl)-ethyl]-amide

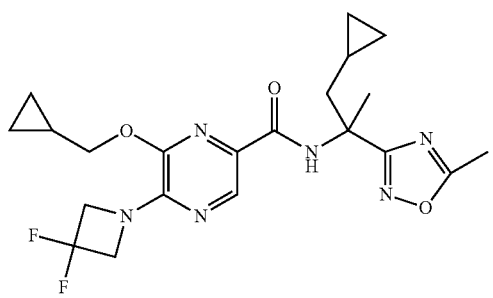 [SMILES: Cc1nc(C(C)(CC2CC2)NC(=O)c2cnc(N3CC(F)(F)C3)c(OCC3CC3)n2)no1]

The title compound was synthesized in analogy to Example 15, using 6-cyclopropyl-methoxy-5-(3,3-difluoro-azetidin-1-yl)-pyrazine-2-carboxylic acid (Example 8d, 100 mg, 0.35 mmol) and 2-cyclopropyl-1-methyl-1-(5-methyl-[1,2,4]oxadiazol-3-yl)-ethylamine (86.42 mg, 0.52 mmol) as starting materials, and isolated (60 mg, 38.2%) as white solid; LC-MS (UV peak area, ESI) 98.77%, 449.4 (M+H).

Example 61

6-Cyclopropylmethoxy-5-(3,3-difluoro-azetidin-1-yl)-pyrazine-2-carboxylic acid [1-cyclopropyl-1-(5-methyl-[1,2,4]oxadiazol-3-yl)-ethyl]-amide

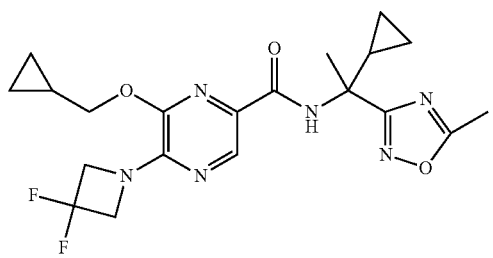 [SMILES: Cc1nc(C(C)(NC(=O)c2cnc(N3CC(F)(F)C3)c(OCC3CC3)n2)C2CC2)no1]

The title compound was synthesized in analogy to Example 15, using 6-cyclopropyl-methoxy-5-(3,3-difluoro-azetidin-1-yl)-pyrazine-2-carboxylic acid (Example 8d, 100 mg, 0.35 mmol) and 1-cyclopropyl-1-(5-methyl-[1,2,4]oxadiazol-3-yl)-ethylamine (88.42 mg, 0.52 mmol) as starting materials, and isolated (50 mg, 32.8%) as white solid; LC-MS (UV peak area, ESI) 97.16%, 435.2 (M+H).

Example 62

5-Cyclopropyl-6-cyclopropylmethoxy-pyrazine-2-carboxylic acid [1-cyclopropyl-1-(5-methyl-[1,2,4]oxadiazol-3-yl)-ethyl]-amide

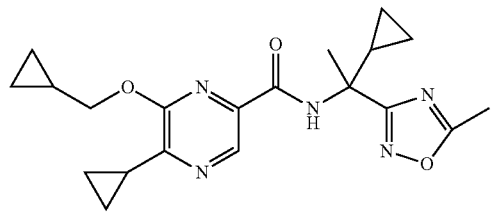 [SMILES: Cc1nc(C(C)(NC(=O)c2cnc(C3CC3)c(OCC3CC3)n2)C2CC2)no1]

The title compound was synthesized in analogy to Example 15, using 5-cyclopropyl-6-cyclopropylmethoxy-pyrazine-2-carboxylic acid (Example 10 g, 100 mg, 0.42 mmol) and α-cyclopropyl-α,5-dimethyl-1,2,4-oxadiazole-3-methanamine (CAN 1155536-64-3, 106.88 mg, 0.64 mmol) as starting materials, and isolated (12 mg, 7.3%) as white solid; LC-MS (UV peak area, ESI) 83.46%, 384.0 (M+H).

Example 63

5-Cyclopropyl-6-cyclopropylmethoxy-pyrazine-2-carboxylic acid [(S)-carbamoyl-(4-fluoro-phenyl)-methyl]-amide

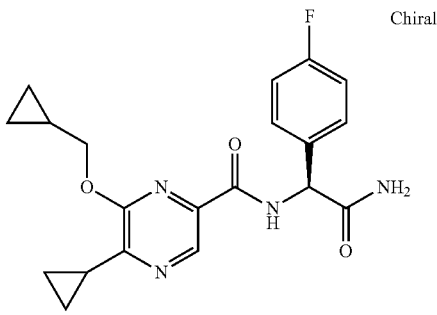 [SMILES: NC(=O)[C@@H](NC(=O)c1cnc(C2CC2)c(OCC2CC2)n1)c1ccc(F)cc1]

The title compound was synthesized in analogy to Example 15, using 5-cyclopropyl-6-cyclopropylmethoxy-pyrazine-2-carboxylic acid (Example 10 g, 100 mg, 0.42 mmol) and (S)-2-amino-2-(4-fluoro-phenyl)-acetamide (119.2 mg, 0.64 mmol) as starting materials, and isolated (10 mg, 6.3%) as white solid; LC-MS (UV peak area, ESI) 95.12%, 384.8 (M+H).

Example 64

6-Cyclopropylmethoxy-5-(3,3-difluoro-azetidin-1-yl)-pyrazine-2-carboxylic acid [(S)-carbamoyl-(4-fluoro-phenyl)-methyl]-amide

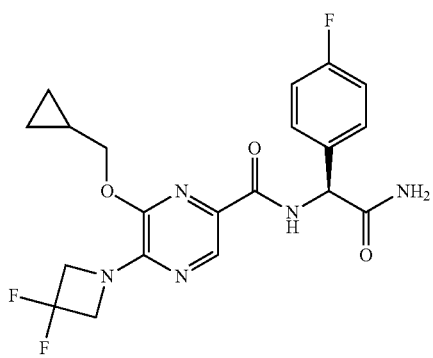

The title compound was synthesized in analogy to Example 15, using 6-cyclopropyl-methoxy-5-(3,3-difluoro-azetidin-1-yl)-pyrazine-2-carboxylic acid (Example 8d, 100 mg, 0.35 mmol) and (S)-2-amino-2-(4-fluoro-phenyl)-acetamide (88.4 mg, 0.52 mmol) as starting materials and isolated (20 mg, 13.15%) as white solid; LC-MS (UV peak area, ESI) 99.73%, 436.0 (M+H)$^+$.

Example 65

5-Cyclopropyl-6-cyclopropylmethoxy-pyrazine-2-carboxylic acid [(S)-2-cyclopropyl-1-(5-methyl-[1,2,4]oxadiazol-3-yl)-ethyl]-amide

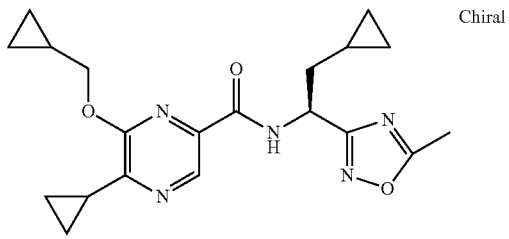 [SMILES: Cc1nc([C@H](CC2CC2)NC(=O)c2cnc(C3CC3)c(OCC3CC3)n2)no1]

5-Cyclopropyl-6-cyclopropylmethoxy-pyrazine-2-carboxylic acid (Example 10 g, 100 mg, 0.43 mmol) was suspended in DME (3 mL). Diethoxy-phosphorylformonitrile (226.0 mg, 0.80 mmol), DIEA (0.63 mL, 4.2 mmol) and (S)-2-cyclopropyl-1-(5-methyl-[1, 2, 4]oxadiazol-3-yl)-ethylamine (Example 20e, 82.2 mg, 0.64 mmol) were added and the reaction mixture was heated at 100° C. for 10 min under microwave condition. The mixture was extracted with ethyl acetate and water; the organic phase was dried over Na$_2$SO$_4$, filtered and concentrated in vacuo. The crude material was purified by reverse phase preparative HPLC (Xterra-RP18, 10 μ, 19×250 mm/acetonitrile/10 mM ammonium acetate in water) to give the desired product (20 mg, 11.72%) as white solid; LC-MS (UV peak area, ESI) 96.20%, 384.2 (M+H).

Example 66

(S)-2-{[6-Cyclopropylmethoxy-5-(3,3-difluoro-azetidin-1-yl)-pyrazine-2-carbonyl]-amino}-4-methyl-pentanoic acid methyl ester

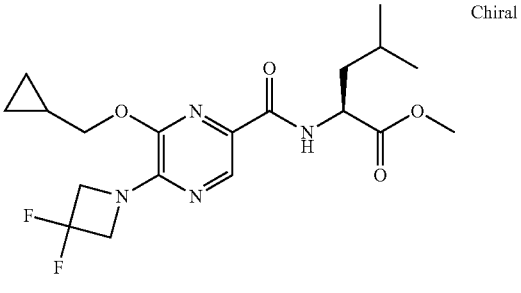 [SMILES: COC(=O)[C@H](CC(C)C)NC(=O)c1cnc(N2CC(F)(F)C2)c(OCC2CC2)n1]

The title compound was synthesized in analogy to Example 6 using 6-cyclopropyl-methoxy-5-(3,3-difluoro-azetidin-1-yl)-pyrazine-2-carboxylic acid (Example 8d, 300 mg, 1.05 mmol) and L-leucine methyl ester hydrochloride (1:1) (CAN 7517-19-3, 210 mg, 1.16 mmol) as starting materials and isolated (390 mg, 90%) as light yellow solid; LC-MS (UV peak area, ESI) 100%, 413.1997 (M+H)$^+$.

Example 67

6-Cyclopropylmethoxy-5-(3,3-difluoro-azetidin-1-yl)-pyrazine-2-carboxylic acid [(S)-3-methyl-1-(2,2,2-trifluoro-ethylcarbamoyl)-butyl]-amide

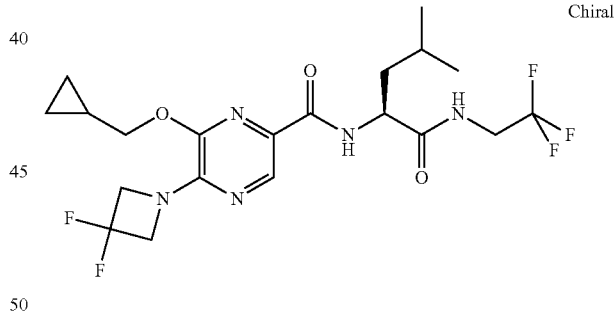

a) (S)-2-{[6-Cyclopropylmethoxy-5-(3,3-difluoro-azetidin-1-yl)-pyrazine-2-carbonyl]-amino}-4-methyl-pentanoic acid

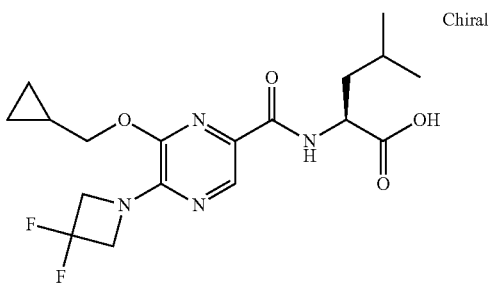 [SMILES: CC(C)C[C@H](NC(=O)c1cnc(N2CC(F)(F)C2)c(OCC2CC2)n1)C(=O)O]

To a solution of (S)-2-{[6-cyclopropylmethoxy-5-(3,3-difluoro-azetidin-1-yl)-pyrazine-2-carbonyl]-amino}-4-methyl-pentanoic acid methyl ester (355 mg, 0.86 mmol) in THF (18 mL) and H2O (6 mL) was added lithium hydroxide monohydrate (163 mg, 3.87 mmol) and the mixture was stirred at reflux temperature for 2 hours. The mixture was diluted with H2O (10 mL), acidified with hydrochloric acid (1N, 5 mL), and extracted with ethyl acetate (2×25 mL). The organic phases were combined, dried with Na2SO4 and concentrated in vacuo to give the title compound (334 mg, 97%) as white solid; LC-MS (UV peak area, ESI) 100%, 399.1842 (M+H)+.

b) 6-Cyclopropylmethoxy-5-(3,3-difluoro-azetidin-1-yl)-pyrazine-2-carboxylic acid [(S)-3-methyl-142,2,2-trifluoro-ethylcarbamoyl)-butyl]-amide (S)-2-{[6-Cyclopropylmethoxy-5-(3,3-difluoro-azetidin-1-yl)-pyrazine-2-carbonyl]-amino}-4-methyl-pentanoic acid (40 mg, 100 µmol) was suspended in DMF (2 mL). TBTU (35.5 mg, 110 µmol), DIEA (85.9 µl, 0.5 mmol) and 2,2,2-trifluoro-ethanamine hydrochloride (1:1) (CAN 373-88-6, 15 mg, 135 µmol) were added and the reaction mixture was stirred at room temperature for 16 hours. The mixture was concentrated in vacuo; ethyl acetate (3 mL) and 2N NaOH solution (2 mL) were added before eluting with ethyl acetate through ChemElut (10 g). The filtrate was concentrated in vacuo and purified by flash chromatography (silica gel, 10 g, 0% to 100% ethyl acetate in n-heptane) to give the desired product (36 mg, 75%) as white solid; LC-MS (UV peak area, ESI) 100%, 480.2035 (M+H).

Example 68

6-Cyclopropylmethoxy-5-(3,3-difluoro-azetidin-1-yl)-pyrazine-2-carboxylic acid [(S)-carbamoyl-(4-chloro-phenyl)-methyl]-amide

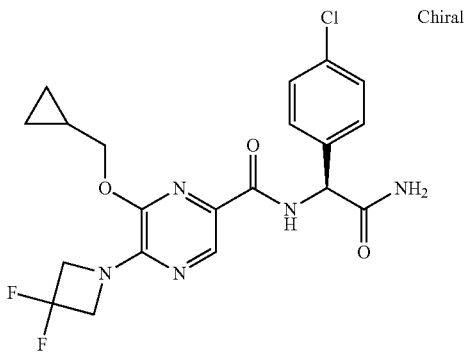 [SMILES: NC(=O)[C@@H](NC(=O)c1cnc(N2CC(F)(F)C2)c(OCC2CC2)n1)c1ccc(Cl)cc1]

The title compound was synthesized in analogy to Example 15, using 6-cyclopropyl-methoxy-5-(3,3-difluoro-azetidin-1-yl)-pyrazine-2-carboxylic acid (Example 8d, 100 mg, 0.35 mmol) and (S)-2-amino-2-(4-chloro-phenyl)-acetamide (67.3 mg, 0.52 mmol) as starting materials and isolated (20 mg, 12.6%) as white solid; LC-MS (UV peak area, ESI) 100%, 452.2 (M+H)+.

Example 69

5-Cyclopropyl-6-cyclopropylmethoxy-pyrazine-2-carboxylic acid (4-hydroxy-1,1-dimethyl-butyl)-amide

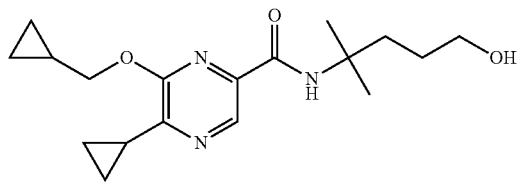 [SMILES: CC(C)(CCCO)NC(=O)c1cnc(C2CC2)c(OCC2CC2)n1]

5-Cyclopropyl-6-cyclopropylmethoxy-pyrazine-2-carboxylic acid (Example 10 g, 100 mg, 0.43 mmol) was suspended in DMF (3 mL). Mukaiyama Reagent (CAN 878-23-9, 233.8 mg, 0.85 mmol), DIEA (0.31 mL, 2.24 mmol) and 4-amino-4-methyl-pentan-1-ol (CAN 85054-53-1, 101.33 mg, 0.64 mmol) were added and the reaction mixture was stirred at room temperature for 12 hours. The mixture was extracted with ethyl acetate and water; the organic phase was dried over Na₂SO₄, filtered and concentrated in vacuo. The crude material was purified by reverse phase preparative HPLC (Xterra-RP18, 10 µ, 19×250 mm/acetonitrile/10 mM ammonium acetate in water) to give the desired product (100 mg, 70.26%) as colorless sticky liquid; LC-MS (UV peak area, ESI) 96.12%, 334.0 (M+H).

Example 70

5-Cyclopropyl-6-cyclopropylmethoxy-pyrazine-2-carboxylic acid (1,1-dimethyl-3-pyridin-4-yl-propyl)-amide

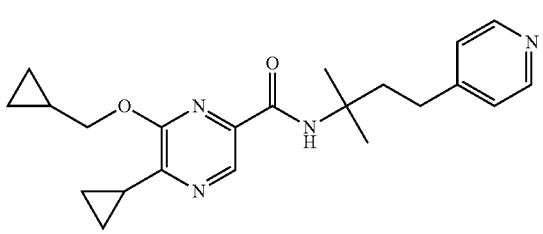 [SMILES: CC(C)(CCc1ccncc1)NC(=O)c1cnc(C2CC2)c(OCC2CC2)n1]

The title compound was synthesized in analogy to Example 69, using 5-cyclopropyl-6-cyclopropylmethoxy-pyrazine-2-carboxylic acid (Example 10 g, 50 mg, 0.21 mmol) and 1,1-dimethyl-3-pyridin-4-yl-propylamine (55 mg, 0.32 mmol) as starting materials and isolated (60.0 mg, 74%) as white solid; LC-MS (UV peak area, ESI) 94.93%, 380.0 (M+H)+.

Example 71

5-Cyclopropyl-6-cyclopropylmethoxy-pyrazine-2-carboxylic acid [1,1-dimethyl-2-(5-methyl-2-phenyl-oxazol-4-yl)-ethyl]-amide

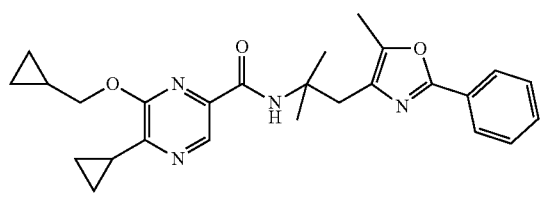 [SMILES: Cc1oc(-c2ccccc2)nc1CC(C)(C)NC(=O)c1cnc(C2CC2)c(OCC2CC2)n1]

The title compound was synthesized in analogy to Example 69, using 5-cyclopropyl-6-cyclopropylmethoxy-pyrazine-2-carboxylic acid (Example 10 g, 50 mg, 0.21 mmol) and 1,1-dimethyl-2-(5-methyl-2-phenyl-oxazol-4-yl)-ethylamine (57.2 mg, 0.32 mmol) as starting materials and isolated (75 mg, 73.6%) as white solid; LC-MS (UV peak area, ESI) 92.82%, 446.8 (M+H)$^+$.

Example 72

5-Cyclopropyl-6-cyclopropylmethoxy-pyrazine-2-carboxylic acid (1,1-dimethyl-3-pyridin-4-yl-butyl)-amide

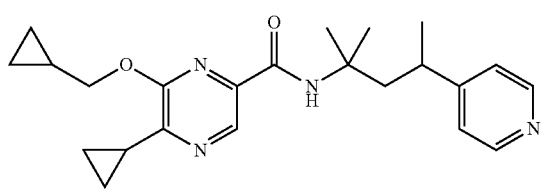 [SMILES: CC(CC(C)(C)NC(=O)c1cnc(C2CC2)c(OCC2CC2)n1)c1ccncc1]

The title compound was synthesized in analogy to Example 69, using 5-cyclopropyl-6-cyclopropylmethoxy-pyrazine-2-carboxylic acid (Example 10 g 10 mg, 0.043 mmol) and 1,1-dimethyl-3-pyridin-4-yl-butylamine (12 mg, 0.064 mmol) as starting materials and isolated (10 mg, 59.38%) as white solid; LC-MS (UV peak area, ESI) 99.2%, 395.2 (M+H)$^+$.

Example 73

1-{[6-Cyclopropylmethoxy-5-(3,3-difluoro-azetidin-1-yl)-pyrazine-2-carbonyl]-amino}-cyclobutanecarboxylic acid methyl ester

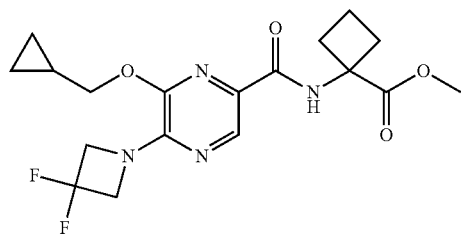 [SMILES: COC(=O)C1(NC(=O)c2cnc(N3CC(F)(F)C3)c(OCC3CC3)n2)CCC1]

The title compound was synthesized in analogy to Example 6 using 6-cyclopropyl-methoxy-5-(3,3-difluoro-azetidin-1-yl)-pyrazine-2-carboxylic acid (Example 8d, 100 mg, 0.35 mmol) and 1-amino-cyclobutanecarboxylic acid methyl ester hydrochloride (1:1) (CAN 92398-47-5, 64 mg, 0.39 mmol) as starting materials and isolated (111 mg, 80%) as white solid; LC-MS (UV peak area, ESI) 100%, 397.1683 (M+H)$^+$.

Example 74

5-Cyclopropyl-6-cyclopropylmethoxy-pyrazine-2-carboxylic acid [1-methyl-1-(5-methyl-thiazol-2-yl)-ethyl]-amide

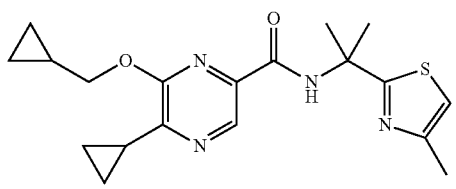 [SMILES: Cc1csc(C(C)(C)NC(=O)c2cnc(C3CC3)c(OCC3CC3)n2)n1]

The title compound was synthesized in analogy to Example 69, using 5-cyclopropyl-6-cyclopropylmethoxy-pyrazine-2-carboxylic acid (Example 10 g, 100 mg, 0.42 mmol) and 1-methyl-1-(5-methyl-thiazol-2-yl)-ethylamine (100 mg, 0.64 mmol) as starting materials and isolated (29 mg, 18.3%) as white solid; LC-MS (UV peak area, ESI) 94.85%, 372.8 (M+H)$^+$.

Example 75

6-Cyclopropylmethoxy-5-(3,3-difluoro-azetidin-1-yl)-pyrazine-2-carboxylic acid [1-methyl-1-(5-methyl-thiazol-2-yl)-ethyl]-amide

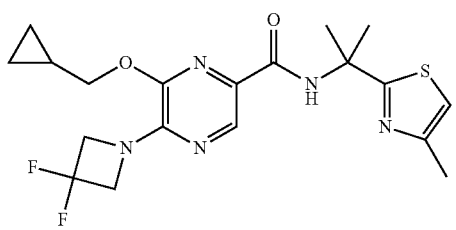 [SMILES: Cc1csc(C(C)(C)NC(=O)c2cnc(N3CC(F)(F)C3)c(OCC3CC3)n2)n1]

The title compound was synthesized in analogy to Example 15, using 6-cyclopropyl-methoxy-5-(3,3-difluoro-azetidin-1-yl)-pyrazine-2-carboxylic acid (Example 8d, 100 mg, 0.35 mmol) and 1-methyl-1-(5-methyl-thiazol-2-yl)-ethylamine (82.3 mg, 0.526 mmol) as starting materials and isolated (26 mg, 17.5%) as white solid; LC-MS (UV peak area, ESI) 86.27%, 423.8 (M+H)$^+$.

Example 76

5-Cyclopropyl-6-cyclopropylmethoxy-pyrazine-2-carboxylic acid ((S)-1-carbamoylmethyl-2-methyl-propyl)-amide

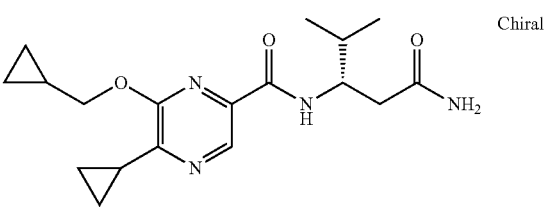 [SMILES: CC(C)[C@H](CC(N)=O)NC(=O)c1cnc(C2CC2)c(OCC2CC2)n1]

The title compound was synthesized in analogy to Example 6 using 5-cyclopropyl-6-cyclopropylmethoxy-pyrazine-2-carboxylic acid (Example 10 g, 50 mg, 0.21 mmol) and (3S)-3-amino-4-methyl-pentanamide monohydrochloride (CAN 173336-51-1, 39 mg, 0.24 mmol) as starting materials and isolated (55 mg, 74%) as light yellow solid; LC-MS (UV peak area, ESI) 98%, 347.2082 (M+H)$^+$.

Example 77

6-Cyclopropylmethoxy-5-(3,3-difluoro-azetidin-1-yl)-pyrazine-2-carboxylic acid ((S)-1-carbamoylm-ethyl-2-methyl-propyl)-amide

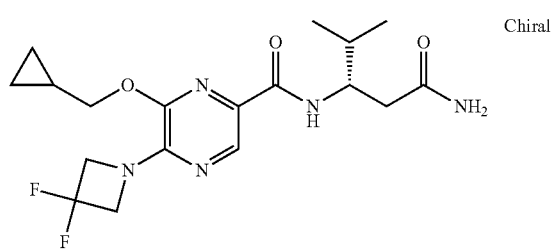 [SMILES: CC(C)[C@H](CC(N)=O)NC(=O)c1cnc(N2CC(F)(F)C2)c(OCC2CC2)n1]

The title compound was synthesized in analogy to Example 6 using 6-cyclopropyl-methoxy-5-(3,3-difluoro-azetidin-1-yl)-pyrazine-2-carboxylic acid (Example 8d, 50 mg, 0.21 mmol) and (3S)-3-amino-4-methyl-pentanamide monohydrochloride (CAN 173336-51-1, 39 mg, 0.24 mmol) as starting materials and isolated (52 mg, 74%) as white solid; LC-MS (UV peak area, ESI) 100%, 398.1998 (M+H)$^+$.

Example 78

(+)-6-Cyclopropylmethoxy-5-(3,3-difluoro-azetidin-1-yl)-pyrazine-2-carboxylic acid [2-cyclopropyl-1-methyl-1-(5-methyl-[1,2,4]oxadiazol-3-yl)-ethyl]-amide

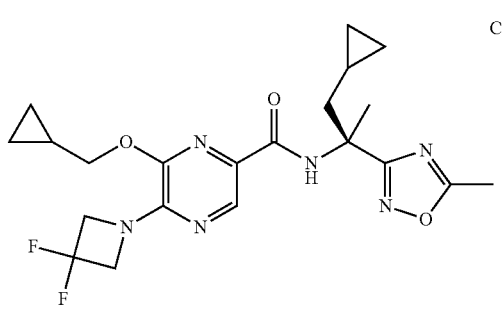

The title compound was isolated by chiral chromatography of 6-cyclopropylmethoxy-5-(3,3-difluoro-azetidin-1-yl)-pyrazine-2-carboxylic acid [2-cyclopropyl-1-methyl-1-(5-methyl-[1,2,4]oxadiazol-3-yl)-ethyl]-amide (Example 600 on ChiralPak AD using heptane/5% 2-propanol as eluent. The (+)-enantiomer was isolated. LC-MS (UV peak area/ESI) 94%, 449.2112 (M+H)$^+$, $\alpha_D^{20}$ (MeOH)=+36.8°.

Example 79

(−)-6-Cyclopropylmethoxy-5-(3,3-difluoro-azetidin-1-yl)-pyrazine-2-carboxylic acid [2-cyclopropyl-1-methyl-1-(5-methyl-[1,2,4]oxadiazol-3-yl)-ethyl]-amide

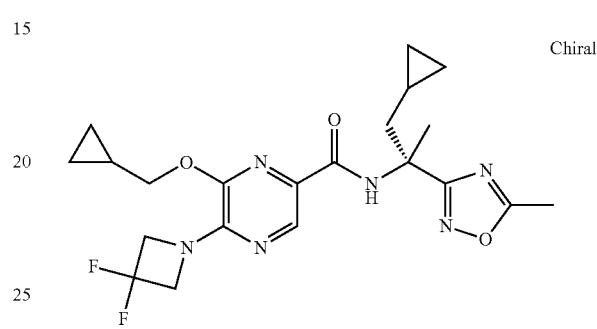

The title compound was isolated by chiral chromatography of 6-cyclopropylmethoxy-5-(3,3-difluoro-azetidin-1-yl)-pyrazine-2-carboxylic acid [2-cyclopropyl-1-methyl-1-(5-methyl-[1,2,4]oxadiazol-3-yl)-ethyl]-amide (Example 600 on ChiralPak AD using heptane/5% 2-propanol as eluent. The (−)-enantiomer was isolated. LC-MS (UV peak area/ESI) 96%, 449.2113 (M+H)$^+$, $\alpha_D^{20}$ (MeOH)=−27.7°.

Example 80

2-Cyclopropyl-2-{[6-cyclopropylmethoxy-5-(3,3-difluoro-azetidin-1-yl)-pyrazine-2-carbonyl]-amino}-propionic acid methyl ester

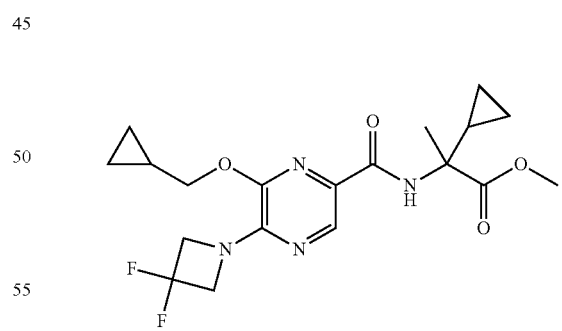

The title compound was synthesized in analogy to Example 6 using 6-cyclopropyl-methoxy-5-(3,3-difluoro-azetidin-1-yl)-pyrazine-2-carboxylic acid (Example 8d, 200 mg, 0.70 mmol) and α-amino-α-methyl-cyclopropaneacetic acid methyl ester hydrochloride (1:1) (CAN 1333675-34-5, 139 mg, 0.77 mmol) as starting materials and isolated (256 mg, 89%) as light yellow oil; LC-MS (UV peak area, ESI) 100%, 411.1838 (M+H)$^+$.

Example 81

(+)-6-Cyclopropylmethoxy-5-(3,3-difluoro-azetidin-1-yl)-pyrazine-2-carboxylic acid ((1R,2S)-rel-2-carbamoyl-cyclohexyl)-amide

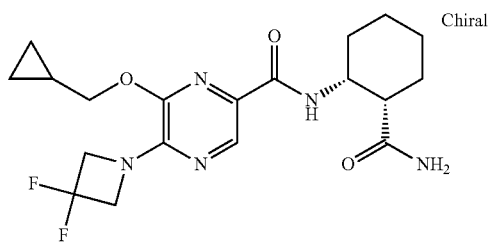 [SMILES: NC(=O)[C@H]1CCCC[C@H]1NC(=O)c1cnc(N2CC(F)(F)C2)c(OCC2CC2)n1]

a) 6-Cyclopropylmethoxy-5-(3,3-difluoro-azetidin-1-yl)-pyrazine-2-carboxylic acid (1R,2S)-rel-2-carbamoyl-cyclohexyl)-amide

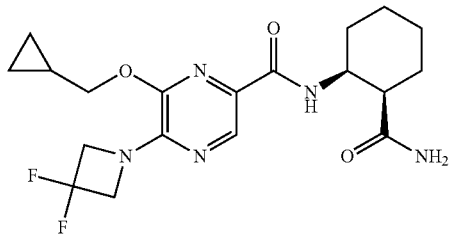 [SMILES: NC(=O)[C@@H]1CCCC[C@@H]1NC(=O)c1cnc(N2CC(F)(F)C2)c(OCC2CC2)n1]

The title compound was synthesized in analogy to Example 6 using 6-cyclopropyl-methoxy-5-(3,3-difluoro-azetidin-1-yl)-pyrazine-2-carboxylic acid (Example 8d, 100 mg, 0.35 mmol) and (1R,2S)-rel-2-amino-cyclohexanecarboxamide (CAN 24717-01-9, 55 mg, 0.39 mmol) as starting materials and isolated (122 mg, 85%) as white solid; LC-MS (UV peak area, ESI) 100%, 410.1998 (M+H)$^+$.

b) (+)-6-Cyclopropylmethoxy-5-(3,3-difluoro-azetidin-1-yl)-pyrazine-2-carboxylic acid (1R,2S)-rel-2-carbamoyl-cyclohexyl)-amide The title compound was isolated by chiral chromatography of 6-cyclopropylmethoxy-5-(3,3-difluoro-azetidin-1-yl)-pyrazine-2-carboxylic acid (1R,2S)-rel-2-carbamoyl-cyclohexyl)-amide (Example 81a) on ChiralPak AD using heptane/20% ethanol as eluent. The (+)-enantiomer was isolated. LC-MS (UV peak area/ESI) 100%, 410.1996 (M+H)$^+$, $\alpha_D^{20}$ (MeOH)=+73.5°.

Example 82

(−)-5-Cyclopropyl-6-cyclopropylmethoxy-pyrazine-2-carboxylic acid cis-2-carbamoyl-cyclohexyl)-amide

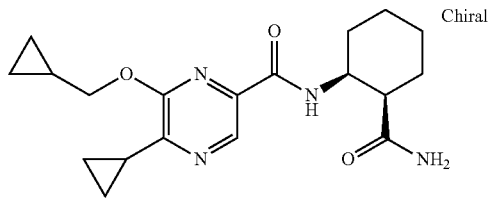 [SMILES: NC(=O)[C@@H]1CCCC[C@@H]1NC(=O)c1cnc(C2CC2)c(OCC2CC2)n1]

a) 5-Cyclopropyl-6-cyclopropylmethoxy-pyrazine-2-carboxylic acid ((1S,2R)-rel-2-carbamoyl-cyclohexyl)-amide

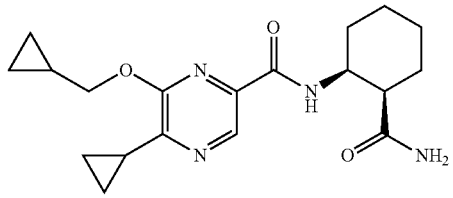 [SMILES: NC(=O)[C@@H]1CCCC[C@@H]1NC(=O)c1cnc(C2CC2)c(OCC2CC2)n1]

The title compound was synthesized in analogy to Example 6 using 5-cyclopropyl-6-cyclopropylmethoxy-pyrazine-2-carboxylic acid (Example 10 g, 100 mg, 0.43 mmol) and (1R,2S)-rel-2-amino-cyclohexanecarboxamide (CAN 24717-01-9, 67 mg, 0.47 mmol) as starting materials and isolated (155 mg, quant.) as off-white solid; LC-MS (UV peak area, ESI) 97%, 359.2078 (M+H)$^+$.

b) (−)-5-Cyclopropyl-6-cyclopropylmethoxy-pyrazine-2-carboxylic acid cis-2-carbamoyl-cyclohexyl)-amide The title compound was isolated by chiral chromatography of 5-cyclopropyl-6-cyclopropylmethoxy-pyrazine-2-carboxylic acid ((1S,2R)-rel-2-carbamoyl-cyclohexyl)-amide (Example 82a) on ChiralPak AD using heptane/20% ethanol as eluent. The (−)-enantiomer was isolated. LC-MS (UV peak area/ESI) 100%, 359.2077 (M+H)$^+$, $\alpha_D^{20}$ (MeOH)=−60.6°.

Example 83

(+)-5-Cyclopropyl-6-cyclopropylmethoxy-pyrazine-2-carboxylic acid cis-2-carbamoyl-cyclohexyl)-amide

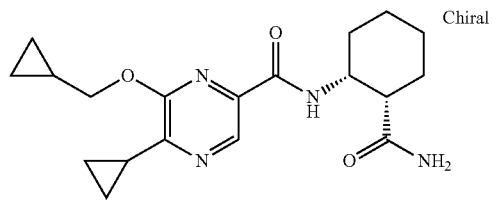 [SMILES: NC(=O)[C@H]1CCCC[C@H]1NC(=O)c1cnc(C2CC2)c(OCC2CC2)n1]

The title compound was isolated by chiral chromatography of 5-cyclopropyl-6-cyclopropylmethoxy-pyrazine-2-carboxylic acid ((1S,2R)-rel-2-carbamoyl-cyclohexyl)-amide (Example 82a) on ChiralPak AD using heptane/20% ethanol as eluent. The (+)-enantiomer was isolated. LC-MS (UV peak area/ESI) 100%, 359.2084 (M+H)$^+$, $\alpha_D^{20}$ (MeOH)=+57.8°.

Example 84

5-Cyclopropyl-6-cyclopropylmethoxy-pyrazine-2-carboxylic acid (3-carbamoylmethyl-oxetan-3-yl)-amide

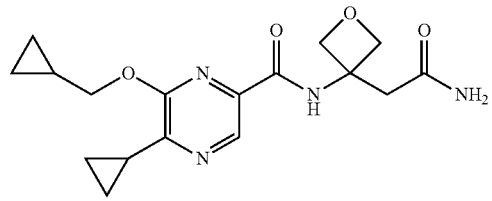 [SMILES: NC(=O)CC1(NC(=O)c2cnc(C3CC3)c(OCC3CC3)n2)COC1]

a) 2-(3-Amino-oxetan-3-yl)-acetamide

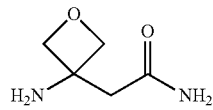

To a solution of 3-amino-3-oxetaneacetic acid ethyl ester (400 mg, 2.51 mmol) in toluene (8.0 mL) was added ammonium hydroxide in water (25%, 8.0 mL, 51.4 mmol). The mixture was stirred in a closed tube at room temperature for 6 days. Solvents were removed in vacuo and remaining water was removed by azeotropic distillation with toluene. The residue was dried in high-vacuum at 40° C. to give the desired product (290 mg, 89%) as white solid; GC-MS (ESI), 131.0817 (M+H).

b) 5-Cyclopropyl-6-cyclopropylmethoxy-pyrazine-2-carboxylic acid (3-carbamoylmethyl-oxetan-3-yl)-amide The title compound was synthesized in analogy to Example 6 using 5-cyclopropyl-6-cyclopropylmethoxy-pyrazine-2-carboxylic acid (Example 10 g, 50 mg, 0.21 mmol) and 2-(3-amino-oxetan-3-yl)-acetamide (31 mg, 0.24 mmol) as starting materials and isolated (30 mg, 41%) as white solid; LC-MS (UV peak area, ESI) 100%, 347.1710 (M+H)$^+$.

Example 85

6-Cyclopropylmethoxy-5-(3,3-difluoro-azetidin-1-yl)-pyrazine-2-carboxylic acid (3-carbamoylmethyl-oxetan-3-yl)-amide

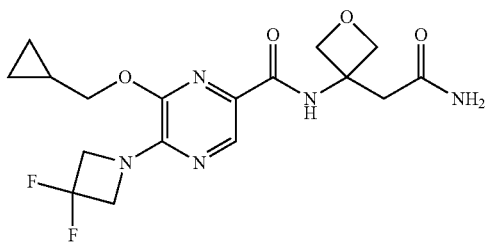 [SMILES: NC(=O)CC1(NC(=O)c2cnc(N3CC(F)(F)C3)c(OCC3CC3)n2)COC1]

The title compound was synthesized in analogy to Example 6 using 6-cyclopropyl-methoxy-5-(3,3-difluoro-azetidin-1-yl)-pyrazine-2-carboxylic acid (Example 8d, 50 mg, 0.18 mmol) and 2-(3-amino-oxetan-3-yl)-acetamide (Example 85a, 25 mg, 0.19 mmol) as starting materials and isolated (37 mg, 53%) as white solid; LC-MS (UV peak area, ESI) 100%, 398.1641 (M+H)$^+$.

Example 86

(+)-6-Cyclopropylmethoxy-5-(3,3-difluoro-azetidin-1-yl)-pyrazine-2-carboxylic acid [1-cyclopropyl-1-(5-methyl-[1,2,4]oxadiazol-3-yl)-ethyl]-amide

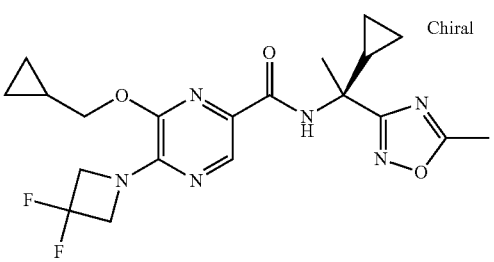 [SMILES: Cc1nc([C@@](C)(NC(=O)c2cnc(N3CC(F)(F)C3)c(OCC3CC3)n2)C2CC2)no1]

The title compound was isolated by chiral chromatography of 6-cyclopropylmethoxy-5-(3,3-difluoro-azetidin-1-yl)-pyrazine-2-carboxylic acid [1-cyclopropyl-1-(5-methyl-[1,2,4]oxadiazol-3-yl)-ethyl]-amide (Example 61) on ChiralPak AD using heptane/15% 2-propanol as eluent. The (+)-enantiomer was isolated. LC-MS (UV peak area/ESI) 100%, 435.1945 (M+H)$^+$, $\alpha_D^{20}$ (MeOH)=+70.4°.

Example 87

(−)-6-Cyclopropylmethoxy-5-(3,3-difluoro-azetidin-1-yl)-pyrazine-2-carboxylic acid [1-cyclopropyl-1-(5-methyl-[1,2,4]oxadiazol-3-yl)-ethyl]-amide

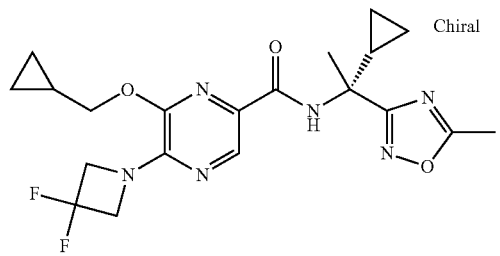 [SMILES: Cc1nc([C@](C)(NC(=O)c2cnc(N3CC(F)(F)C3)c(OCC3CC3)n2)C2CC2)no1]

The title compound was isolated by chiral chromatography of 6-cyclopropylmethoxy-5-(3,3-difluoro-azetidin-1-yl)-pyrazine-2-carboxylic acid [1-cyclopropyl-1-(5-methyl-[1,2,4]oxadiazol-3-yl)-ethyl]-amide (Example 61) on ChiralPak AD using heptane/15% 2-propanol as eluent. The (−)-enantiomer was isolated. LC-MS (UV peak area/ESI) 100%, 435.1945 (M+H)$^+$, $\alpha_D^{20}$ (MeOH)=−68.8°.

Example 88

6-Cyclopropylmethoxy-5-(3,3-difluoro-azetidin-1-yl)-pyrazine-2-carboxylic acid (1-carbamoyl-2-methyl-propyl)-amide

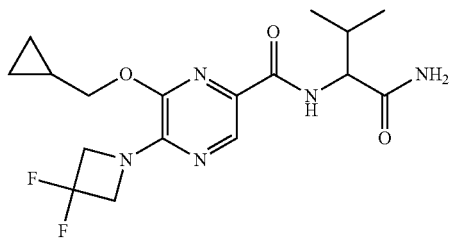 [SMILES: CC(C)C(NC(=O)c1cnc(N2CC(F)(F)C2)c(OCC2CC2)n1)C(N)=O]

The title compound was synthesized in analogy to Example 69, using 6-cyclopropyl-methoxy-5-(3,3-difluoro-azetidin-1-yl)-pyrazine-2-carboxylic acid (Example 8d, 100 mg, 0.35 mmol) and 2-amino-3-methyl-butyramide (CAN 13474-14-1, 61.2 mg, 0.52 mmol) as starting materials and isolated (40 mg, 49.73%) as white solid; LC-MS (UV peak area, ESI) 97.95%, 384.0 (M+H)$^+$.

Example 89

6-Cyclopropylmethoxy-5-(3,3-difluoro-azetidin-1-yl)-pyrazine-2-carboxylic acid (1-carbamoyl-cyclohexyl)-amide

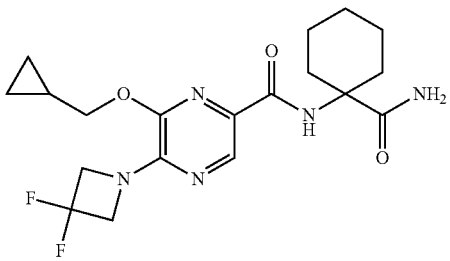 [SMILES: NC(=O)C1(NC(=O)c2cnc(N3CC(F)(F)C3)c(OCC3CC3)n2)CCCCC1]

The title compound was synthesized in analogy to Example 69, using 6-cyclopropyl-methoxy-5-(3,3-difluoro-azetidin-1-yl)-pyrazine-2-carboxylic acid (Example 8d, 100 mg, 0.35 mmol) and 1-amino-cyclohexanecarboxylic acid amide hydrochloride (CAN 17704-77-7, 74.73 mg, 0.52 mmol) as starting materials and isolated (100 mg, 69.9%) as white solid; LC-MS (UV peak area, ESI) 95.07%, 410.0 $(M+H)^+$.

Example 90

6-Cyclopropylmethoxy-5-(3,3-difluoro-azetidin-1-yl)-pyrazine-2-carboxylic acid (1-hydroxymethyl-cyclohexyl)-amide

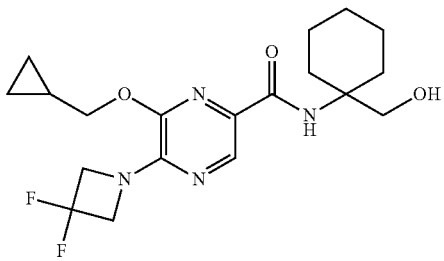 [SMILES: O=C(NC1(CO)CCCCC1)c1cnc(N2CC(F)(F)C2)c(OCC2CC2)n1]

The title compound was synthesized in analogy to Example 69, using 6-cyclopropyl-methoxy-5-(3,3-difluoro-azetidin-1-yl)-pyrazine-2-carboxylic acid (Example 8d, 100 mg, 0.35 mmol) and 1-amino-cyclohexanecarboxylic acid amide hydrochloride (CAN 17704-77-7, 74.73 mg, 0.52 mmol) as starting materials and isolated (100 mg, 69.9%) as white solid; LC-MS (UV peak area, ESI) 95.07%, 410.0 $(M+H)^+$.

Example 91

6-Cyclopropylmethoxy-5-(3,3-difluoro-azetidin-1-yl)-pyrazine-2-carboxylic acid (1-dimethylcarbamoyl-2-methyl-propyl)-amide

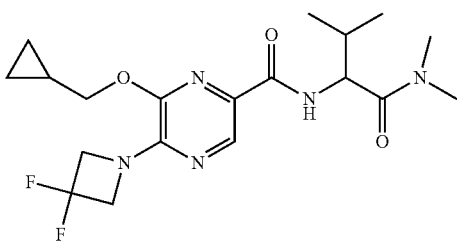 [SMILES: CC(C)C(NC(=O)c1cnc(N2CC(F)(F)C2)c(OCC2CC2)n1)C(=O)N(C)C]

The title compound was synthesized in analogy to Example 69, using 6-cyclopropyl-methoxy-5-(3,3-difluoro-azetidin-1-yl)-pyrazine-2-carboxylic acid (Example 8d, 100 mg, 0.35 mmol) and 2-amino-3,N,N-trimethyl-butyramide hydrochloride (CAN 1257848-66-0, 75.7 mg, 0.52 mmol) as starting materials and isolated (50.6 mg, 34.63%) as white solid; LC-MS (UV peak area, ESI) 98.97%, 412.0 $(M+H)^+$.

Example 92

5-Cyclopropyl-6-cyclopropylmethoxy-pyrazine-2-carboxylic acid (1-dimethylcarbamoyl-2-methyl-propyl)-amide

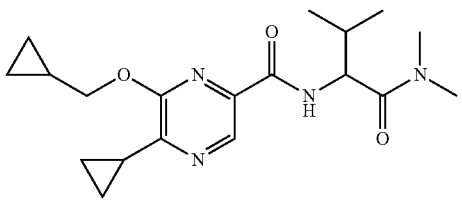 [SMILES: CC(C)C(NC(=O)c1cnc(C2CC2)c(OCC2CC2)n1)C(=O)N(C)C]

The title compound was synthesized in analogy to Example 69, using 5-cyclopropyl-6-cyclopropylmethoxy-pyrazine-2-carboxylic acid (Example 10 g, 80 mg, 0.34 mmol) and 2-amino-3,N,N-trimethyl-butyramide hydrochloride (CAN 1257848-66-0, 40.1 mg, 0.27 mmol) as starting materials and isolated (35 mg, 28.4%) as white solid; LC-MS (UV peak area, ESI) 93.77%, 361.0 $(M+H)^+$.

Example 93

6-Cyclopropylmethoxy-5-(3,3-difluoro-azetidin-1-yl)-pyrazine-2-carboxylic acid (5-chloro-thiophen-2-yl)-amide

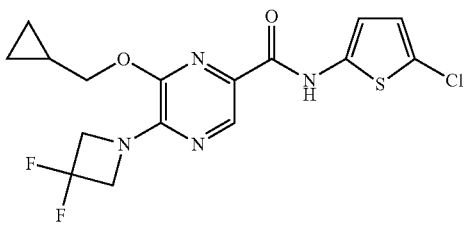 [SMILES: O=C(Nc1ccc(Cl)s1)c1cnc(N2CC(F)(F)C2)c(OCC2CC2)n1]

The title compound was synthesized in analogy to Example 69, using 6-cyclopropyl-methoxy-5-(3,3-difluoro-azetidin-1-yl)-pyrazine-2-carboxylic acid (Example 8d, 100 mg, 0.35 mmol) and 5-chloro-thiophen-2-ylamine (CAN 63806-78-0, 18.6 mg, 0.14 mmol) as starting materials and isolated (12 mg, 17.06%) as white solid; LC-MS (UV peak area, ESI) 95.2%, 401.2 $(M+H)^+$.

Example 94

5-Cyclopropyl-6-cyclopropylmethoxy-pyrazine-2-carboxylic acid (1-hydroxymethyl-cyclohexyl)-amide

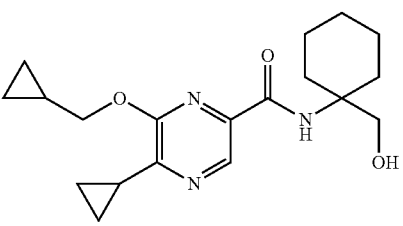 [SMILES: O=C(NC1(CO)CCCCC1)c1cnc(C2CC2)c(OCC2CC2)n1]

The title compound was synthesized in analogy to Example 69, using 5-cyclopropyl-6-cyclopropylmethoxy-pyrazine-2-carboxylic acid (Example 10 g, 50 mg, 0.214 mmol) and (1-amino-cyclohexyl)-methanol hydrochloride (CAN 5460-68-4, 22.8 mg, 0.17 mmol) as starting materials and isolated (46 mg, 62.32%) as white solid; LC-MS (UV peak area, ESI) 96.49%, 346.0 (M+H)+.

Example 95

5-Cyclopropyl-6-cyclopropylmethoxy-pyrazine-2-carboxylic acid (3-methoxy-1,1-dimethyl-propyl)-amide

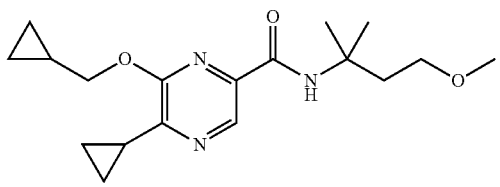 [SMILES: COCCC(C)(C)NC(=O)c1cnc(C2CC2)c(OCC2CC2)n1]

The title compound was synthesized in analogy to Example 69 using 5-cyclopropyl-6-cyclopropylmethoxy-pyrazine-2-carboxylic acid (Example 10 g, 50 mg, 0.214 mmol) and 3-methoxy-1,1-dimethyl-propylamine (CAN 889765-21-3, 50 mg, 0.32 mmol) as starting materials and isolated (40 mg, 56.14%) as white solid; LC-MS (UV peak area, ESI) 99.87%, 333.8 (M+H)+.

Example 96

6-Cyclopropylmethoxy-5-(3,3-difluoro-azetidin-1-yl)-pyrazine-2-carboxylic acid (2-cyclobutyl-1-methylcarbamoyl-ethyl)-amide

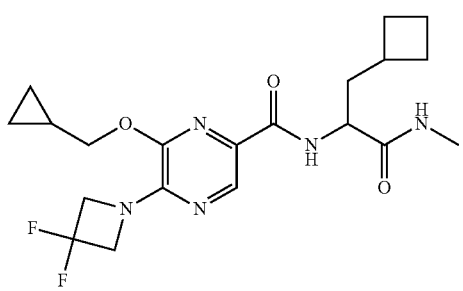 [SMILES: CNC(=O)C(CC1CCC1)NC(=O)c1cnc(N2CC(F)(F)C2)c(OCC2CC2)n1]

The title compound was synthesized in analogy to Example 69, using 6-cyclopropyl-methoxy-5-(3,3-difluoro-azetidin-1-yl)-pyrazine-2-carboxylic acid (Example 8d, 50 mg, 0.17 mmol) and 2-amino-3-cyclobutyl-N-methyl-propionamide (34 mg, 01.7 mmol) as starting materials and isolated (12 mg, 16.15%) as white solid; LC-MS (UV peak area, ESI) 99.07%, 422.4 (M+H)+.

Example 97

6-Cyclopropylmethoxy-5-(3,3-difluoro-azetidin-1-yl)-pyrazine-2-carboxylic acid (2-cyclobutyl-1-dimethylcarbamoyl-ethyl)-amide

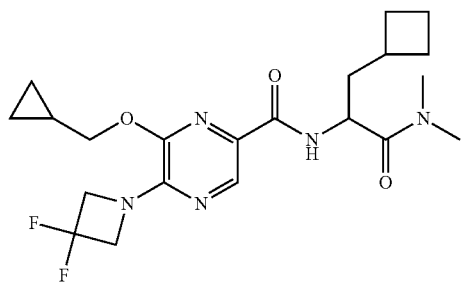 [SMILES: CN(C)C(=O)C(CC1CCC1)NC(=O)c1cnc(N2CC(F)(F)C2)c(OCC2CC2)n1]

The title compound was synthesized in analogy to Example 69, using 6-cyclopropyl-methoxy-5-(3,3-difluoro-azetidin-1-yl)-pyrazine-2-carboxylic acid (Example 8d, 50 mg, 01.7 mmol) and 2-amino-3-cyclobutyl-N,N-dimethyl-propionamide (36.3 mg, 0.17 mmol) as starting materials and isolated (12 mg, 15.63%) as white solid; LC-MS (UV peak area, ESI) 99.52%, 438.2 (M+H)+.

Example 98

5-Cyclopropyl-6-cyclopropylmethoxy-pyrazine-2-carboxylic acid (2-cyclobutyl-1-methylcarbamoyl-ethyl)-amide

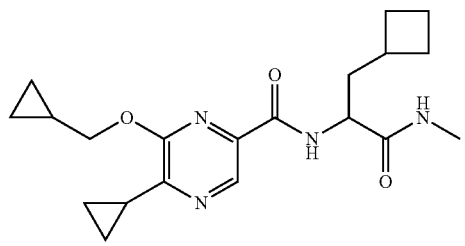 [SMILES: CNC(=O)C(CC1CCC1)NC(=O)c1cnc(C2CC2)c(OCC2CC2)n1]

The title compound was synthesized in analogy to Example 69, using 5-cyclopropyl-6-cyclopropylmethoxy-pyrazine-2-carboxylic acid (Example 10 g, 50 mg, 0.21 mmol) and 2-amino-3-cyclobutyl-N-methyl-propionamide (41.2 mg, 0.32 mmol) as starting materials and isolated (20 mg, 25.16%) as white solid; LC-MS (UV peak area, ESI) 99.32%, 373.2 (M+H)+.

Example 99

6-Cyclopropylmethoxy-5-(3,3-difluoro-azetidin-1-yl)-pyrazine-2-carboxylic acid (3-methoxy-1,1-dimethyl-propyl)-amide

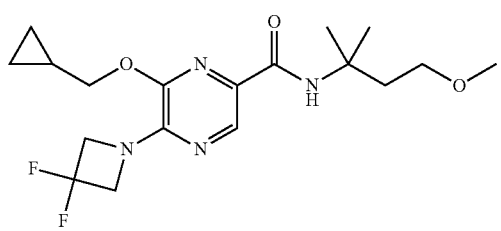 [SMILES: COCCC(C)(C)NC(=O)c1cnc(N2CC(F)(F)C2)c(OCC2CC2)n1]

The title compound was synthesized in analogy to Example 69, using 6-cyclopropyl-methoxy-5-(3,3-difluoro-azetidin-1-yl)-pyrazine-2-carboxylic acid (Example 8d, 50 mg, 0.17 mmol) and 3-methoxy-1,1-dimethyl-propylamine (CAN 889765-21-3, 27.28 mg, 0.175 mmol) as starting materials and isolated (55.3 mg, 67.4%) as white solid; LC-MS (UV peak area, ESI) 99.69%, 385.2 (M+H)+.

Example 100

6-Cyclopropylmethoxy-5-(3,3-difluoro-azetidin-1-yl)-pyrazine-2-carboxylic acid (1-cyclobutylmethyl-2-hydroxy-ethyl)-amide

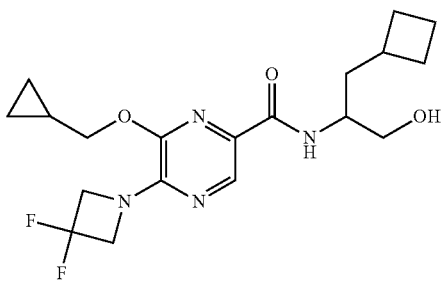 [SMILES: O=C(NC(CO)CC1CCC1)c1cnc(N2CC(F)(F)C2)c(OCC2CC2)n1]

The title compound was synthesized in analogy to Example 69, using 6-cyclopropyl-methoxy-5-(3,3-difluoro-azetidin-1-yl)-pyrazine-2-carboxylic acid (Example 8d, 50 mg, 0.17 mmol) and 2-amino-3-cyclobutyl-propan-1-ol (27.2 mg, 0.17 mmol) as starting materials and isolated (35 mg, 50.32%) as white solid; LC-MS (UV peak area, ESI) 99.21%, 397.2 (M+H)+

Example 101

6-Cyclopropylmethoxy-5-(3,3-difluoro-azetidin-1-yl)-pyrazine-2-carboxylic acid (1-carbamoyl-2-cyclobutyl-ethyl)-amide

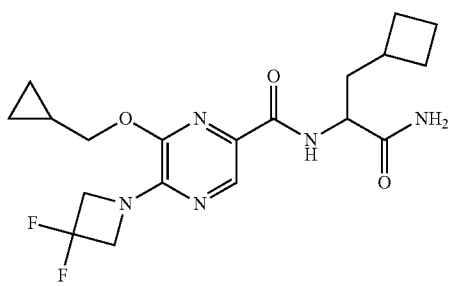 [SMILES: NC(=O)C(CC1CCC1)NC(=O)c1cnc(N2CC(F)(F)C2)c(OCC2CC2)n1]

The title compound was synthesized in analogy to Example 69, using 6-cyclopropyl-methoxy-5-(3,3-difluoro-azetidin-1-yl)-pyrazine-2-carboxylic acid (Example 8d, 100 mg, 0.35 mmol) and 2-amino-3-cyclobutyl-propionamide (105.1 mg, 0.52 mmol) as starting materials and isolated (30 mg, 21%) as white solid; LC-MS (UV peak area, ESI) 98.96%, 410.4 (M+H)+.

Example 102

6-Cyclopropylmethoxy-5-(3,3-difluoro-azetidin-1-yl)-pyrazine-2-carboxylic acid (1,1-dimethyl-3-phenyl-propyl)-amide

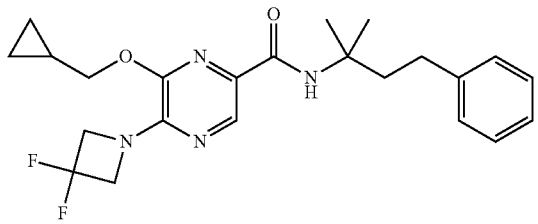 [SMILES: CC(C)(CCc1ccccc1)NC(=O)c1cnc(N2CC(F)(F)C2)c(OCC2CC2)n1]

The title compound was synthesized in analogy to Example 69, using 6-cyclopropyl-methoxy-5-(3,3-difluoro-azetidin-1-yl)-pyrazine-2-carboxylic acid (Example 8d, 50 mg, 0.17 mmol) and 1,1-dimethyl-3-phenyl-propylamine (52.88 mg, 0.32 mmol) as starting materials and isolated (50 mg, 54.9%) as white solid; LC-MS (UV peak area, ESI) 91.57%, 431.0 (M+H)+.

Example 103

5-Cyclopropyl-6-cyclopropylmethoxy-pyrazine-2-carboxylic acid (2-cyclobutyl-1-dimethylcarbamoyl-ethyl)-amide

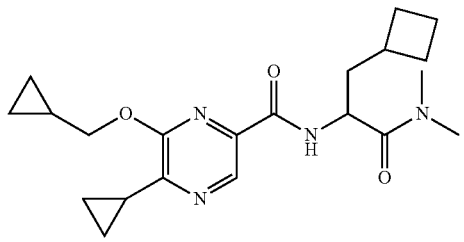 [SMILES: CN(C)C(=O)C(CC1CCC1)NC(=O)c1cnc(C2CC2)c(OCC2CC2)n1]

The title compound was synthesized in analogy to Example 69, using 5-cyclopropyl-6-cyclopropylmethoxy-pyrazine-2-carboxylic acid (Example 10 g, 50 mg, 0.21 mmol) and 2-amino-3-cyclobutyl-N,N-dimethyl-propionamide (54.48 mg, 0.32 mmol) as starting materials and isolated (20 mg, 24.3%) as white solid; LC-MS (UV peak area, ESI) 100%, 387.2 (M+H)+.

Example 104

5-Cyclopropyl-6-cyclopropylmethoxy-pyrazine-2-carboxylic acid (1-carbamoyl-2-cyclobutyl-ethyl)-amide

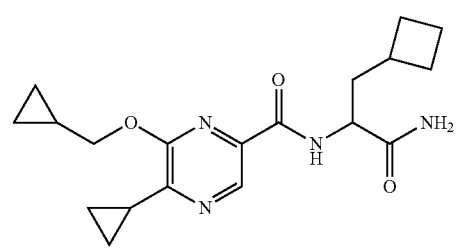 [SMILES: NC(=O)C(CC1CCC1)NC(=O)c1cnc(C2CC2)c(OCC2CC2)n1]

The title compound was synthesized in analogy to Example 69, using 5-cyclopropyl-6-cyclopropylmethoxy-pyrazine-2-carboxylic acid (Example 10 g, 50 mg, 0.21 mmol) and 2-amino-3-cyclobutyl-propionamide (52.5 mg, 0.26 mmol) as starting materials and isolated (30 mg, 39.4%) as white solid; LC-MS (UV peak area, ESI) 99.04%%, 357.4 (M−H)'.

Example 105

5-Cyclopropyl-6-cyclopropylmethoxy-pyrazine-2-carboxylic acid (1-cyclobutylmethyl-2-hydroxy-ethyl)-amide

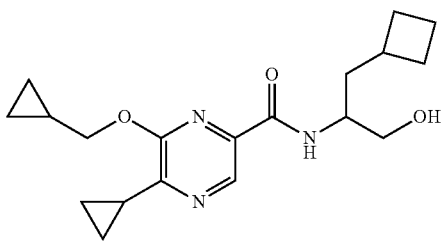 [SMILES: O=C(NC(CO)CC1CCC1)c1cnc(C2CC2)c(OCC2CC2)n1]

The title compound was synthesized in analogy to Example 69, using 5-cyclopropyl-6-cyclopropylmethoxy-pyrazine-2-carboxylic acid (Example 10 g, 50 mg, 0.21 mmol) and 2-amino-3-cyclobutyl-propan-1-ol (38.7 mg, 0.3 mmol) as starting materials and isolated (30 mg, 41%) as white solid; LC-MS (UV peak area, ESI) 99.69%, 346.2 (M+H)+.

Example 106

(5-Cyclopropyl-6-cyclopropylmethoxy-pyrazine-2-carboxylic acid (2-carbamoyl-1,1-dimethyl-ethyl)-amide

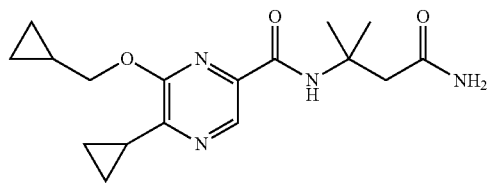 [SMILES: CC(C)(CC(N)=O)NC(=O)c1cnc(C2CC2)c(OCC2CC2)n1]

The title compound was synthesized in analogy to Example 6, using 5-cyclopropyl-6-cyclopropylmethoxy-pyrazine-2-carboxylic acid (Example 10 g, 50 mg, 0.21 mmol) and 3-amino-3-methyl-butanamide hydrochloride (1:1) (CAN 173336-86-2, 35.8 mg, 0.235 mmol) as starting materials and isolated (56 mg, 79%) as light yellow solid; LC-MS (UV peak area, ESI) 100%, 333.1926 (M+H)+.

Example 107

6-Cyclopropylmethoxy-5-(3,3-difluoro-azetidin-1-yl)-pyrazine-2-carboxylic acid (2-carbamoyl-1,1-dimethyl-ethyl)-amide

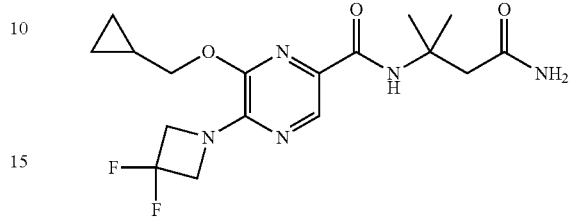

The title compound was synthesized in analogy to Example 6, using 6-cyclopropyl-methoxy-5-(3,3-difluoro-azetidin-1-yl)-pyrazine-2-carboxylic acid (Example 8d, 50 mg, 0.175 mmol) and 3-amino-3-methyl-butanamide hydrochloride (1:1) (CAN 173336-86-2, 29.4 mg, 0.193 mmol) as starting materials and isolated (38 mg, 57%) as white solid; LC-MS (UV peak area, ESI) 100%, 384.1849 (M+H)+.

Example 108

Pharmacological Tests

The following tests were carried out in order to determine the activity of the compounds of formula I:

Radioligand Binding Assay

The affinity of the compounds of the invention for cannabinoid CB1 receptors was determined using recommended amounts of membrane preparations (PerkinElmer) of human embryonic kidney (HEK) cells expressing the human CNR1 or CNR2 receptors in conjunction with 1.5 or 2.6 nM [3H]-CP-55,940 (Perkin Elmer) as radioligand, respectively. Binding was performed in binding buffer (50 mM Tris, 5 mM MgCl2, 2.5 mM EDTA, and 0.5% (wt/vol) fatty acid free BSA, pH 7.4 for CB1 receptor and 50 mM Tris, 5 mM $MgCl_2$, 2.5 mM EGTA, and 0.1% (wt/vol) fatty acid free BSA, pH 7.4 for CB2 receptor) in a total volume of 0.2 ml for 1 h at 30° C. shaking The reaction was terminated by rapid filtration through microfiltration plates coated with 0.5% polyethylenimine (UniFilter GF/B filter plate; Packard). Bound radioactivity was analyzed for Ki using nonlinear regression analysis (Activity Base, ID Business Solution, Limited), with the Kd values for [3H]CP55,940 determined from saturation experiments. The compounds of formula (I) show an excellent affinity for the CB2 receptor with affinities below 10 μM, more particularly of 1 nM to 3 μM and most particularly of 1 nM to 100 nM.

The compounds according to formula I have an activity in the above assay (Ki) particularly of 0.5 nM to 10 μM, more particularly of 0.5 nM to 3 μM and most particularly of 0.5 nM to 100 nM.

cAMP Assay

CHO cells expressing human CB1 or CB2 receptors are seeded 17-24 hours prior to the experiment 50.000 cells per well in a black 96 well plate with flat clear bottom (Corning Costar #3904) in DMEM (Invitrogen No. 31331), 1×HT supplement, with 10% fetal calf serum and incubated at 5% $CO_2$ and 37° C. in a humidified incubator. The growth medium was exchanged with Krebs Ringer Bicarbonate buffer with 1 mM IBMX and incubated at 30° C. for 30 min. Compounds were added to a final assay volume of 100 μl and incubated for 30 min at 30° C. Using the cAMP-Nano-TRF detection kit the assay (Roche Diagnostics) was stopped by the addition of 50 μl lysis reagent (Tris, NaCl, 1.5% Triton X100, 2.5% NP40, 10% $NaN_3$) and 50 μl detection solutions (20 μM mAb Alexa700-cAMP 1:1, and 48 μM Ruthenium-2-AHA-cAMP) and shaken for 2 h at room temperature. The time-resolved energy transfer is measured by a TRF reader (Evotec Technologies GmbH), equipped with a ND:YAG laser as excitation source. The plate is measured twice with the excitation at 355 nm and at the emission with a delay of 100 ns and a gate of 100 ns, total exposure time 10s at 730 (bandwidth 30 nm) or 645 nm (bandwidth 75 nm), respectively. The FRET signal is calculated as follows: FRET=T730-Alexa730-P(T645-B645) with P=Ru730-B730/Ru645-B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 μM to 0.13 nM cAMP.

$EC_{50}$ values were determined using Activity Base analysis (ID Business Solution, Limited). The $EC_{50}$ values for a wide range of cannabinoid agonists generated from this assay were in agreement with the values published in the scientific literature.

All compounds are CB2 agonists with $EC_{50}$ below 3 uM and selectivity versus CB1 in the corresponding assay of at least 10 fold For example, the following compounds showed the following human $EC_{50}$ values in the functional cAMP assay described above (ND: not determined):

| Example | human CB2 $EC_{50}$ [μM] | human CB1 $EC_{50}$ [μM] |
| --- | --- | --- |
| 1 | 0.0881 | 1.1485 |
| 2 | 0.1037 | >10 |
| 3 | 0.1559 | >10 |
| 4 | 0.1076 | >10 |
| 5 | 0.1398 | >10 |
| 6 | 0.048 | 0.8921 |
| 7 | 0.2552 | >10 |
| 8 | 0.0185 | >10 |
| 9 | 0.0879 | 1.2858 |
| 10 | 0.2574 | >10 |
| 11 | 0.124 | 3.3204 |
| 12 | 0.0852 | >10 |
| 13 | 0.0634 | >10 |
| 14 | 0.0068 | 0.1552 |
| 15 | 0.1413 | >10 |
| 16 | 0.0369 | >10 |
| 17 | 0.1979 | >10 |
| 18 | 0.3272 | >10 |
| 19 | 0.0535 | >10 |
| 20 | 0.0284 | >10 |
| 21 | 0.0613 | >10 |
| 22 | 0.093 | >10 |
| 23 | 0.0017 | 0.1574 |
| 24 | 0.1992 | >10 |
| 25 | 0.0146 | >10 |
| 26 | 0.0135 | >10 |
| 27 | 0.0027 | >10 |
| 28 | 0.0435 | >10 |
| 29 | 0.0041 | 1.5697 |
| 30 | 0.0014 | 0.2548 |
| 31 | 0.1238 | >10 |
| 32 | 0.0596 | >10 |
| 33 | 0.0118 | >10 |
| 34 | 0.0136 | >10 |
| 35 | 0.0433 | >10 |
| 36 | 0.0096 | >10 |
| 37 | 0.1084 | 1.6449 |
| 38 | 0.0444 | >10 |
| 39 | 0.011 | >10 |
| 40 | 0.0308 | >10 |
| 41 | 0.518 | >10 |
| 42 | 0.028 | >10 |
| 43 | 0.0409 | >10 |
| 44 | 0.4418 | >10 |
| 45 | 0.0514 | >10 |
| 46 | 0.2906 | >10 |
| 47 | 0.0729 | >10 |
| 48 | 0.0244 | >10 |
| 49 | 0.1066 | >10 |
| 50 | 0.0074 | >10 |
| 51 | 0.1374 | >10 |
| 52 | 0.0369 | >10 |
| 53 | 0.0151 | >10 |
| 54 | 0.1877 | >10 |
| 55 | 0.022 | >10 |
| 56 | 0.0725 | >10 |
| 57 | 0.2214 | >10 |
| 58 | 0.178 | >10 |
| 59 | 0.0492 | >10 |
| 60 | 0.0146 | >10 |
| 61 | 0.0179 | >10 |
| 62 | 0.0228 | 1.6484 |
| 63 | 0.0966 | ND |
| 64 | 0.0312 | ND |
| 65 | 0.0207 | ND |
| 66 | 0.0004 | ND |
| 67 | 0.0576 | ND |
| 68 | 0.1159 | ND |
| 69 | 0.0474 | ND |
| 70 | 0.2803 | ND |
| 71 | 0.2014 | ND |
| 72 | 0.0926 | ND |
| 73 | 0.0205 | ND |
| 74 | 0.0116 | >10 |
| 75 | 0.0056 | ND |
| 76 | 0.0163 | ND |
| 77 | 0.0065 | ND |
| 78 | 0.0174 | ND |
| 79 | 0.004 | ND |
| 80 | 0.0007 | >10 |
| 81 | 0.0312 | ND |
| 82 | 0.2573 | ND |
| 83 | 0.0444 | ND |
| 84 | 0.0146 | >10 |
| 85 | 0.0058 | >10 |
| 86 | 0.0237 | >10 |
| 87 | 0.0132 | >10 |
| 88 | 0.0791 | >10 |
| 89 | 0.0706 | >10 |
| 90 | 0.0018 | >10 |
| 91 | 0.0205 | >10 |
| 92 | 0.0086 | >10 |
| 93 | 0.0741 | >10 |
| 94 | 0.012 | >10 |
| 95 | 0.0224 | >10 |
| 96 | 0.0517 | >10 |
| 97 | 0.0204 | >10 |
| 98 | 0.0593 | >10 |
| 99 | 0.0103 | >10 |
| 100 | 0.0073 | >10 |
| 101 | 0.0056 | >10 |
| 102 | 0.0025 | >10 |
| 103 | 0.0192 | >10 |
| 104 | 0.0429 | >10 |
| 105 | 0.037 | >10 |
| 106 | 0.0432 | >10 |
| 107 | 0.0118 | 0.874 |

β-Arrestin Translocation Assay-PathHunter™ (DiscoveRx)

PathHunter™ β-arrestin CHO-K1 CNR1 cell line (catalog number #93-0200C2) and the β-arrestin CHO-K1 CNR2 cell line (catalog number #93-0706C2) were purchased from DiscoveRx Corporation. The cell line was engineered to express the β-galactosidase EA fragment fused to β-arrestin and the ProLink complementary peptide fused to the target receptor. The PathHunter™ protein complementation assay (DiscoveRx Corporation #93-0001) was performed according to the manufacturer's protocol. Assay plates were seeded containing 7500 (CNR[1]) and 10000 (CNR2) cells in 384 well plates (Corning Costar #3707, white, clear bottom) in 20 μL cell plating reagent 2 (Discoverx #93-0563R2A). After incubation at 37° C. (5% $CO_2$, 95% relative humidity) overnight, 5 μl of test compound was added (1% final DMSO concentration) and the incubation continued at 30° C. for 90 min. Detection reagent (12 μl) was then added and the incubation continued at room temperature for 60 min. Plates were then analyzed for a chemiluminescent signal using a Victor $^3$V reader (Perkin Elmer).

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

The invention claimed is:
1. A compound, selected from the group consisting of:
6-(3-Chloro-phenyl)-5-cyclopropyl-pyrazine-2-carboxylic acid [1-methyl-1-(5-methyl-[1,2,4]oxadiazol-3-yl)-ethyl]amide;
6-(3-Chloro-phenyl)-5-cyclopropyl-pyrazine-2-carboxylic acid (cyano-dimethyl-methyl)-amide;
6-(3-Chloro-phenyl)-5-cyclopropyl-pyrazine-2-carboxylic acid [1-(5-methyl-[1,2,4]oxadiazol-3-yl)-cyclobutyl]-amide;
6-(3-Chloro-phenyl)-5-(3,3-difluoro-azetidin-1-yl)-pyrazine-2-carboxylic acid [1-methyl-1-(5-methyl-[1,2,4]oxadiazol-3-yl)-ethyl]-amide;
5-Azetidin-1-yl-6-(3-chloro-phenyl)-pyrazine-2-carboxylic acid [1-methyl-1-(5-methyl-[1,2,4]oxadiazol-3-yl)-ethyl]-amide;
6-(3-Chloro-phenyl)-5-cyclopropyl-pyrazine-2-carboxylic acid (1-methyl-1-thiazol-2-yl-ethyl)-amide;
6-(3-Chloro-phenyl)-5-cyclopropyl-pyrazine-2-carboxylic acid piperidin-1-ylamide;
6-Cyclopropylmethoxy-5-(3,3-difluoro-azetidin-1-yl)-pyrazine-2-carboxylic acid ((S)-2,2-dimethyl-1-methylcarbamoyl-propyl)-amide;
6-Cyclopropylmethoxy-5-(3,3-difluoro-azetidin-1-yl)-pyrazine-2-carboxylic acid [1-(5-methyl-[1,2,4]oxadiazol-3-yl)-cyclobutyl]-amide;
5-Cyclopropyl-6-cyclopropylmethoxy-pyrazine-2-carboxylic acid (3-hydroxy-1,1-dimethyl-propyl)-amide;
5-Cyclopropyl-6-cyclopropylmethoxy-pyrazine-2-carboxylic acid (1-hydroxymethyl-cyclobutyl)-amide;
5-Cyclopropyl-6-cyclopropylmethoxy-pyrazine-2-carboxylic acid [1-(5-methyl-[1,2,4]oxadiazol-3-yl)-cyclobutyl]-amide;
5-Cyclopropyl-6-cyclopropylmethoxy-pyrazine-2-carboxylic acid (1-hydroxymethyl-1-methyl-propyl)-amide;
5-Cyclopropyl-6-cyclopropylmethoxy-pyrazine-2-carboxylic acid ((S)-2,2-dimethyl-1-methylcarbamoyl-propyl)-amide;
5-Cyclopropyl-6-cyclopropylmethoxy-pyrazine-2-carboxylic acid ((S)-carbamoyl-phenyl-methyl)-amide;
6-Cyclopropylmethoxy-5-(3,3-difluoro-azetidin-1-yl)-pyrazine-2-carboxylic acid ((S)-1-cyclopropylmethyl-2-hydroxy-2-methyl-propyl)-amide;
5-Cyclopropyl-6-cyclopropylmethoxy-pyrazine-2-carboxylic acid ((S)-1-cyclopropylmethyl-2-hydroxy-2-methyl-propyl)-amide;
5-Cyclopropyl-6-cyclopropylmethoxy-pyrazine-2-carboxylic acid piperidin-1-ylamide;

5-Cyclopropyl-6-cyclopropylmethoxy-pyrazine-2-carboxylic acid (1-hydroxymethyl-2,2-dimethyl-propyl)-amide;
6-Cyclopropylmethoxy-5-(3,3-difluoro-azetidin-1-yl)-pyrazine-2-carboxylic acid [(S)-2-cyclopropyl-1-(5-methyl-[1,2,4]oxadiazol-3-yl)-ethyl]-amide;
6-Cyclopropylmethoxy-5-(3,3-difluoro-azetidin-1-yl)-pyrazine-2-carboxylic acid (1-cyclopropyl-2-hydroxy-ethyl)-amide;
6-Cyclopropylmethoxy-5-(3,3-difluoro-azetidin-1-yl)-pyrazine-2-carboxylic acid ((S)-carbamoyl-phenyl-methyl)-amide;
(S)-2-[(5-Cyclopropyl-6-cyclopropylmethoxy-pyrazine-2-carbonyl)-amino]-3,3-dimethyl-butyric acid methyl ester;
5-Cyclopropyl-6-cyclopropylmethoxy-pyrazine-2-carboxylic acid ((S)-2-cyclopropyl-1-methylcarbamoyl-ethyl)-amide;
5-Cyclopropyl-6-cyclopropylmethoxy-pyrazine-2-carboxylic acid ((S)-2-cyclopropyl-1-dimethylcarbamoyl-ethyl)-amide;
5-Cyclopropyl-6-cyclopropylmethoxy-pyrazine-2-carboxylic acid ((S)-3-methyl-1-methylcarbamoyl-butyl)-amide;
5-Cyclopropyl-6-cyclopropylmethoxy-pyrazine-2-carboxylic acid ((S)-1-dimethylcarbamoyl-3-methyl-butyl)-amide;
5-Cyclopropyl-6-cyclopropylmethoxy-pyrazine-2-carboxylic acid ((S)-1-carbamoyl-2-cyclopropyl-ethyl)-amide;
5-Cyclopropyl-6-cyclopropylmethoxy-pyrazine-2-carboxylic acid ((S)-1-carbamoyl-3-methyl-butyl)-amide;
2-[(5-Cyclopropyl-6-cyclopropylmethoxy-pyrazine-2-carbonyl)-amino]-2-ethyl-butyric acid methyl ester;
6-Cyclopropylmethoxy-5-(3,3-difluoro-azetidin-1-yl)-pyrazine-2-carboxylic acid ((S)-2-cyclopropyl-1-methylcarbamoyl-ethyl)-amide;
6-Cyclopropylmethoxy-5-(3,3-difluoro-azetidin-1-yl)-pyrazine-2-carboxylic acid ((S)-2-cyclopropyl-1-dimethylcarbamoyl-ethyl)-amide;
6-Cyclopropylmethoxy-5-(3,3-difluoro-azetidin-1-yl)-pyrazine-2-carboxylic acid ((S)-3-methyl-1-methylcarbamoyl-butyl)-amide;
6-Cyclopropylmethoxy-5-(3,3-difluoro-azetidin-1-yl)-pyrazine-2-carboxylic acid ((S)-1-dimethylcarbamoyl-3-methyl-butyl)-amide;
(S)-3-Cyclopropyl-2-[(5-cyclopropyl-6-cyclopropylmethoxy-pyrazine-2-carbonyl)-amino]-propionic acid methyl ester;
(S)-3-Cyclopropyl-2-{[6-cyclopropylmethoxy-5-(3,3-difluoro-azetidin-1-yl)-pyrazine-2-carbonyl]-amino}-propionic acid methyl ester;
5-Cyclopropyl-6-cyclopropylmethoxy-pyrazine-2-carboxylic acid ((S)-1-carbamoyl-2-phenyl-ethyl)-amide;
6-Cyclopropylmethoxy-5-(3,3-difluoro-azetidin-1-yl)-pyrazine-2-carboxylic acid ((S)-1-carbamoyl-2-phenyl-ethyl)-amide;
6-Cyclopropylmethoxy-5-(3,3-difluoro-azetidin-1-yl)-pyrazine-2-carboxylic acid ((S)-1-carbamoyl-2-cyclopropyl-ethyl)-amide;
5-Cyclopropyl-6-cyclopropylmethoxy-pyrazine-2-carboxylic acid [(S)-cyclopropyl-(5-methyl-[1,2,4]oxadiazol-3-yl)-methyl]-amide;
5-Cyclopropyl-6-cyclopropylmethoxy-pyrazine-2-carboxylic acid [(R)-cyclopropyl-(5-methyl-[1,2,4]oxadiazol-3-yl)-methyl]amide;
6-Cyclopropylmethoxy-5-(3,3-difluoro-azetidin-1-yl)-pyrazine-2-carboxylic acid [(S)-cyclopropyl-(5-methyl-[1,2,4]oxadiazol-3-yl)-methyl]-amide;
6-Cyclopropylmethoxy-5-(3,3-difluoro-azetidin-1-yl)-pyrazine-2-carboxylic acid [(R)-cyclopropyl-(5-methyl-[1,2,4]oxadiazol-3-yl)-methyl]-amide;
(S)-2-[(5-Cyclopropyl-6-cyclopropylmethoxy-pyrazine-2-carbonyl)-amino]-3,3-dimethyl-butyric acid;
5-Cyclopropyl-6-cyclopropylmethoxy-pyrazine-2-carboxylic acid [1-methyl-1-(5-methyl-[1,2,4]oxadiazol-3-yl)-ethyl]-amide;
5-Cyclopropyl-6-cyclopropylmethoxy-pyrazine-2-carboxylic acid ((S)-1-pyridin-2-yl-ethyl)-amide;
6-Cyclopropylmethoxy-5-(3,3-difluoro-azetidin-1-yl)-pyrazine-2-carboxylic acid ((R)-2,2,2-trifluoro-1-pyridin-2-yl-ethyl)-amide;
6-Cyclopropylmethoxy-5-(3,3-difluoro-azetidin-1-yl)-pyrazine-2-carboxylic acid ((S)-2,2,2-trifluoro-1-pyridin-2-yl-ethyl)-amide;
5-Cyclopropyl-6-cyclopropylmethoxy-pyrazine-2-carboxylic acid ((S)-2,2,2-trifluoro-1-pyridin-2-yl-ethyl)-amide;
6-Cyclopropylmethoxy-5-(3,3-difluoro-azetidin-1-yl)-pyrazine-2-carboxylic acid (1-ethyl-1-methylcarbamoyl-propyl)-amide;
5-Cyclopropyl-6-cyclopropylmethoxy-pyrazine-2-carboxylic acid ((R)-1-hydroxymethyl-1,2-dimethyl-propyl)-amide;
5-Cyclopropyl-6-cyclopropylmethoxy-pyrazine-2-carboxylic acid ((S)-1-hydroxymethyl-1,2-dimethyl-propyl)-amide;
5-Cyclopropyl-6-cyclopropylmethoxy-pyrazine-2-carboxylic acid (1-ethyl-1-methylcarbamoyl-propyl)-amide;
5-Cyclopropyl-6-cyclopropylmethoxy-pyrazine-2-carboxylic acid [1-methyl-1-(4-methyl-thiazol-2-yl)-ethyl]-amide;
6-Cyclopropylmethoxy-5-(3,3-difluoro-azetidin-1-yl)-pyrazine-2-carboxylic acid [1-methyl-1-(4-methyl-thiazol-2-yl)-ethyl]-amide;
6-Cyclopropylmethoxy-5-(3,3-difluoro-azetidin-1-yl)-pyrazine-2-carboxylic acid [(R)-1-(5-methyl-[1,2,4]oxadiazol-3-yl)-ethyl]-amide;
5-Cyclopropyl-6-cyclopropylmethoxy-pyrazine-2-carboxylic acid [1-(5-amino-[1,2,4]oxadiazol-3-yl)-1-methyl-ethyl]amide;
6-Cyclopropylmethoxy-5-(3,3-difluoro-azetidin-1-yl)-pyrazine-2-carboxylic acid [1-(5-amino-[1,2,4]oxadiazol-3-yl)-1-methyl-ethyl]-amide;
6-Cyclopropylmethoxy-5-(3,3-difluoro-azetidin-1-yl)-pyrazine-2-carboxylic acid ((S)-1-carbamoyl-1-phenyl-ethyl)-amide;
6-Cyclopropylmethoxy-5-(3,3-difluoro-azetidin-1-yl)-pyrazine-2-carboxylic acid [2-cyclopropyl-1-methyl-1-(5-methyl-[1,2,4]oxadiazol-3-yl)-ethyl]-amide;
6-Cyclopropylmethoxy-5-(3,3-difluoro-azetidin-1-yl)-pyrazine-2-carboxylic acid [1-cyclopropyl-1-(5-methyl-[1,2,4]oxadiazol-3-yl)-ethyl]-amide;
5-Cyclopropyl-6-cyclopropylmethoxy-pyrazine-2-carboxylic acid [1-cyclopropyl-1-(5-methyl-[1,2,4]oxadiazol-3-yl)-ethyl]-amide;
5-Cyclopropyl-6-cyclopropylmethoxy-pyrazine-2-carboxylic acid [(S)-carbamoyl-(4-fluoro-phenyl)-methyl]-amide;
6-Cyclopropylmethoxy-5-(3,3-difluoro-azetidin-1-yl)-pyrazine-2-carboxylic acid [(S)-carbamoyl-(4-fluoro-phenyl)-methyl]-amide;

5-Cyclopropyl-6-cyclopropylmethoxy-pyrazine-2-carboxylic acid [(S)-2-cyclopropyl-1-(5-methyl-[1,2,4]oxadiazol-3-yl)-ethyl]-amide;
6-Cyclopropylmethoxy-5-(3,3-difluoro-azetidin-1-yl)-pyrazine-2-carboxylic acid [(S)-3-methyl-1-(2,2,2-trifluoro-ethylcarbamoyl)-butyl]-amide;
6-Cyclopropylmethoxy-5-(3,3-difluoro-azetidin-1-yl)-pyrazine-2-carboxylic acid [(S)-carbamoyl-(4-chlorophenyl)-methyl]-amide;
5-Cyclopropyl-6-cyclopropylmethoxy-pyrazine-2-carboxylic acid (4-hydroxy-1,1-dimethyl-butyl)-amide;
5-Cyclopropyl-6-cyclopropylmethoxy-pyrazine-2-carboxylic acid (1,1-dimethyl-3-pyridin-4-yl-propyl)-amide;
5-Cyclopropyl-6-cyclopropylmethoxy-pyrazine-2-carboxylic acid [1,1-dimethyl-2-(5-methyl-2-phenyl-oxazol-4-yl)-ethyl]-amide;
5-Cyclopropyl-6-cyclopropylmethoxy-pyrazine-2-carboxylic acid (1,1-dimethyl-3-pyridin-4-yl-butyl)-amide;
1-{[6-Cyclopropylmethoxy-5-(3,3-difluoro-azetidin-1-yl)-pyrazine-2-carbonyl]-amino}-cyclobutanecarboxylic acid methyl ester;
5-Cyclopropyl-6-cyclopropylmethoxy-pyrazine-2-carboxylic acid [1-methyl-1-(5-methyl-thiazol-2-yl)-ethyl]-amide;
6-Cyclopropylmethoxy-5-(3,3-difluoro-azetidin-1-yl)-pyrazine-2-carboxylic acid [1-methyl-1-(5-methyl-thiazol-2-yl)-ethyl]-amide;
5-Cyclopropyl-6-cyclopropylmethoxy-pyrazine-2-carboxylic acid ((S)-1-carbamoylmethyl-2-methyl-propyl)-amide;
6-Cyclopropylmethoxy-5-(3,3-difluoro-azetidin-1-yl)-pyrazine-2-carboxylic acid ((S)-1-carbamoylmethyl-2-methyl-propyl)-amide;
(+)-6-Cyclopropylrnethoxy-5-(3,3-difluoro-azetidin-1-yl)-pyrazine-2-carboxylic acid [2-cyclopropyl-1-methyl-1-(5-methyl-[1,2,4]oxadiazol-3-yl)-ethyl]-amide;
(−)-6-Cyclopropylmethoxy-5-(3,3-difluoro-azetidin-1-yl)-pyrazine-2-carboxylic acid [2-cyclopropyl-1-methyl-1-(5-methyl-[1,2,4]oxadiazol-3-yl)-ethyl]-amide;
2-Cyclopropyl-2-{[6-cyclopropylmethoxy-5-(3,3-difluoro-azetidin-1-yl)-pyrazine-2-carbonyl]-amino}-propionic acid methyl ester;
(+)-6-Cyclopropylmethoxy-5-(3,3-difluoro-azetidin-1-yl)-pyrazine-2-carboxylic acid ((1R,2S)-rel-2-carbamoyl-cyclohexyl)-amide;
(−)-5-Cyclopropyl-6-cyclopropylmethoxy-pyrazine-2-carboxylic acid cis-2-carbamoyl-cyclohexyl)-amide;
(+)-5-Cyclopropyl-6-cyclopropylmethoxy-pyrazine-2-carboxylic acid cis-2-carbamoyl-cyclohexyl)-amide;
5-Cyclopropyl-6-cyclopropylinethoxy-pyrazine-2-carboxylic acid (3-carbamoylmethyl-oxetan-3-yl)-amide;
6-Cyclopropylmethoxy-5-(3,3-difluoro-azetidin-1-yl)-pyrazine-2-carboxylic acid (3-carbamoylmethyl-oxetan-3-yl)-amide;
(+)-6-Cyclopropylmethoxy-5-(3,3-difluoro-azetidin-1-yl)-pyrazine-2-carboxylic acid [1-cyclopropyl-1-(5-methyl-[1,2,4]oxadiazol-3-yl)-ethyl]-amide;
(−)-6-Cyclopropylmethoxy-5-(3,3-difluoro-azetidin-1-yl)-pyrazine-2-carboxylic acid [1-cyclopropyl-1-(5-methyl[1,2,4]oxadiazol-3-yl)-ethyl]amide;
6-Cyclopropylmethoxy-5-(3,3-difluoro-azetidin-1-yl)-pyrazine-2-carboxylic acid (1-carbamoyl-2-methyl-propyl)-amide;
6-Cyclopropylmethoxy-5-(3,3-difluoro-azetidin-1-yl)-pyrazine-2-carboxylic acid (1-carbamoyl-cyclohexyl)-amide;
6-Cyclopropylmethoxy-5-(3,3-difluoro-azetidin-1-yl)-pyrazine-2-carboxylic acid (1-hydroxymethyl-cyclohexyl)-amide;
6-Cyclopropylmethoxy-5-(3,3-difluoro-azetidin-1-yl)-pyrazine-2-carboxylic acid (1-dimethylcarbamoyl-2-methyl-propyl)-amide;
5-Cyclopropyl-6-cyclopropylmethoxy-pyrazine-2-carboxylic acid (1-dimethylcarbamoyl-2-methyl-propyl)-amide;
6-Cyclopropylmethoxy-5-(3,3-difluoro-azetidin-1-yl)-pyrazine-2-carboxylic acid (5-chloro-thiophen-2-yl)-amide;
5-Cyclopropyl-6-cyclopropylmethoxy-pyrazine-2-carboxylic acid (1-hydroxymethyl-cyclohexyl)-amide;
5-Cyclopropyl-6-cyclopropylmethoxy-pyrazine-2-carboxylic acid (3-methoxy-1,1-dimethyl-propyl)-amide;
6-Cyclopropylmethoxy-5-(3,3-difluoro-azetidin-1-yl)-pyrazine-2-carboxylic acid (2-cyclobutyl-1-methylcarbarnoyl-ethyl)-amide;
6-Cyclopropylmethoxy-5-(3,3-difluoro-azetidin-1-yl)-pyrazine-2-carboxylic acid (2-cyclobutyl-1-dimethylcarbamoyl-ethyl)-amide;
5-Cyclopropyl-6-cyclopropylmethoxy-pyrazine-2-carboxylic acid (2-cyclobutyl-1-methylcarbarnoyl-ethyl)-amide;
6-Cyclopropylmethoxy-5-(3,3-difluoro-azetidin-1-yl)-pyrazine-2-carboxylic acid (3-methoxy-1,1-dimethyl-propyl)-amide;
6-Cyclopropylmethoxy-5-(3,3-difluoro-azetidin-1-yl)-pyrazine-2-carboxylic acid (1-cyclobutylmethyl-2-hydroxy-ethyl)-amide;
6-Cyclopropylmethoxy-5-(3,3-difluoro-azetidin-1-yl)-pyrazine-2-carboxylic acid (1-carbamoyl-2-cyclobutyl-ethyl)-amide;
5-Cyclopropyl-6-cyclopropylmethoxy-pyrazine-2-carboxylic acid (2-cyclobutyl-1-dimethylcarbamoyl-ethyl)-amide;
5-Cyclopropyl-6-cyclopropylmethoxy-pyrazine-2-carboxylic acid (1-carbamoyl-2-cyclobutyl-ethyl)-amide;
5-Cyclopropyl-6-cyclopropylmethoxy-pyrazine-2-carboxylic acid (1-cyclobutylmethyl-2-hydroxy-ethyl)-amide;
5-Cyclopropyl-6-cyclopropylmethoxy-pyrazine-2-carboxylic acid (2-carbamoyl-1,1-dimethyl-ethyl)-amide;
6-Cyclopropylmethoxy-5-(3,3-difluoro-azetidin-1-yl)-pyrazine-2-carboxylic acid (2-carbamoyl-1,1-dimethyl-ethyl)-amide;
(S)-2-{[6-Cyclopropylmethoxy-5-(3,3-difluoro-azetidin-1-yl)-pyrazine-2-carbonyl]-amino}-4-methyl-pentanoic acid methyl ester; and
6-Cyclopropylmethoxy-5-(3,3-difluoro-azetidin-1-yl)-pyrazine-2-carboxylic acid (1,1-dimethyl-3-phenyl-propyl)-amide.

2. A pharmaceutical composition comprising a compound according to claim 1 and a therapeutically inert carrier.

* * * * *